(12) United States Patent
Harris et al.

(10) Patent No.: US 7,432,349 B2
(45) Date of Patent: Oct. 7, 2008

(54) TUMOR SUPPRESSOR GENE, P28ING5

(75) Inventors: Curtis C. Harris, Garrett Park, MD (US); Remy Pedeux, Chevy Chase, MD (US); Makoto Nagashima, Sakura (JP); Masayuki Shiseki, Tokyo (JP)

(73) Assignee: The United States of America as represented by the Department of Health and Human Services, Washington, DC (US)

( * ) Notice: Subject to any disclaimer, the term of this patent is extended or adjusted under 35 U.S.C. 154(b) by 412 days.

(21) Appl. No.: 10/502,431

(22) PCT Filed: Jan. 23, 2003

(86) PCT No.: PCT/US03/02174

§ 371 (c)(1),
(2), (4) Date: Jul. 22, 2004

(87) PCT Pub. No.: WO03/062398

PCT Pub. Date: Jul. 31, 2003

(65) Prior Publication Data

US 2005/0097626 A1    May 5, 2005

Related U.S. Application Data

(60) Provisional application No. 60/351,504, filed on Jan. 23, 2002.

(51) Int. Cl.
*C07K 5/10* (2006.01)
(52) U.S. Cl. .................................................. 530/350
(58) Field of Classification Search .................. None
See application file for complete search history.

(56) References Cited

U.S. PATENT DOCUMENTS

| | | | |
|---|---|---|---|
| 5,965,398 A | | 10/1999 | Garkavtsev et al. |
| 6,066,474 A | * | 5/2000 | Marcu ....................... 435/69.1 |
| 6,117,633 A | | 9/2000 | Garkavtsev et al. |
| 6,238,918 B1 | | 5/2001 | Garkavtsev et al. |
| 2004/0058379 A1 | | 3/2004 | Harris et al. |
| 2004/0115747 A1 | | 6/2004 | Harris et al. |
| 2006/0127894 A1 | * | 6/2006 | Azimzai et al. ............... 435/6 |

FOREIGN PATENT DOCUMENTS

| | | |
|---|---|---|
| WO | WO 01/36476 | 5/2001 |
| WO | WO 01/47959 | 7/2001 |

OTHER PUBLICATIONS

Garkavtsev et al., "Suppression of the Novel Grwoth Inhibitor p33$^{ING1}$ Promotes Neoplastic Transformation," *Nature Genetics* 14:415-420, 1996.
Garkavtsev et al., "Extension of the Replicative Life Span of Human Diploid Fibroblasts by Inhibition of the p33$^{ING1}$ Candidate Tumor Suppressor," *Mol. Cell Biol.* 17(4):2014-2019, Apr. 1997.
Garkavtsev et al., "The Candidate Tumour Suppressor p33$^{ING1}$ Cooperates with p53 in Cell Growth Control," *Nature* 391:295-298, 1998.
Loewith et al., "Three Yeast Proteins Related to the Human Candidate Tumor Suppressor p33$^{ING1}$ Are Associated with Histone Acetyltransferase Activities," *Mol. Cell Biol.* 20(11):3807-3816, Jun. 2000.
Zeremski et al., "Structure and Regulation of the Mouse *ing1* Gene," *J. Biol. Chem* 274(45):32172-32181, 1999.
GenBank Accession No. AAB82387, Oct. 25, 1997, 2 pages.
GenBank Accession No. AAD48585, Aug. 12, 1999, 1 page.
GenBank Accession No. AF110645, Aug. 12, 1999, 2 pages.
GenBank Accession No. AF189286, Jan. 30, 2002, 2 pages.
GenBank Accession No. AX147962, Jun. 8, 2001, 1 page.
GenBank Accession No. BC005370, Jul. 12, 2001, 2 pages.
GenBank Accession No. BG170225, Feb. 6, 2001, 2 pages.
GenBank Accession No. BG753113, May 15, 2001, 2 pages.
GenBank Accession No. NM_032329, May 19, 2001, 2 pages.
GenBank Accession No. NP_115705.1, May 19, 2001, 1 page.

* cited by examiner

*Primary Examiner*—Misook Yu
*Assistant Examiner*—Mark Halvorson
(74) *Attorney, Agent, or Firm*—Klarquist Sparkman, LLP

(57) ABSTRACT

This disclosure provides a novel tumor suppressor, referred to as p28ING5, nucleic acid molecules encoding this protein, and methods of making and using these molecules. Also provided are methods of ameliorating, treating, detecting, prognosing, and diagnosing diseases and conditions associated with abnormal p28ING5 expression, such as neoplasia. Kits are also provided.

3 Claims, 12 Drawing Sheets

Figure 12

```
p33ING1b    1  ----------MLSPANGEQLHLVN-▓V▓░░░░▓S░░F░░░░VS▓▓R▓░I░AKY░EIL
p33ING2     1  MLGQQQQQLYSSAALLTGERSRLLTC░VQ░░░ECV░S░░H░M░░VSVL░░░NKY░ETL
p47ING3     1  ------------------------ML░░░░EM░░Q░░M░░RDR░TE░░M░LQV░NAM
p29ING4     1  ------------------MAAGM░░░H░░░░░N░░FE░░░░░Q░░░D░QRTEDLK
p28ING5     1  ------------------MATAM░░░H░░░░░N░CE░░░░░Q░░░░░QRTEDKK p33ING1b   49  K░L░ECYERFS---RETDGA░░RRM░HCV░R░LIRSQ░L░░I░IVS░MV░░░ENRT░Q
p33ING2    61  K░░░DVYEK░K---░EDDLN░░KRLQQLL░R░LINSQ░L░░░░IVT░MLE░░ENRA░Q
p47ING3    37  DQLEQRVS░FFMNA░KNKPEWREEQMAS░KKD░Y░AL░DA░░░░░N░I░D░░░R░L░K
p29ING4    40  A░░░KLAT░░MSSARSLSSEE░LAL░KQ░░E░░G░CK░F░░D░░░M░T░░M░░K░I░R
p28ING5    40  A░░░ILAA░░ISTV░░TLSPD░RVER░QK░░N░S░CK░YS░D░░░M░T░░M░░K░I░R p33ING1b  106  V░SHVEL░░QQ░LG---------------------------------------------
p33ING2   118  MELHSQC░QDPA░S---------------------------------------------
p47ING3    97  ░░QE░░K░KME░░ADNAGITEILERRSLELDTPSQPVNNHHAHSHTPVEKRKYNPTSHHT
p29ING4   100  ░░TD░░R░EAD░KEK--------------------------------------------
p28ING5   100  ░░AD░░R░EAD░KDK-------------------------------------------- p33ING1b  121  -----------------------------DTAGNSGKAGADR░KGEAAAQAD
p33ING2   132  -----------------------------ERASDKAKMD░░Q░--ER--SSR
p47ING3   157  TTDHIPEKKFKSEALLSTLTSDASKENTLGCRNNNSTASSNNAYNVN░░Q░LGSYNIGSL
p29ING4   115  -----------------------------QIESSDYDSS░░KGK--------
p28ING5   115  -----------------------------MEGSDFESSGGRGL-------- p33ING1b  144  KPNS---------------KRSRRQ░NNENRENASSNHDH------------------
p33ING2   151  RP----------------RRQ░TSESRDLCHMANGI------------------
p47ING3   217  SSGTGAGAITMAAAQAVQATAQM░E░░RTSSLKASYEAFKNNDFQLGKEFSMARETVGYS
p29ING4   130  -----------------------░K░░TQKEKKAARARSKG----------------
p28ING5   129  -----------------------░K░░GQKEKRGSRGRGR---------------- p33ING1b  169  ----------DDGASGT░░---E░░A░----T░KKK----------------
p33ING2   171  ----------EDCDDQP░░---E░░S░----SAKKK----------------
p47ING3   277  SSSALMTTLTQNASSSAADSRSGR░S░NNNKS░SQQSSSSSSSSSLSSCSSSSTVVQEIS
p29ING4   148  ----------KNSDEEA░░T-AQ░░L░LV-RT░PEYG----------------
p28ING5   146  ----------RTSEEDT░░---K░░H░----GGSEP---------------- p33ING1b  188  -KRSKAKAEREA░PA░L░I░░░░░░░░░░░░░░░░░░L░░DE░░░░░░S░░░NH░
p33ING2   190  -KRSKAKQEREA░PVEFAI░░░░░░░░░░░░░░░░░T░░EQ░░░░░S░░S░TY░
p47ING3   337  QQTTVVPESDSN░QV░WTY░░░░░░░I░░░░░░V░░░░░Q░░░░YG░░░EA
p29ING4   173  MPSVTFGSVHPSDVL░M░V░░░░░░░░░░░░░░░░░░░░░░P░░░░░░A░░░T░
p28ING5   165  --TDTILSVHPSDVL░M░V░░░░░░░░░░░░░░░░░░░░L░P░░░░░░A░░░T░
                                  *  *        *    *     *   * p33ING1b  247  ░░░░░░RG░NE░TMDKALEKSKKERAYNR
p33ING2   249  ░░░░░░RGDNE░TMDKSTEKTKKDRRSR-
p47ING3   397  ░░░░░░░Q░TAAMKRRGSRHK--------
p29ING4   233  ░R░░F░░R░SQ░RK░K-------------
p28ING5   223  ░░░░░F░R░V Q░KR░KK-----------
                   * *
```

TUMOR SUPPRESSOR GENE, P28ING5

REFERENCE TO RELATED APPLICATIONS

This is the § 371 U.S. National Stage of International Application No. PCT/US03/02174, filed on Jan. 23. 2003, which was published in English under PCT Article 21(2), and which in turn claims the benefit of U.S. Provisional Application No. 60/351,504, filed Jan. 23, 2002, both of which are incorporated herein by reference.

FIELD OF THE DISCLOSURE

The present disclosure is related to tumor suppressors, particularly a new ING tumor suppressor and nucleic acids that encode it, as well as its uses in vitro and in vivo.

BACKGROUND OF THE DISCLOSURE

Tumor suppressor genes encode proteins that inhibit progression through the cell cycle, thereby inhibiting cell growth and/or cell division. When DNA damage is detected in a cell, tumor suppressors prevent the cell from continuing to multiply until the damaged DNA is repaired. Alternatively, if the DNA cannot be repaired, they may signal the cell to undergo apoptosis (programmed cell death) in order to prevent the damaged DNA from being passed on to the daughter cells. Tumor suppressors therefore play a critical role in preventing the onset of uncontrolled cell growth, or neoplasia.

Most tumor suppressor genes are recessive, and the development of a tumor usually requires two separate mutational events. Only when both alleles of a tumor suppressor gene are lost or damaged is the control that it exerted on cell growth lost, thereby allowing neoplasia. One of these mutational events may occur in the germline and be inherited; the second then occurs somatically. Alternatively, the two mutational events may occur only in the somatic cell of an individual.

Two of the best-characterized tumor suppressor genes are the retinoblastoma (Rb) and p53 genes. Mutations in both alleles of the Rb gene results in the development of retinoblastoma, a malignant tumor of the retina which appears in infants and young children, and is also involved in the development of bone, bladder, small cell lung, and breast tumors. The Rb gene codes for the nuclear protein pRB that functions as a major inhibitor of the cell cycle.

The p53 gene is mutated in approximately half of the human tumors, and is therefore believed to be the most frequently mutated gene in human neoplasias. Mutated versions of p53 have been found in a variety of tumors, including those of the colon, brain, lung, and breast, and in leukemias and osteosarcomas.

Recently, a new tumor suppressor gene family, the ING family, has been identified (Garkavtsev et al., *Nat Genet.* 14:415-420, 1996; Gunduz et al., *Cancer Res.* 60:3143-3146, 2000; Saito et al., *J. Hum. Genet.* 45:177-181,2000; Jager et al., *Cancer Res.* 59:6197-204, 1999). Members include ING1 (which has three alternatively spliced forms: p47ING1a, p33ING1b and p24ING1c), and ING2.

p33ING1 shares many biological functions with p53. It has been reported to mediate growth arrest, senescence, apoptosis, anchorage-dependent growth, and chemosensitivity. Neither p53 or p33ING1 can inhibit cell growth on its own and specific biological functions, such as cell-cycle arrest and apoptosis, have been shown to be dependent on the activity of both of these proteins. Mutations in p33ING1 have been demonstrated in neuroblastoma cells and esophageal squamous cell carcinomas (Garkavtsev et al., *Nat. Genet* 14:415-420, 1996; Chen et al., *Cancer Res.* 61:4345-4349, 2001). Decreased p33ING1 expression in esophageal squamous cell carcinomas (Chen et al., *Cancer Res.*, 61:4345-4349,2001) and in lymphoid malignancies (Ohmori et al., *Am. J. Hematol.* 62:118-119, 1999) have also been described.

Relatively few tumor suppressor genes have been identified, given the number of recessive mutations that have been associated with neoplasias. Since tumor suppressor genes may function in a cell-specific manner, the few already identified may not be useful in treating all neoplasias. There is therefore a continuing need to identify and isolate other tumor suppressor genes as diagnostic and therapeutic agents for identification and treatment of neoplasias and other diseases.

SUMMARY OF THE DISCLOSURE

This disclosure provides a novel tumor suppressor, referred to as p28ING5. Encompassed within this disclosure is the cloning of the gene encoding this tumor suppressor, the sequences of the cDNA and the protein, and evidence demonstrating that p28ING5 acts as a tumor suppressor. Also provided are nucleotide and amino acid sequence variants, oligonucleotides and protein fragments. It is shown herein that p28ING5 is a nuclear protein that is endogenously expressed, to varying degrees, in a wide variety of tissues and cell lines. It is also disclosed that the p28ING5 cDNA can be operatively linked to a promoter and cells can be transfected with the recombinant polynucleotide.

Also provided herein are methods for using p28ING5, including methods to inhibit cellular proliferation. Examples of these methods include introducing a p28ING5 recombinant polynucleotide into a cell or contacting a cell with a p28ING5 polypeptide or fragment thereof. Also disclosed are the methods of administering a p28ING5 recombinant polynucleotide or p28ING5 polypeptide to a subject in order to treat, inhibit, ameliorate, prognose, diagnose, or prevent a neoplasm. In one embodiment, a p28ING5-specific binding agent is used to detect the presence of p28ING5 in a sample. Kits containing the p28ING5 recombinant polynucleotide or polypeptide are also disclosed.

The foregoing and other features and advantages will become more apparent from the following detailed description of several embodiments, which proceeds with reference to the accompanying figures.

SDS-polyacrylamide gel and electrophoretically transferred to Immobilon-P membrane (Millipore). The membrane was then probed with the anti-p28ING5 antiserum, followed by ECL (Amersham Pharmacia Biotech) to visualize the protein bands. Only the RKO cells transfected with the pcDNA3.1-ING5 vector expressed a protein that was recognized by the anti-p28ING5 antiserum.

Figure 4:
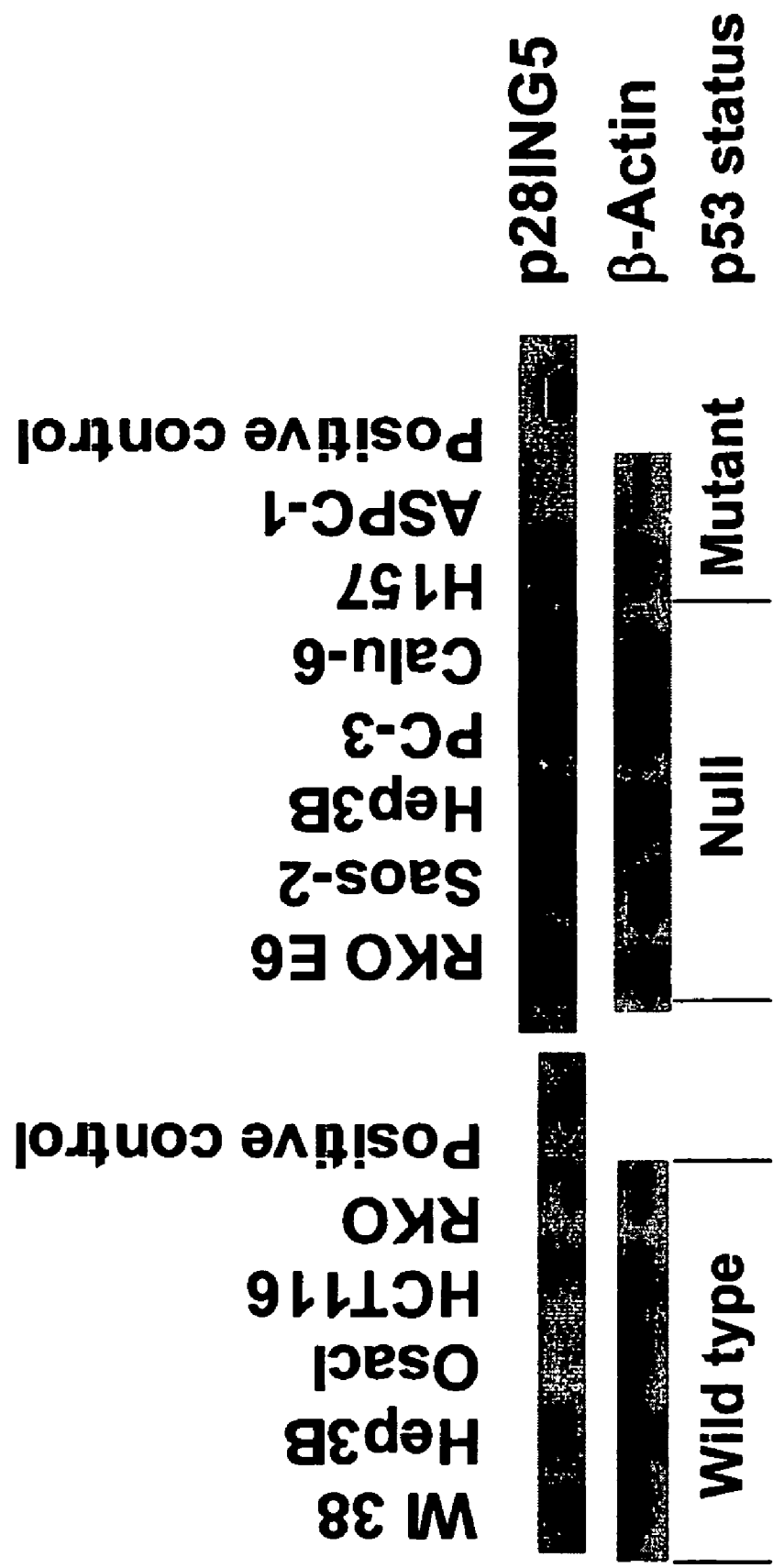

FIG. 4 is a series of Western blots showing the expression of p28ING5 in various cell lines. Twelve human cell lines which express either wildtype p53 (WI 38, Hep 3B, HCT 116, RKO), mutant p53 (NC1-H157, AsPC-1), or which are devoid of p53 (RKO E6, Saos-2, Hep3B, PC-3, Calu-6) were examined for the expression of p28ING5. Sub-confluent cultures of cells were harvested, lysed, electrophoresed, and electrophoretically transferred to PVDF membranes. The membrane was then probed with the anti-p28ING5 antiserum (1:200) and horseradish peroxidase-conjugated anti-rabbit IgG secondary antibody (1:2000). The membranes were treated with the ECL chemiluminescence kit, and exposed to ECL films (Amersham Pharmacia Biotech). The expression levels of p28ING5 varied among the cell lines examined. No correlation could be made between the level of p28ING5 expression and the status of p53 in the cells.

Figure 5:
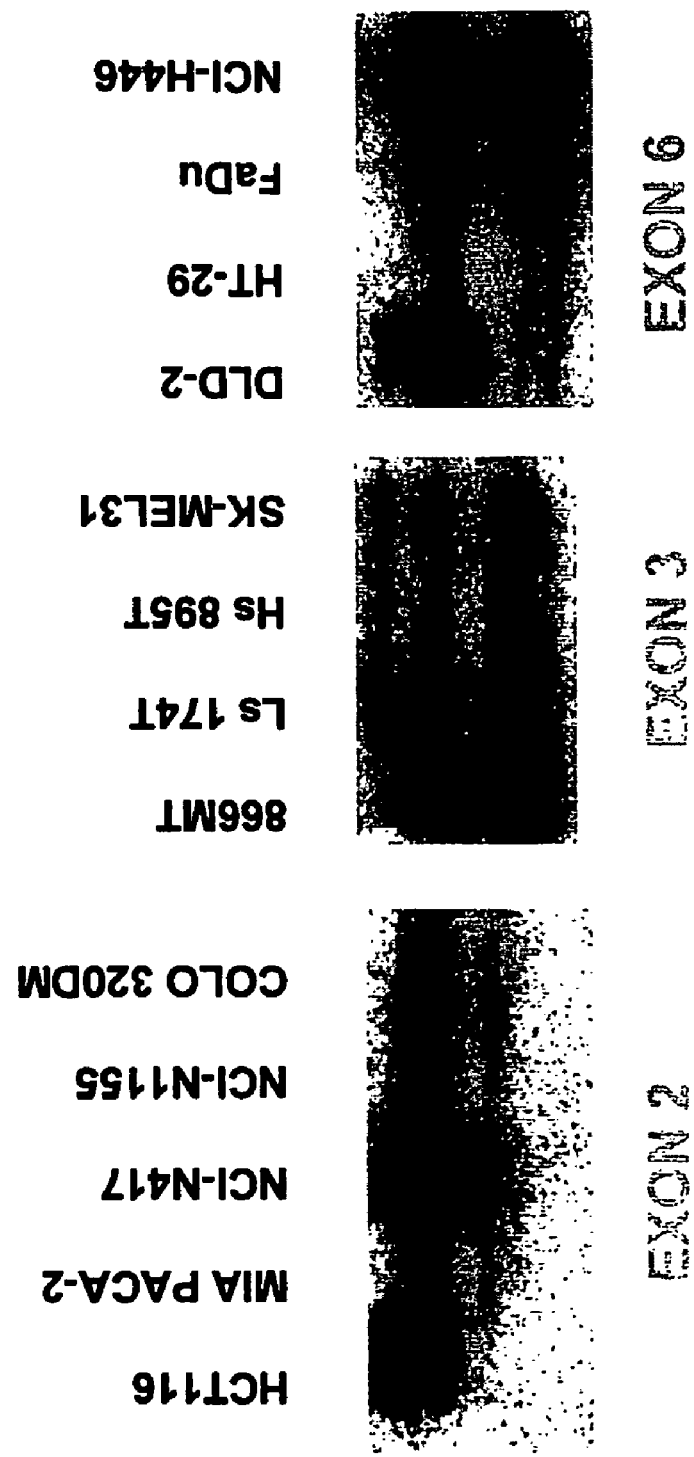

FIG. 5 shows PCR-SSCP analysis of the p28ING5 gene. Exon 2, exon 3, and exon 6 were amplified by PCR and analyzed for single-strand conformation polymorphisms. Four cell lines (HCT116, 866 MT, Ls174T, DLD-4) show aberrantly migrating bands on the SSCP gels.

Figure 6:
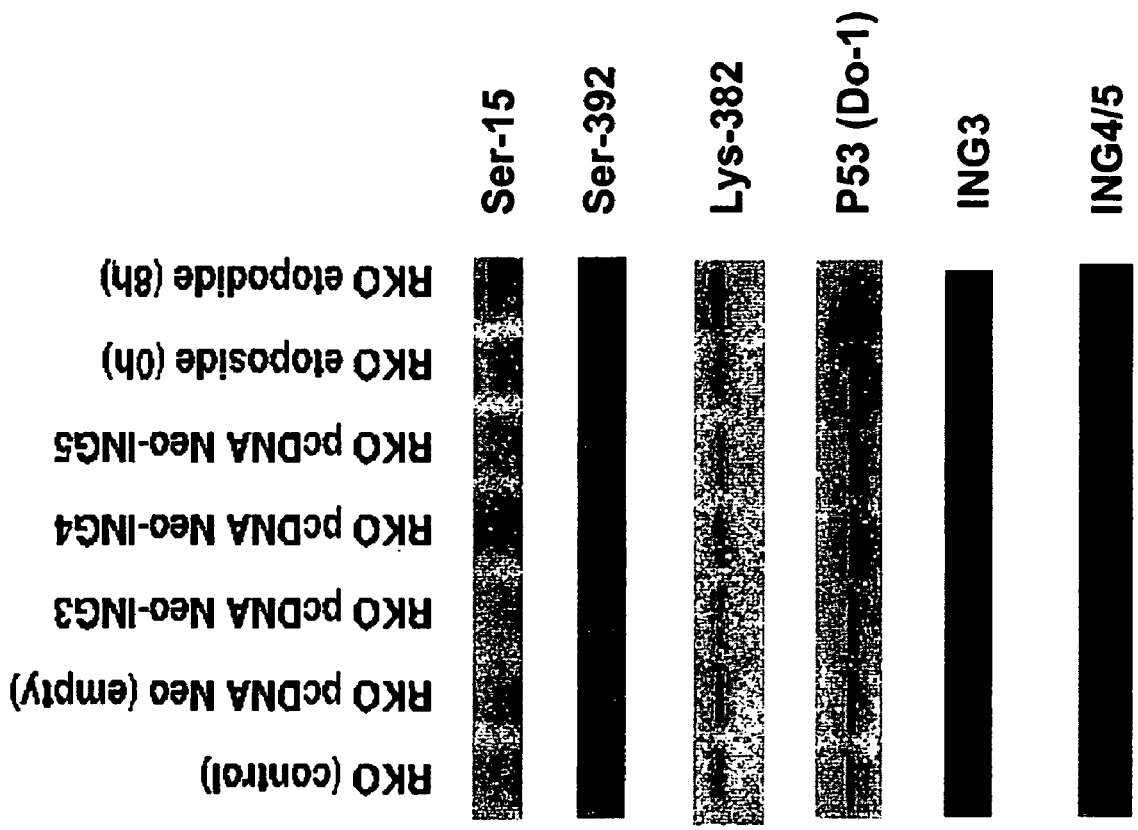

FIG. 6 is a series of Western blots showing the effect of p28ING5 over-expression on p53 post-translational modifications. RKO cells were seeded on 100 mm dishes at $2 \times 10^4$ cells/cm² and cultured for 24 hours. The cells were transfected with pcDNA3.1-p28ING5 or a control vector (pcDNA3.1). Cells were harvested at 24 hours post-transfection. In p53 acetylation experiments, trichostatin A was administered to the cells for 3 hours before they were harvested. Whole cell lysates were then subjected to Western blot analysis to detect p53 or p53 phosphorylated on the serine residues at positions 15 (Ser-15) or 392 (Ser-392). Alternatively, p53 acetylated on the lysine residue at position 382 (Lys-382), was first immunoprecipitated by anti-p53 Ab-6 and Pab 240 antibodies conjugated to agarose. The immunoprecipitate was then subjected to Western blot analysis to detect the acetylated p53. Over-expression of p28ING5 had little effect on the level of p53 expression, on the acetylation status of Lys-382, or on the phosphorylation state of Ser-15 or Ser-392.

Figure 7:
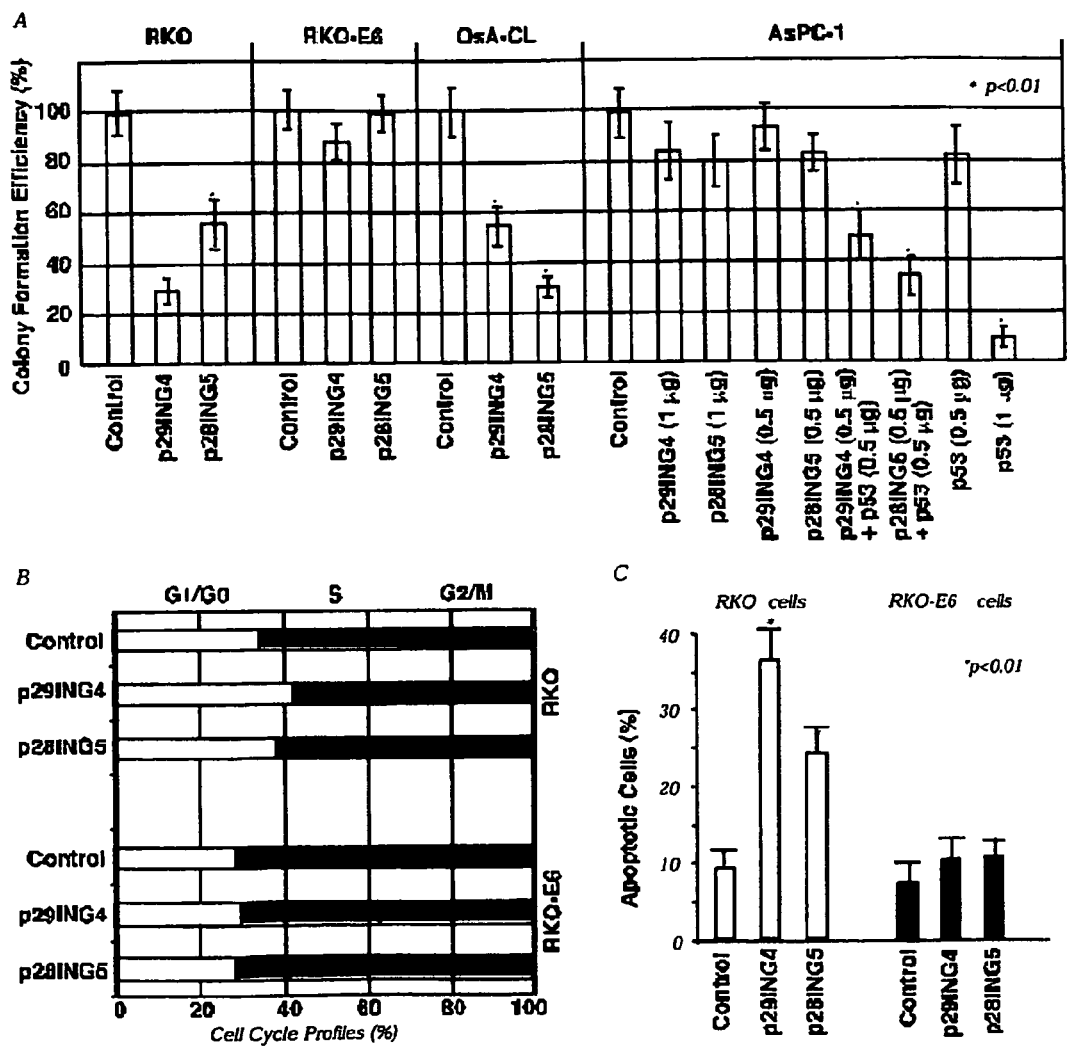

FIG. 7 is a series of bar graphs showing the negative regulation of cell proliferation by p29ING4 and p28ING5. FIG. 7A is a graph showing the results of a colony formation assay. RKO or RK0-E6 cells were transfected with pcDNA3.1-ING4, p28ING5, or pcDNA3.1 (control) vectors containing a hygromycin-resistance gene. OsA-CL or AsPC-1 cells were transfected with pcDNA3.1-ING4, pcDNA3.1-ING5, or pcDNA3.1 (control) vectors containing a neomycin-resistance gene. Colonies were counted following two weeks of selection. Data are shown as relative values to the control, and represent the average of three independent experiments. Statistical analysis was carried out using Student's t-test. FIG. 7B is a graph showing the effect of the overexpression of p29ING4 and p28ING5 on cell cycle profiles. RKO or RK0-E6 cells were co-transfected with pcDNA3.1-ING4, pcDNA3.1-ING5, or pcDNA3.1 (control) and pEGFP-F vector (Clontech) using the Lipofectamine Plus Reagent (Invitrogen). Forty-eight hours after transfection, cells were fixed and stained with propidium iodide and DNA content of the cells was measured by flow cytometry (FACSCalibur, Becton-Dickinson). Cell cycle profiles were analyzed using ModFit LT Program (Verify Software House). At least 10,000 of the GFP-positive cells were analyzed. FIG. 7C is a graph showing of the overexpression of p28ING5 and p29ING4 on the induction of apoptosis. RKO or RKO-E6 cells were plated onto eight-well chamber slides, and co-transfected with the pcDNA3.1-ING4, pcDNA3.1-ING5, pcDNA3.1 (control) or pEGFP-F vectors. Cells were fixed for 24 hours after transfection and fragmented DNA was detected by the TUNEL assay. The slides were observed by fluorescent microscopy, and 100 EGFP positive cells were analyzed for apoptosis. Data are shown as a percentage and represent the average of three independent experiments. Statistical analysis was carried out by Student's t-test.

Figure 8:
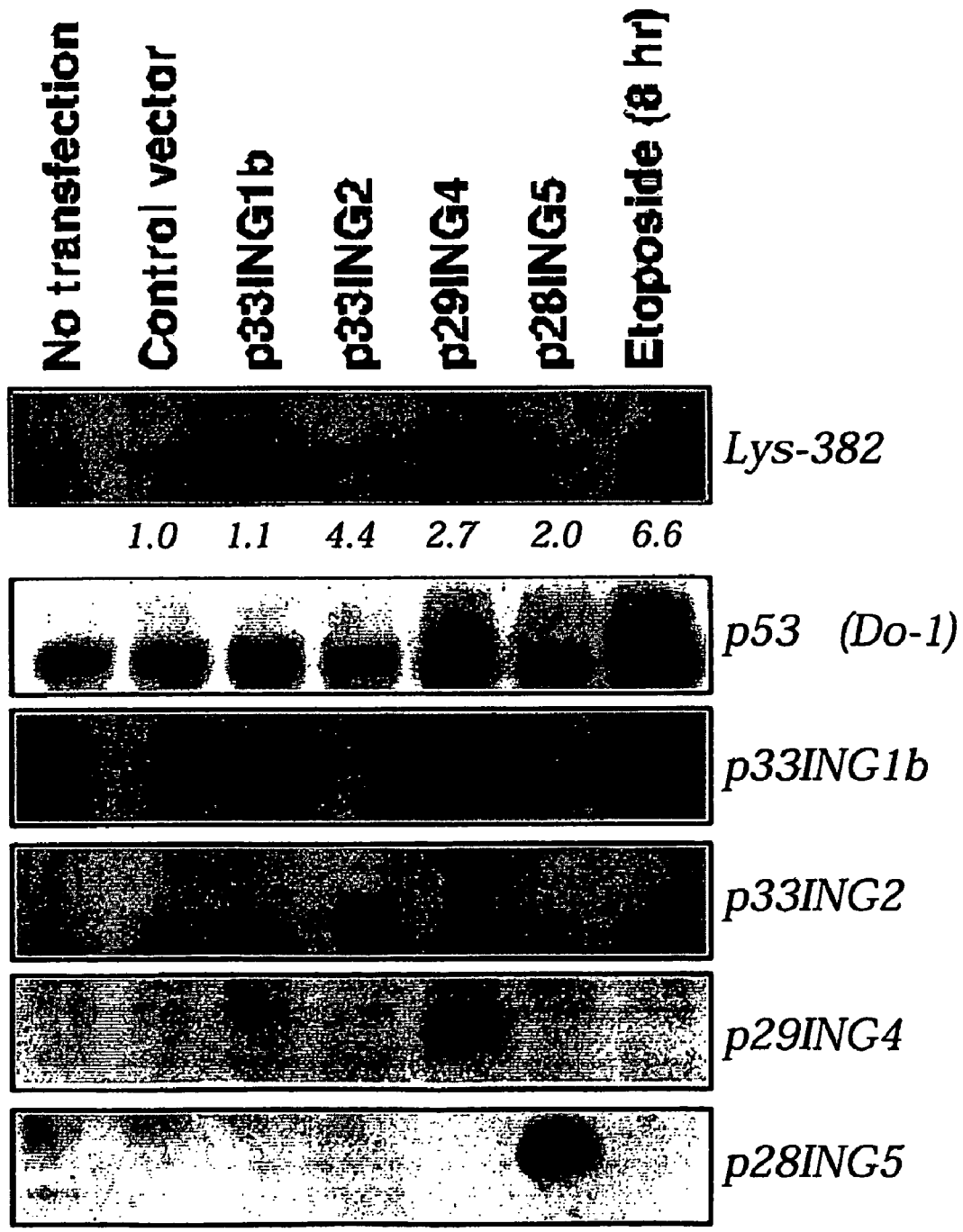

FIG. 8 is a series of digital images of Western blots showing the post-translational modifications of p53 by ING family protein overexpression. RKO cells were transfected with pcDNA3.1-ING1b, pcDNA3.1-ING2, pcDNA3.1-ING4, pcDNA3.I-ING5, or pcDNA3.1 (control vector). Acetylation of p53 at Lys-382 was detected in anti-p53 (DO-1 and Pab240) immunoprecipitates from RKO cells by Western blot analysis. Total p53 was detected with DO-1 antibody. ING proteins were detected with ING protein-specific antibodies. RKO cells treated with etoposide (20 µg/ml) for 8 hours were used as a positive control for acetylated p53. Numbers beneath the lanes in the upper panel are densitometry values as a relative ratio to the control.

Figure 9:
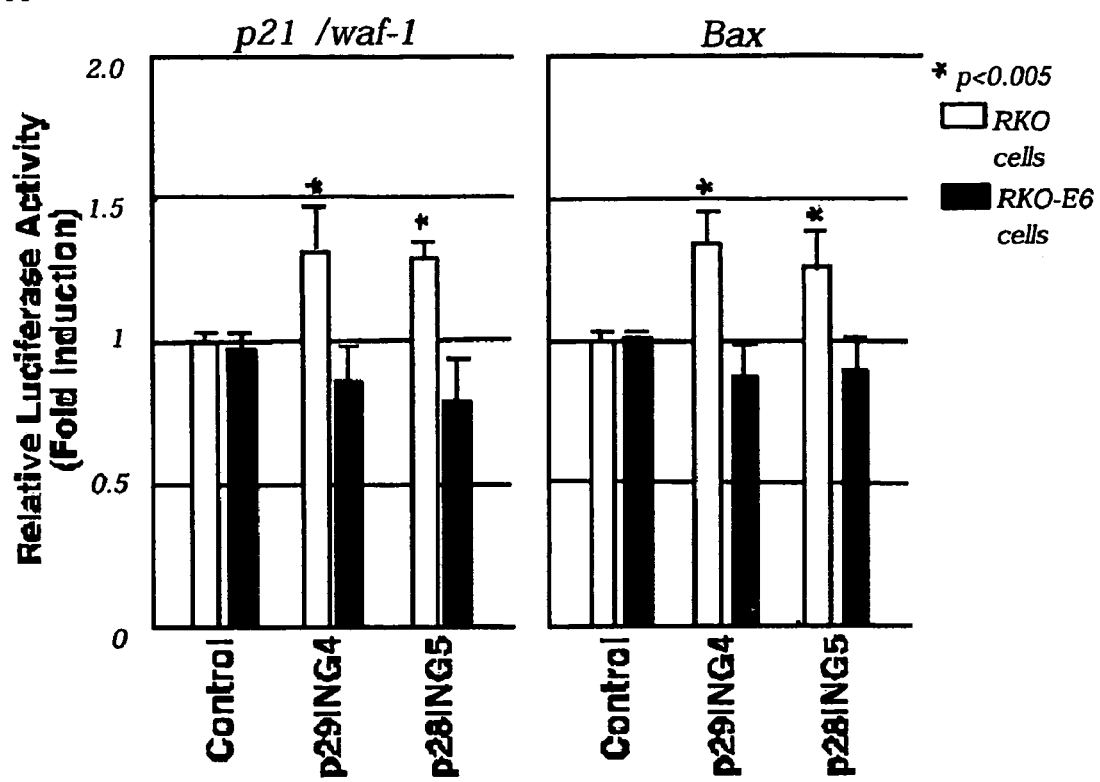
Figure 9:
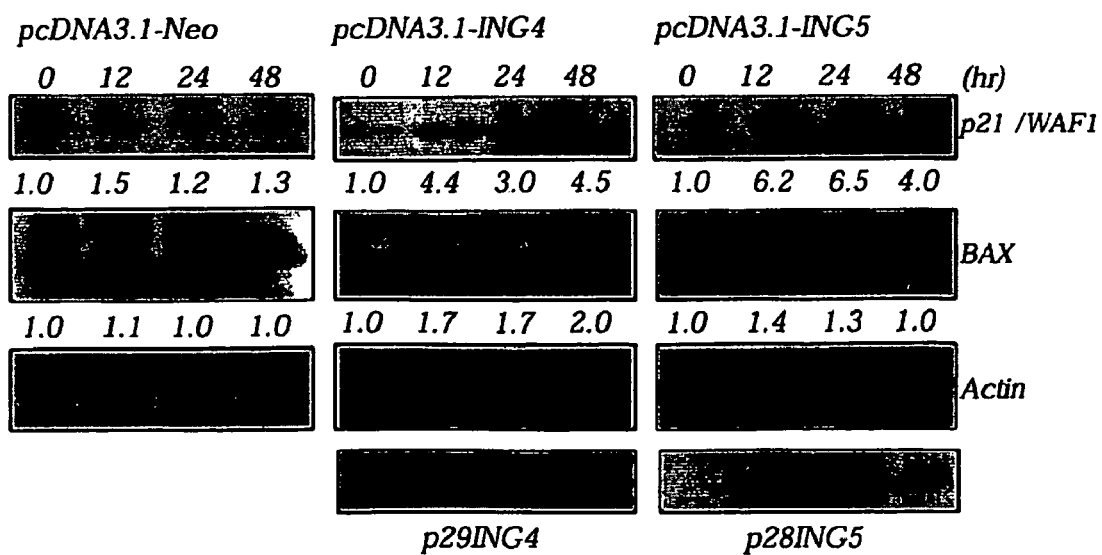

FIG. 9 shows the effect of p29ING4 and p28ING5 on the expression and promoter activity of the p21WAF1 and BAX genes. FIG. 9A is a graph showing the sequence-specific transcriptional activity of p53. Promoter activities of p21/waf1, or bax were detected after RKO, or RKO-E6 cells were co-transfected with p53-responsive promoter-luciferase constructs and either pcDNA3.1 (control), pcDNA3.1-ING4, or pcDNA3.1-ING5 vectors. The cells were also transfected with the pR-Tk vectors as an internal control vector. The luciferase activities were measured with a luminometer, and nommalized against an internal control. The data are shown as a relative value to the control promoter. Results represent the mean of six independent experiments. Statistical analysis was carried out by Student's t-test. FIG. 9B is a series of digital images of Western blots showing the increase in expression of p21/WAF1 and BAX, induced by p29ING4 or p28ING5 overexpression. RKO cells were transfected with pcDNA3.1-Neo (control), pcDNA3.1-ING4, or pcDNA3.1-ING5 vectors. Cells were harvested at different time-points after transfection. Whole cell lysates were prepared, electrophoresed, and subjected to Western blot analysis to detect p21/WAF1, BAX, in the presence of p29ING4 or p28ING5.

Figure 10:
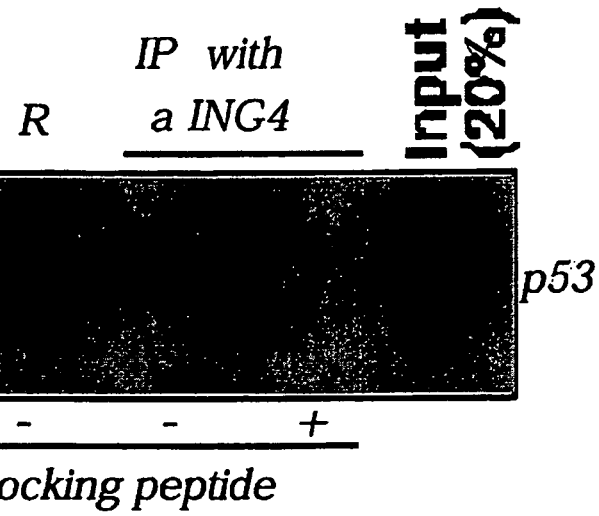
Figure 10:
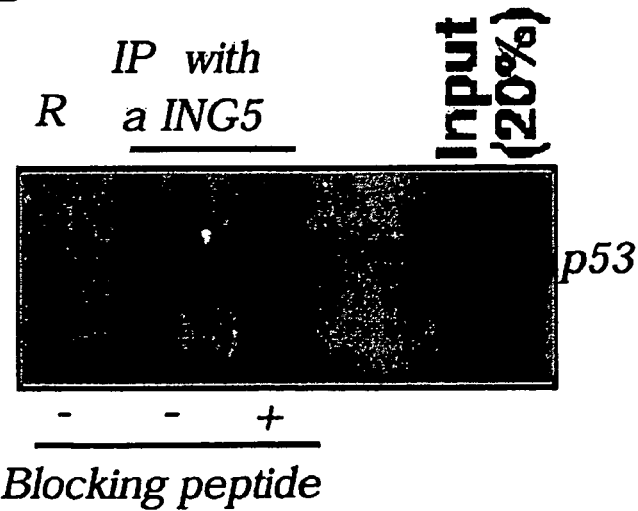
Figure 10:
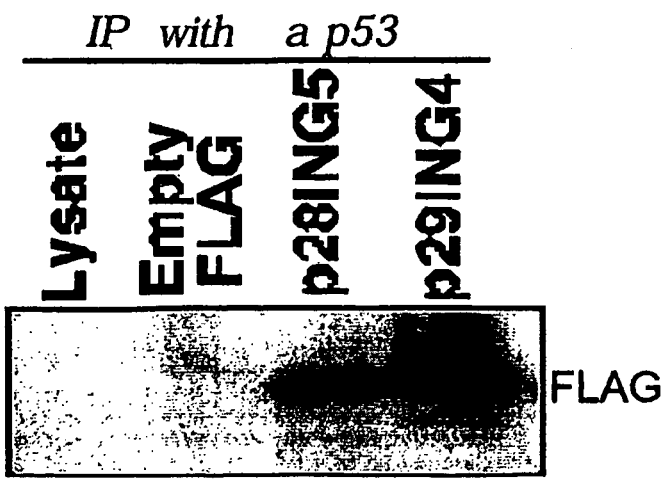

FIG. 10 is a series of digital images showing the in vivo interaction between p29ING4 or p28ING5 and p53. FIG. 10A shows the in vivo interaction between p29ING4 and p53. Cell lysates extracted from RKO cells transfected with pcDNA3.1-ING4 were immunoprecipitated with rabbit pre-immunized immunoglobulin (Ig)G (R) or anti-ING4 antibody, either with (+) or without (−) specific-blocking peptide. FIG. 10B show the in vivo interaction between p28ING5 and p53. p53 was detected using the DO-1 antibody. Cell lysates from RKO cells transfected with pcDNA3.1-ING5 were immunoprecipitated with preimmunized rabbit IgG (R) or anti-ING5 antibody, either with (+) or without (−) blocking peptides. FIG. 10C shows cell lysates, extracted from RKO cells transfected with FLAG-ING4 or FLAG-ING5, that were immunoprecipitated with anti-p53 antibodies (DO-1 and Pab 240). p29ING4 and p28ING5 were detected by Western blot analysis using the anti-FLAG antibody.

Figure 11:
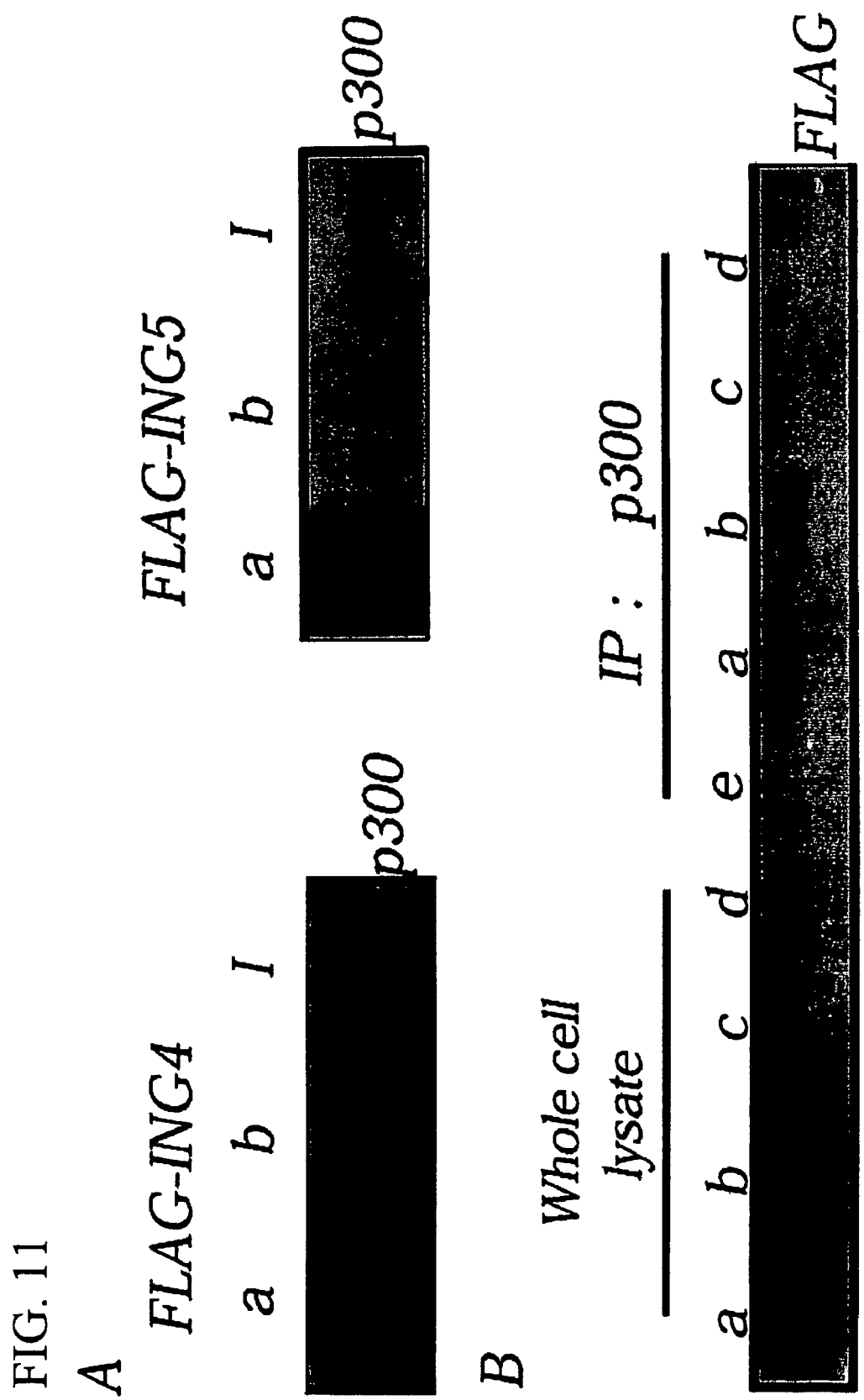

FIG. 11 is a series of digital images of Western blots showing the in vivo interactions between p29ING4 or p28ING5 and p300. FIG. 11A shows co-immunoprecipitations of p300 and p29ING4 or p28ING5. Whole cell lysates from the RKO cells transfected with FLAG-ING4, or FLAG-ING5 were prepared. One fifth of each of the whole cell lysates was set aside for electrophoresis (lane 1). One mg of the whole cell lysates prepared from the RKO cells transfected with FLAG-ING4, or FLAG-ING5 were immunoprecipitated with anti-FLAG M2 antibody alone (lane a) or with FLAG peptide (lane b). Immunoprecipitates were analyzed by Western blot to detect p300. FIG. 11B shows the co-immunoprecipitations of p29ING4 or p28ING5 with p300. Cell lysates from RKO cells transfected with FLAG-ING4 or FLAG-ING5 were immunoprecipitated with anti-p300 antibody (N-15, Santa Cruz Biotechnology), (a) RKO transfected with FLAG-ING4, (b) RKO transfected with FLAG-ING5, (c) RKO transfected with empty FLAG vector, (d) RKO lysate, and (e) no lysate. Co-mmunoprecipitates containing p29ING4 or p28ING5 were detected using the FLAG antibody and Western blot analysis.

FIG. 12 is an alignment of the following five ING family protein sequences: p33ING1b (SEQ ID NO: 3), p33ING2 (SEQ ID NO: 4), p47ING3 (SEQ ID NO: 5), p29ING4 (SEQ ID NO: 6), and p28ING5 (SEQ ID NO: 2). Asterisks below sequence alignments indicate the location of a PHD (plant homeo domain) motif (Cys (4)His-Cys (3)). Consensus positions are shown in darkened boxes; gaps are indicated by dashes.

BRIEF DESCRIPTION OF THE SEQUENCE LISTING

The nucleic and amino acid sequences listed in the accompanying sequence listing are shown using standard letter abbreviations for nucleotide bases, and three letter code for amino acids, as defined in 37 C.F.R. 1.822. Only one strand of each nucleic acid sequence is shown, but the complementary strand is understood as included by any reference to the displayed strand. In the accompanying sequence listing:

SEQ ID NO: 1 shows a cDNA encoding p28ING5 and the corresponding deduced amino acid sequence of p28ING5 (GenBank Accession No. AF 189286).

SEQ ID NO: 2 shows the amino acid sequence of p28ING5.

SEQ ID NO: 3 shows the amino acid sequence of p33ING1b.

SEQ ID NO: 4 shows the amino acid sequence of p33ING2.

SEQ ID NO: 5 shows the amino acid sequence of p47ING3.

SEQ ID NO: 6 shows the amino acid sequence of p29ING4.

DETAILED DESCRIPTION

I. Abbreviations
ASO allele specific oligonucleotide
BAC bacterial artificial chromosome
EGFP enhanced green fluorescent protein
ING INhibitor of Growth
FISH fluorescence in situ hybridization
FITC fluorescein isothiocyanate
Ig immunoglobulin
IRES internal ribosomal entry site
NLS nuclear localization signal
ORF open reading frame
PAC P1 artificial chromosome
PBS phosphate buffered saline
PCR polymerase chain reaction
PCR-SSCP PCR-single-strand conformational polymorphism
PHD plant homeo domain
PNA peptide nucleic acid
RT-PCR reverse transcriptase-PCR
SCID severe combined immune deficiency
YAC yeast artificial chromosome II. Terms Unless otherwise noted, technical terms are used according to conventional usage. Definitions of common terms in molecular biology may be found in Benjamin Lewin, *Genes V*, published by Oxford University Press, 1994 (ISBN 0-19-854287-9); Kendrew et al. (eds.), *The Encyclopedia of Molecular Biology*, published by Blackwell Science Ltd., 1994 (ISBN 0-632-02182-9); and Robert A. Meyers (ed.), *Molecular Biology and Biotechnology: a Comprehensive Desk Reference*, published by VCH Publishers, Inc., 1995 (ISBN 1-56081-569-8).

In order to facilitate review of the various embodiments of the invention, the following explanations of specific terms are provided:

Animal: Living multi-cellular vertebrate organisms, a category that includes for example, mammals and birds.

Amplification: When used in reference to a nucleic acid, techniques that increase the number of copies of a nucleic acid molecule in a sample or specimen. An example of amplification is the polymerase chain reaction, in which a biological sample collected from a subject is contacted with a pair of oligonucleotide primers, under conditions that allow for the hybridization of the primers to nucleic acid template in the sample. The primers are extended under suitable conditions, dissociated from the template, and then re-annealed, extended, and dissociated to amplify the number of copies of the nucleic acid. The product of in vitro amplification can be characterized by electrophoresis, restriction endonuclease cleavage patterns, oligonucleotide hybridization or ligation, and/or nucleic acid sequencing, using standard techniques. Other examples of in vitro amplification techniques include strand displacement amplification (see U.S. Pat. No. 5,744,311); transcription-free isothermal amplification (see U.S. Pat. No. 6,033,881); repair chain reaction amplification (see WO 90/01069); ligase chain reaction amplification (see EP-A-320 308); gap filling ligase chain reaction amplification (see U.S. Pat. No. 5,427,930); coupled ligase detection and PCR (see U.S. Pat. No. 6,027,889); and NASBA™ RNA transcription-free amplification (see U.S. Pat. No. 6,025,134).

Antisense, Sense, and Antigene: Double-stranded DNA (dsDNA) has two strands, a 5'->3' strand, referred to as the plus strand, and a 3'->5' strand (the reverse compliment), referred to as the minus strand. Because RNA polymerase adds nucleic acids in a 5'->3' direction, the minus strand of the DNA serves as the template for the RNA during transcription. Thus, the RNA formed will have a sequence complementary to the minus strand and identical to the plus strand (except that U is substituted for T).

Antisense molecules are molecules that are specifically hybridizable or specifically complementary to either RNA or the plus strand of DNA. Sense molecules are molecules that are specifically hybridizable or specifically complementary to the minus strand of DNA. Antigene molecules are either antisense or sense molecules directed to a dsDNA target.

Binding or stable binding: An oligonucleotide binds or stably binds to a target nucleic acid if a sufficient amount of the oligonucleotide forms base pairs or is hybridized to its target nucleic acid, to permit detection of that binding. Binding can be detected by either physical or functional properties of the target:oligonucleotide complex. Binding between a target and an oligonucleotide can be detected by any procedure known to one skilled in the art, including both functional and physical binding assays. Binding can be detected functionally by determining whether binding has an observable effect upon a biosynthetic process such as expression of a gene, DNA replication, transcription, translation and the like.

Physical methods of detecting the binding of complementary strands of DNA or RNA are well known in the art, and include such methods as DNase I or chemical footprinting, gel shift and affinity cleavage assays, Northern blotting, dot blotting and light absorption detection procedures. For example, one method that is widely used, because it is so simple and reliable, involves observing a change in light absorption of a solution containing an oligonucleotide (or an analog) and a target nucleic acid at 220 to 300 nm as the temperature is slowly increased. If the oligonucleotide or analog has bound to its target, there is a sudden increase in absorption at a characteristic temperature as the oligonucleotide (or analog) and the target disassociate from each other, or melt.

The binding between an oligomer and its target nucleic acid is frequently characterized by the temperature ($T_m$) at which 50% of the oligomer is melted from its target. A higher ($T_m$) means a stronger or more stable complex relative to a complex with a lower ($T_m$).

cDNA (complementary DNA): A piece of DNA lacking internal, non-coding segments (introns) and transcriptional regulatory sequences. cDNA can also contain untranslated regions (UTRs) that are responsible for translational control in the corresponding RNA molecule. cDNA is synthesized in the laboratory by reverse transcription from messenger RNA extracted from cells.

DNA (deoxyribonucleic acid): A long chain polymer which comprises the genetic material of most living organisms (some viruses have genes comprising ribonucleic acid (RNA)). The repeating units in DNA polymers are four different nucleotides, each of which comprises one of the four bases, adenine, guanine, cytosine and thymine bound to a deoxyribose sugar to which a phosphate group is attached. Triplets of nucleotides (referred to as codons) code for each amino acid in a polypeptide. The term codon is also used for the corresponding (and complementary) sequences of three nucleotides in the mRNA into which the DNA sequence is transcribed.

Unless otherwise specified, any reference to a DNA molecule is intended to include the reverse complement of that DNA molecule. Except where single-strandedness is required by the text herein, DNA molecules, though written to depict only a single strand, encompass both strands of a double-stranded DNA molecule. Thus, a reference to the nucleic acid molecule that encodes a specific protein, or a fragment thereof, encompasses both the sense strand and its reverse complement. Thus, for instance, it is appropriate to generate probes or primers from the reverse complement sequence of the disclosed nucleic acid molecules.

Deletion: The removal of a sequence of DNA, the regions on either side being joined together.

Effective amount of a compound: A quantity of compound sufficient to achieve a desired effect in a subject being treated. For instance, this can be the amount necessary to decrease the size of a tumor in a subject. In general, this amount will be sufficient to monitor the decrease in the size of a tumor in some measurable way, such as by observation, palpitation, contrast radiography, MRI, or PET scan.

An effective amount of a compound can be administered in a single dose, or in several doses, for example daily, during a course of treatment. However, the effective amount of the compound will be dependent on the compound applied, the subject being treated, the severity and type of the affliction, and the manner of administration of the compound.

The general term "administering to the subject" is understood to include all animals (e.g. humans, apes, dogs, cats, horses, and cows) that have or may develop a tumor.

Encode: A polynucleotide is said to "encode" a polypeptide if, in its native state or when manipulated by methods well known to those skilled in the art, it can be transcribed and/or translated to produce the mRNA for and/or the polypeptide or a fragment thereof. The anti-sense strand is the complement of such a nucleic acid, and the encoding sequence can be deduced therefrom.

Functional fragments and variants of a polypeptide: Included are those fragments and variants that maintain one or more functions of the parent polypeptide. It is recognized that the gene or cDNA encoding a polypeptide can be considerably mutated without materially altering one or more the polypeptide's functions. First, the genetic code is well-known to be degenerate, and thus different codons encode the same amino acids. Second, even where an amino acid substitution is introduced, the mutation can be conservative and have no material impact on the essential functions of a protein. See Stryer, Biochemistry 3rd Ed., (c) 1988. Third, part of a polypeptide chain can be deleted without impairing or eliminating all of its functions. Fourth, insertions or additions can be made in the polypeptide chain for example, adding epitope tags, without impairing or eliminating its functions (Ausubel et al., 1997). Other modifications that can be made without materially impairing one or more functions of a polypeptide include, for example, in vivo or in vitro chemical and biochemical modifications or the incorporation of unusual amino acids. Such modifications include, for example, acetylation, carboxylation, phosphorylation, glycosylation, ubiquination, labeling, e.g., with radionucleides, and various enzymatic modifications, as will be readily appreciated by those well skilled in the art. A variety of methods for labeling polypeptides and labels useful for such purposes are well known in the art, and include radioactive isotopes such as $^{32}P$, ligands which bind to or are bound by labeled specific binding partners (e.g., antibodies), fluorophores, chemiluminescent agents, enzymes, and antiligands. Functional fragments and variants can be of varying length. For example, some fragments have at least 10, 25, 50, 75, 100, or 200 amino acid residues.

A functional fragment or variant of p28ING5 is defined herein as a polypeptide which is capable of having p28ING5 tumor suppressor activity. It includes any polypeptide six or more amino acid residues in length which is capable of having p28ING5 tumor suppressor activity.

Heterologous: A type of sequence that is not normally (i.e. in the wild-type sequence) found adjacent to a second sequence. In one embodiment, the sequence is from a different genetic source, such as a virus or organism, than the second sequence.

Hybridization: Oligonucleotides and their analogs hybridize by hydrogen bonding, which includes Watson-Crick, Hoogsteen or reversed Hoogsteen hydrogen bonding, between complementary bases. Generally, nucleic acid consists of nitrogenous bases that are either pyrimidines (cytosine (C), uracil (U), and thymine (T)) or purines (adenine (A) and guanine (G)). These nitrogenous bases form hydrogen bonds between a pyrimidine and a purine, and the bonding of the pyrimidine to the purine is referred to as base pairing. More specifically, A will hydrogen bond to T or U, and G will bond to C. Complementary refers to the base pairing that occurs between to distinct nucleic acid sequences or two distinct regions of the same nucleic acid sequence.

Specifically hybridizable and specifically complementary are terms that indicate a sufficient degree of complementarity such that stable and specific binding occurs between the oligonucleotide (or its analog) and the DNA or RNA target. The oligonucleotide or oligonucleotide analog need not be 100% complementary to its target sequence to be specifically hybridizable. An oligonucleotide or analog is specifically hybridizable when binding of the oligonucleotide or analog to the target DNA or RNA molecule interferes with the normal function of the target DNA or RNA, and there is a sufficient degree of complementarity to avoid non-specific binding of the oligonucleotide or analog to non-target sequences under conditions where specific binding is desired, for example under physiological conditions in the case of in vivo assays or systems. Such binding is referred to as specific hybridization.

Hybridization conditions resulting in particular degrees of stringency will vary depending upon the nature of the hybridization method of choice and the composition and length of the hybridizing nucleic acid sequences. Generally, the temperature of hybridization and the ionic strength (especially the $Na^+$ concentration) of the hybridization buffer will determine the stringency of hybridization, though waste times also influence stringency. Calculations regarding hybridization conditions required for attaining particular degrees of stringency are discussed by Sambrook et al. (ed.), *Molecular Cloning: A Laboratory Manual*, 2nd ed., vol. 1-3, Cold Spring Harbor Laboratory Press, Cold Spring Harbor, N.Y., 1989, chapters 9 and 11, herein incorporated by reference.

The following is an exemplary set of hybridization conditions and is not meant to be limiting.

Very High Stringency (Detects Sequences that Share 90% Sequence Identity)

| Hybridization: | 5x SSC at 65° C. for 16 hours |
|---|---|
| Wash twice: | 2x SSC at room temperature (RT) for 15 minutes each |
| Wash twice: | 0.5x SSC at 65° C. for 20 minutes each |

High Stringency (Detects Sequences that Share 80% Sequence Identity or Greater)

| Hybridization: | 5x-6x SSC at 65° C.-70° C. for 16-20 hours |
|---|---|
| Wash twice: | 2x SSC at RT for 5-20 minutes each |
| Wash twice: | 1x SSC at 55° C.-70° C. for 30 minutes each |

Low Stringency (Detects Sequences that Share Greater than 50% Sequence Identity)

| Hybridization: | 6x SSC at RT to 55° C. for 16-20 hours |
|---|---|
| Wash at least twice: | 2x-3x SSC at RT to 55° C. for 20-30 minutes each. |

Alternative conditions for hybridization, using the Hybrizol I system (Oncor) are shown in the Examples.

ING (INhibitor of Growth): A family of tumor suppressor nucleic acids or polypeptides. Members include ING I, which has three alternatively spliced forms: p47ING1a, p33ING1b, p24ING1c, and ING2. ING tumor suppressors are involved in the regulation of cell growth and proliferation as well as the control of senescence, apoptosis, and anchorage-dependent growth. Disclosed herein is a new member of the family, p28ING5. p28ING5 refers to nucleic acids which encode a protein of approximately 28 kDa p28ING5 is a nuclear protein, and is concentrated at the periphery of the nucleus. The term p28ING5 therefore refers to polymorphic variants, alleles, interspecies homologues, and mutants thereof. Mutants of p28ING5 genes and cDNAs include nonsense, missense, and null mutants and can be genetically engineered or found naturally in tumor cells. The p28ING5 polypeptides encoded by the mutant genes and cDNAs can be truncated, elongated, or contain amino acid substitutions, deletions or insertions. Upstream gene regulatory sequences or intron/exon splice site mutations can abrogate the expression of p28ING5.

Injectable composition: A pharmaceutically acceptable fluid composition including at least one active ingredient. The active ingredient is usually dissolved or suspended in a physiologically acceptable carrier, and the composition can additionally include minor amounts of one or more non-toxic auxiliary substances, such as emulsifying agents, preservatives, and pH buffering agents and the like. Such injectable compositions that are useful for use with the provided nucleotides and proteins are conventional; appropriate formulations are well known in the art.

Isolated: A biological component (such as a nucleic acid molecule, protein or organelle) that has been substantially separated or purified away from other biological components in the cell of the organism in which the component naturally occurs, ie., other chromosomal and extra-chromosomal DNA and RNA, proteins and organelles. Nucleic acids and proteins that have been isolated include nucleic acids and proteins purified by standard purification methods. The term also embraces nucleic acids and proteins prepared by recombinant expression in a host cell as well as chemically synthesized nucleic acids.

Labeled: A biomolecule attached covalently or noncovalently to a detectable label or reporter molecule. Typical labels include radioactive isotopes, enzyme substrates, cofactors, ligands, chemiluminescent or fluorescent agents, haptens, and enzymes. Methods for labeling and guidance in the choice of labels appropriate for various purposes are discussed, e.g., in Sambrook et al., *Molecular Cloning: A Laboratory Manual*, CSHL, New York, 1989 and Ausubel et al., *Current Protocols in Molecular Biology*, Greene Publ. Assoc. and Wiley-Intersciences, 1998. For example, ATP can be labeled in any one of its three phosphate groups with radioisotopes such as $^{32}P$ or $^{33}P$, or in its sugar moiety with a radioisotopes such as $^{35}S$.

Mammal: This term includes both human and non-human mammals. Similarly, the term subject includes both human and veterinary subjects.

Modulator: An agent that increases or decreases (modulates) the activity of a protein as measured by the change in an experimental parameter. A modulator can be essentially any compound, such as a chemotherapeutic agent, a polypeptide, a hormone, a nucleic acid, a sugar, a lipid and the like.

Neoplasm: An abnormal mass of tissue resulting from excessive cell division that is uncontrolled and progressive, also called a tumor. Neoplasms are either begin (neither infiltrative nor cancerous) or malignant (invasive). A neoplastic cell is a cell derived from a neoplasm.

Nucleotide: This term includes, but is not limited to, a monomer that includes a base linked to a sugar, such as a pyrimidine, purine or synthetic analogs thereof, or a base linked to an amino acid, as in a peptide nucleic acid (PNA). A nucleotide is one monomer in a polynucleotide. A nucleotide sequence refers to the sequence of bases in a polynucleotide.

Oligonucleotide: A plurality of joined nucleotides joined by native phosphodiester bonds, between about 6 and about 300 nucleotides in length. An oligonucleotide analog refers to moieties that function similarly to oligonucleotides but have non-naturally occurring portions. For example, oligonucleotide analogs can contain non-naturally occurring portions, such as altered sugar moieties or inter-sugar linkages, such as a phosphorothioate oligodeoxynucleotide. Functional analogs of naturally occurring polynucleotides can bind to RNA or DNA, and include peptide nucleic acid (PNA) molecules.

Particular oligonucleotides and oligonucleotide analogs can include linear sequences up to about 200 nucleotides in length, for example a sequence (such as DNA or RNA) that is at least 6 bases, for example at least 8, 10, 15, 20, 25, 30, 35, 40, 45, 50, 100 or even 200 bases long, or from about 6 to about 50 bases, for example about 10-25 bases, such as 12, 15 or 20 bases.

Operably linked: A first nucleic acid sequence is operably linked with a second nucleic acid sequence when the first nucleic acid sequence is placed in a functional relationship with the second nucleic acid sequence. For instance, a promoter is operably linked to a coding sequence if the promoter affects the transcription or expression of the coding sequence. Generally, operably linked DNA sequences are contiguous and, where necessary to join two protein-coding regions, in the same reading frame.

Open reading frame: A series of nucleotide triplets (codons) coding for amino acids without any internal termination codons. These sequences are usually translatable into a peptide.

Ortholog: Two nucleic acid or amino acid sequences are orthologs of each other if they share a common ancestral sequence and diverged when a species carrying that ancestral sequence split into two species. Orthologous sequences are also homologous sequences.

Parenteral: Administered outside of the intestine, e.g., not via the alimentary tract. Generally, parenteral formulations are those that will be administered through any possible mode except ingestion. This term especially refers to injections, whether administered intravenously, intrathecally, intramuscularly, intraperitoneally, or subcutaneously, and various surface applications including intranasal, intradermal, and topical application, for instance.

Peptide Nucleic Acid (PNA): An oligonucleotide analog with a backbone comprised of monomers coupled by amide (peptide) bonds, such as amino acid monomers joined by peptide bonds.

Pharmaceutically acceptable carriers: The pharmaceutically acceptable carriers useful with the compositions provided herein are conventional. Martin, *Remington's Pharmaceutical Sciences*, published by Mack Publishing Co., Easton, Pa., 19th Edition, 1995, describes compositions and formulations suitable for pharmaceutical delivery of the nucleotides and proteins herein disclosed.

In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. For solid compositions (e.g., powder, pill, tablet, or capsule forms), conventional non-toxic solid carriers can include, for example, pharmaceutical grades of mannitol, lactose, starch, or magnesium stearate. In addition to biologically-neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

Pharmaceutical agent: A chemical compound or composition capable of inducing a desired therapeutic or prophylactic effect when properly administered to a subject or a cell. Incubating includes exposing a target to an agent for a sufficient period of time for the agent to interact with a cell. Contacting includes incubating an agent in solid or in liquid form with a cell.

Polypeptide: A polymer in which the monomers are amino acid residues which are joined together through amide bonds. When the amino acids are alpha-amino acids, either the L-optical isomer or the D-optical isomer can be used, the L-isomers being preferred. The term polypeptide or protein as used herein encompasses any amino acid sequence and includes modified sequences such as glycoproteins. The term polypeptide is specifically intended to cover naturally occurring proteins, as well as those that are recombinantly or synthetically produced.

The term polypeptide fragment refers to a portion of a polypeptide which exhibits at least one useful epitope. The phrase functional fragments of a polypeptide refers to all fragments of a polypeptide that retain an activity, or a measurable portion of an activity, of the polypeptide from which the fragment is derived. Fragments, for example, can vary in size from a polypeptide fragment as small as an epitope capable of binding an antibody molecule to a large polypeptide capable of participating in the characteristic induction or programming of phenotypic changes within a cell. An epitope is a region of a polypeptide capable of binding an immunoglobulin generated in response to contact with an antigen. Thus, smaller peptides containing the biological activity of insulin, or conservative variants of the insulin, are thus included as being of use.

The term soluble refers to a form of a polypeptide that is not inserted into a cell membrane.

The term substantially purified polypeptide as used herein refers to a polypeptide that is substantially free of other proteins, lipids, carbohydrates or other materials with which it is naturally associated. In one embodiment, the polypeptide is at least 50%, for example at least 80% free of other proteins, lipids, carbohydrates or other materials with which it is naturally associated. In another embodiment, the polypeptide is at least 90% free of other proteins, lipids, carbohydrates or other materials with which it is naturally associated. In yet another embodiment, the polypeptide is at least 95% free of other proteins, lipids, carbohydrates or other materials with which it is naturally associated.

Conservative amino acid substitution tables providing functionally similar amino acids are well known to one of ordinary skill in the art. The following six groups are examples of amino acids that are considered to be conservative substitutions for one another:

1) Alanine (A), Serine (S), Threonine (T);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V); and
6) Phenylalanine (F), Tyrosine (Y), Tryptophan (W).

Variations in the cDNA sequence that result in amino acid changes, whether conservative or not, are usually minimized in order to preserve the functional and immunologic identity of the encoded protein. For example, the functional identity of the protein can be maintained if amino acid substitutions are introduced in regions outside of the conserved domains of the protein, where amino acid substitutions are less likely to affect protein function. Examples of conserved domains include nuclear localization signals and a plant homeo domain. Alternatively, the functional identity of the protein can be altered if amino acid substitutions are introduced in regions within the conserved domains of the protein. The immunologic identity of the protein may be assessed by determining whether it is recognized by an antibody; a variant that is recognized by such an antibody is immunologically conserved. Any cDNA sequence variant will preferably introduce no more than twenty, and preferably fewer than ten amino acid substitutions into the encoded polypeptide. Variant amino acid sequences may, for example, be 80%, 90% or even 95% or 98% identical to the native amino acid sequence. Programs and algorithms for determining percentage identity can be found at the NCBI website.

Polymorphism: Variant in a sequence of a gene. Polymorphisms can be those variations (nucleotide sequence differences) that, while having a different nucleotide sequence, produce functionally equivalent gene products, such as those variations generally found between individuals, different ethnic groups, geographic locations. The term polymorphism also encompasses variations that produce gene products with altered function, i.e., variants in the gene sequence that lead to gene products that are not functionally equivalent. This term also encompasses variations that produce no gene product, an inactive gene product, or increased gene product. The term polymorphism may be used interchangeably with allele or mutation, unless context clearly dictates otherwise.

Polymorphisms can be referred to, for instance, by the nucleotide position at which the variation exists, by the change in amino acid sequence caused by the nucleotide variation, or by a change in some other characteristic of the nucleic acid molecule that is linked to the variation (e.g., an alteration of a secondary structure such as a stem-loop, or an alteration of the binding affinity of the nucleic acid for associated molecules, such as polymerases, RNases, and so forth).

Preventing or treating a disease: Preventing a disease refers to inhibiting the partial or full development or progression of a disease, for example in a person who is known to have a predisposition to a disease. An example of a person with a known predisposition is someone with a history of diabetes in the family, or who has been exposed to factors that predispose the subject to a condition, such as lupus or rheumatoid arthritis. Treating a disease refers to a therapeutic intervention that ameliorates at least one sign or symptom of a disease or pathological condition, or interferes with a pathophysiological process, after the disease or pathological condition has begun to develop.

Probes and primers: Nucleic acid probes and primers can be readily prepared based on the nucleic acid molecules provided in this disclosure. A probe comprises an isolated nucleic acid attached to a detectable label or reporter molecule. Typical labels include radioactive isotopes, enzyme substrates, co-factors, ligands, chemiluminescent or fluorescent agents, haptens, and enzymes. Methods for labeling and guidance in the choice of labels appropriate for various purposes are discussed, e.g., in Sambrook et at (In *Molecular Cloning: A Laboratory Manual*, CSHL, New York, 1989) and Ausubel et al. (In *Current Protocols in Molecular Biology*, Greene Publ. Assoc. and Wiley-Intersciences, 1992).

Primers are short nucleic acid molecules, preferably DNA oligonucleotides 10 nucleotides or more in length. More preferably, longer DNA oligonucleotides can be about 15, 17, 20, or 23 nucleotides or more in length. Primers can be annealed to a complementary target DNA strand by nucleic acid hybridization to form a hybrid between the primer and the target DNA strand, and then the primer extended along the target DNA strand by a DNA polymerase enzyme. Primer pairs can be used for amplification of a nucleic acid sequence, eg., by the polymerase chain reaction (PCR) or other nucleic-acid amplification methods known in the art.

Methods for preparing and using probes and primers are described, for example, in Sambrook et al. (In *Molecular Cloning: A Laboratory Manual*, CSHL, New York, 1989), Ausubel et al. (In *Current Protocols in Molecular Biology*, Greene Publ. Assoc. and Wiley-Intersciences, 1998), and Innis et al (*PCR Protocols, A Guide to Methods and Applications*, Academic Press, Inc., San Diego, Calif., 1990). PCR primer pairs can be derived from a known sequence, for example, by using computer programs intended for that purpose such as Primer (Version 0.5, © 1991, Whitehead Institute for Biomedical Research, Cambridge, Mass.). One of ordinary skill in the art will appreciate that the specificity of a particular probe or primer increases with its length. Thus, for example, a primer comprising 30 consecutive nucleotides of p28ING5 encoding nucleotide will anneal to a target sequence, such as a p28ING5 gene homolog from the gene family contained within a human genomic DNA library, with a higher specificity than a corresponding primer of only 15 nucleotides. Thus, in order to obtain greater specificity, probes and primers can be selected that comprise at least 17, 20, 23, 25, 30, 35, 40, 45, 50 or more consecutive nucleotides of p28ING5 nucleotide sequences.

The disclosure thus includes isolated nucleic acid molecules that comprise specified lengths of the disclosed p28ING5 cDNA sequences. Such molecules can comprise at least 17, 20, 23, 25, 30, 35, 40, 45 or 50 consecutive nucleotides of these sequences, and can be obtained from any region of the disclosed sequences. By way of example, the p28ING5 cDNA sequences can be apportioned into halves, thirds or quarters based on sequence length, and the isolated nucleic acid molecules can be derived from the first or second halves of the molecules, from any of the three thirds or any of the four quarters. By way of example, the human p28ING5 cDNA, ORF, coding sequence and gene sequences can be apportioned into about halves, thirds or quarters based on sequence length, and the isolated nucleic acid molecules (e.g., oligonucleotides) can be derived from the first or second halves of the molecules, from any of the three thirds, or any of the four quarters. The cDNA also could be divided into smaller regions, e.g. about eighths, sixteenths, twentieths, fiftieths and so forth, with similar effect.

Another mode of division, provided by way of example is to divide a p28ING5 encoding sequence based on the regions of the sequence that are relatively more or less homologous to the classic ING sequence. Thus, nucleic acid molecules, for instance to be used as hybridization probe molecules, may be selected from the N-terminal region (e.g., about residues 3-360, or a fragment thereof) of the human p28ING5-cDNA shown in SEQ ID NO: 1, or from a C-terminal region (e.g., about residues 361-722, or a fragment thereof). Alternatively, nucleic acid molecules can be selected from sequences that encode conserved domains, such as the PHD (see FIG. 12).

Another mode of division is to select the 5' (upstream) and/or 3' (downstream) region associated with a p28ING5 gene.

Protein: A biological molecule expressed by a gene and comprised of amino acids.

Purified: The term purified does not require absolute purity; rather, it is intended as a relative term. Thus, for example, a purified protein preparation is one in which the protein referred to is more pure than the protein in its natural environment within a cell.

Recombinant: A nucleic acid that has a sequence that is not naturally occurring or has a sequence that is made by an artificial combination of two otherwise separated segments of sequence. This artificial combination can be accomplished by chemical synthesis or, more commonly, by the artificial manipulation of isolated segments of nucleic acids, e.g., by genetic engineering techniques.

Ribozyme: Synthetic RNA molecules that possess highly specific endoribonuclease activity. The production and use of ribozymes are disclosed in U.S. Pat. No. 4,987,071 to Cech and U.S. Pat. No. 5,543,508 to Haselhoff. The inclusion of ribozyme sequences within antisense RNAs can be used to confer RNA cleaving activity on the antisense RNA, such that endogenous mRNA molecules that bind to the antisense RNA are cleaved, which in turn leads to an enhanced antisense inhibition of endogenous gene expression.

Sequence identity: The similarity between two nucleic acid sequences, or two amino acid sequences, is expressed in terms of the similarity between the sequences, otherwise referred to as sequence identity: Sequence identity is frequently measured in terms of percentage identity (or similarity or homology); the higher the percentage, the more similar the two sequences are. Homologs or orthologs of the p28ING5 protein, and the corresponding cDNA sequence, will possess a relatively high degree of sequence identity when aligned using standard methods. This homology will be more significant when the orthologous proteins or cDNAs are derived from species which are more closely related (e.g., human and chimpanzee sequences), compared to species more distantly related (e.g., human and *C. elegans* sequences). In several embodiments, homologous sequences include nucleic acid residues 1-39 or 723-1068 of SEQ ID NO: 1.

Typically, p28ING5 orthologs are at least 50%, at least 70%, at least 75%, at least 80%, at least 85%, at least 90%, at least 91%, at least 93%, at least 95%, or at least 98% identical at the nucleotide level and at least 50%, at least 70%, at least 75%, at least 80%, at least 85%, at least 90%, at least 91%, at least 93%, at least 95%, or at least 98% identical at the amino acid level when comparing p28ING5 to an orthologous p28ING5.

Methods of alignment of sequences for comparison are well known in the art. Various programs and alignment algorithms are described in: Smith & Waterman *Adv. Appl. Math.* 2: 482, 1981; Needleman & Wunsch *J. Mol. Biol.* 48: 443, 1970; Pearson & Lipman *Proc. Natl. Acad. Sci. USA* 85: 2444, 1988; Higgins & Sharp *Gene*, 73: 237-244, 1988; Higgins & Sharp *CABIOS* 5: 151-153, 1989; Corpet et al. *Nuc. Acids Res.* 16, 10881-10890, 1988; Huang et al. *Computer Appls. in the Biosciences* 8, 155-165, 1992; and Pearson et al. Meth. Mol. Bio. 24, 307-331, 1994. Altschul et al. (*J. Mol. Biol.* 215:403-410, 1990) present a detailed consideration of sequence alignment methods and homology calculations.

The NCBI Basic Local Alignment Search Tool (BLAST) (Altschul et al. *J. Mol. Biol.* 215:403-410, 1990) is available from several sources, including the National Center for Biotechnology Information (NCBI, Bethesda, Md.) and on the Internet, for use in connection with the sequence analysis programs blastp, blastn, blastx, tblastn and tblastx. It can be accessed at the NCBI website, together with a description of how to determine sequence identity using this program.

An alternative indication that two nucleic acid molecules are closely related is that the two molecules hybridize to each other under stringent conditions. Stringent conditions are sequence-dependent and are different under different environmental parameters. Generally, stringent conditions are selected to be about 5° C. to 20° C. lower than the thermal melting point ($T_m$) for the specific sequence at a defined ionic strength and pH. The $T_m$ is the temperature (under defined ionic strength and pH) at which 50% of the target sequence remains hybridized to a perfectly matched probe or complementary strand. Conditions for nucleic acid hybridization and calculation of stringencies can be found in Sambrook et al. (1989) *Molecular Cloning: A Laboratory Manual*, CSHL, New York and Tijssen (1993) *Laboratory Techniques in Biochemistry and Molecular Biology—Hybridization with Nucleic Acid Probes* Part I, Chapter 2, Elsevier, New York. Nucleic acid molecules that hybridize under stringent conditions to a human p28ING5 gene sequence will typically hybridize to a probe based on either an entire human p28ING5 gene or selected portions of the gene under wash conditions of 2×SSC at 50° C. A more detailed discussion of hybridization conditions is presented below.

Nucleic acid sequences that do not show a high degree of identity can nevertheless encode similar amino acid sequences, due to the degeneracy of the genetic code. It is understood that changes in nucleic acid sequence can be made using this degeneracy to produce multiple nucleic acid molecules that all encode substantially the same protein.

Specific binding agent: An agent that binds substantially only to a defined target. Thus a p28ING5 protein-specific binding agent binds substantially only the p28ING5 protein. As used herein, the phrase p28ING5 protein-specific binding agent includes anti-p28ING5 protein antibodies and other agents (such as soluble receptors) that bind substantially only to the p28ING5 protein.

Anti-p28ING5 protein antibodies can be produced using standard procedures described in a number of texts, including Harlow and Lane (Antibodies, A Laboratory Manual, CSHL, New York, 1988). The determination that a particular agent binds substantially only to the p28ING5 protein can readily be made by using or adapting routine procedures. One suitable in vitro assay makes use of the Western blotting procedure (described in many standard texts, including Harlow and Lane, *Antibodies, A Laboratory Manual*, CSHL, New York, 1988). Western blotting can be used to determine that a given p28ING5 protein binding agent, such as an anti-p28ING5 protein monoclonal antibody, binds substantially only to the p28ING5 protein.

A phosphospecific binding agent specifically binds to a peptide containing a phosphorylated residue.

Shorter fragments of antibodies can also serve as specific binding agents. For instance, Fabs, Fvs, and single-chain Fvs (SCFvs) that bind to p28ING5 would be p28ING5-specific binding agents. These antibody fragments are defined as follows: (I) Fab, the fragment which contains a monovalent antigen-binding fragment of an antibody molecule produced by digestion of whole antibody with the enzyme papain to yield an intact light chain and a portion of one heavy chain; (2) Fab', the fragment of an antibody molecule obtained by treating whole antibody with pepsin, followed by reduction, to yield an intact light chain and a portion of the heavy chain; two Fab' fragments are obtained per antibody molecule; (3) $(Fab')_2$, the fragment of the antibody obtained by treating whole antibody with the enzyme pepsin without subsequent reduction; (4) $F(ab')_2$, a dimer of two Fab' fragments held together by two disulfide bonds; (5) Fv, a genetically engineered fragment containing the variable region of the light chain and the variable region of the heavy chain expressed as two chains; and (6) single chain antibody (SCA), a genetically engineered molecule containing the variable region of the light chain, the variable region of the heavy chain, linked by a suitable polypeptide linker as a genetically fused single chain molecule. Methods of making these fragments are routine.

Subject: Living multi-cellular vertebrate organisms, a category that includes both human and non-human mammals.

Target sequence: "Target sequence" is a portion of ssDNA, dsDNA or RNA that, upon hybridization to a therapeutically effective oligonucleotide or oligonucleotide analog, results in the inhibition of expression. For example, hybridization of therapeutically effectively oligonucleotide to a p28ING5 target sequence results in inhibition of p28ING5 expression. Either an antisense or a sense molecule can be used to target a portion of dsDNA, since both will interfere with the expression of that portion of the dsDNA. The antisense molecule can bind to the plus strand, and the sense molecule can bind to the minus strand. Thus, target sequences can be ssDNA, dsDNA, and RNA.

Test compound: A test compound can be essentially any compound, such as a chemotherapeutic, a polypeptide, a hormone, a nucleic acid, a sugar, a lipid and the like.

Transfected: A process by which a nucleic acid molecule is introduced into cell, for instance by molecular biology techniques, resulting in a transfected cell. As used herein, the term transfection encompasses all techniques by which a nucleic acid molecule might be introduced into such a cell, including transduction with viral vectors, transfection with plasmid vectors, and introduction of DNA by electroporation, lipofection, and particle gun acceleration.

Tumor: A neoplasm that may be either malignant or non-malignant. Tumors of the same tissue type are primary tumors originating in a particular organ (such as breast, prostate, bladder or lung). Tumors of the same tissue type may be divided into tumor of different sub-types (a classic example being bronchogenic carcinomas (lung tumors) which can be an adenocarcinoma, small cell, squamous cell, or large cell tumor). Breast cancers can be divided histologically into scirrhous, infiltrative, papillary, ductal, medullary and lobular.

Tumor suppressor: A nucleic acid or the polypeptide it encodes, that in its wildtype form has the ability to suppress, prevent, or decrease uncontrolled cell growth and or cell/division. Tumor suppressor genes encode proteins that inhibit progression through the cell cycle thereby inhibiting cell growth and/or cell division. When DNA damage is detected in a cell, tumor suppressors prevent the cell from continuing to multiply until the damaged DNA is repaired. Alternatively, if the DNA cannot be repaired, they may signal the cell to undergo apoptosis (programmed cell death) in order prevent the damaged DNA from being passed on to the daughter cells. Tumor suppressors therefore play an important role in preventing the onset of uncontrolled cell growth, or neoplasia. Examples of tumor suppressors are p53, RB and members of the ING family.

Vector: A nucleic acid molecule as introduced into a host cell, thereby producing a transfected host cell. Recombinant DNA vectors are vectors having recombinant DNA. A vector can include nucleic acid sequences that permit it to replicate in a host cell, such as an origin of replication. A vector can also include one or more selectable marker genes and other genetic elements known in the art. Viral vectors are recombinant DNA vectors having at least some nucleic acid sequences derived from one or more viruses.

Unless otherwise explained, all technical and scientific terms used herein have the same meaning as commonly understood by one of ordinary skill in the art to which this invention belongs. The singular terms "a,", "an," and "the" include plural referents unless context clearly indicates otherwise. Similarly, the word "or" is intended to include "and" unless the context clearly indicates otherwise. Hence "comprising A or B" means including A, or B, or A and B. It is further to be understood that all base sizes or amino acid sizes, and all molecular weight or molecular mass values, given for nucleic acids or polypeptides are approximate, and are provided for description. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including explanations of terms, will control. In addition, the materials, methods, and examples are illustrative only and not intended to be limiting.

III. Description of Several Specific Embodiments

Provided herein are p28ING5 tumor suppressor proteins having a sequence as shown in SEQ ID NO: 2, or at least amino acid residues 1-13 and 241-356 of SEQ ID NO: 2, or a sequence having one or more conservative substitutions in SEQ ID NO: 2. Also provided are recombinant polynucleotides encoding such p28ING5 proteins. Representative examples of such polynucleotides have a sequence as shown in SEQ ID NO: 1, or at least the nucleotide residues 1-39, 723-1068, or 1-39 and 723-1068 of SEQ ID NO: 1, or a conservative variant thereof.

Recombinant DNA vectors comprising the disclosed DNA molecules, and transgenic host cells containing such recombinant vectors, are also provided. In specific embodiments, a p28ING5 recombinant polynucleotide is operably linked to a promoter sequence in either the sense or antisense orientation, relative to the promoter. In other embodiments, cells are transfected with the p28ING5 recombinant polynucleotide and promoter sequences. In still other embodiments, the p28ING5 recombinant polynucleotide and promoter sequences are placed in recombinant vectors and the recombinant vectors containing these sequences are transfected into cells. Disclosed embodiments also include transgenic animals, particularly non-human animals, that over- or under-express a p28ING5 protein, or over- or under-express fragments or variants of p28ING5.

Further embodiments are isolated oligonucleotides of at least 10 nucleotides in length, which specifically hybridize under stringent conditions to nucleotide residues 1-39 or 723-1068 of SEQ ID NO: 1. Other embodiments provide isolated oligonucleotides of at least 10 contiguous nucleotides having a sequence found in nucleotides 1-39 or 723-1068 of SEQ ID NO: 1, or a variant thereof, which oligonucleotides hybridize to SEQ ID NO: 1 under high stringency conditions. In still other embodiments, such isolated oligonucleotides are of at least 20 contiguous nucleotides in length, or at least 30, 40, 50, 60, or 100 nucleotides in length.

Also provided are oligonucleotides of at least 10 contiguous nucleotides that hybridize with nucleotides 1-39 of SEQ ID NO: 1 under wash conditions of 65° C., 0.5×SSC and 0.1% SDS, or 55° C., 2.0×SSC and 0.1% SDS, and oligonucleotides of at least 10 contiguous nucleotides that hybridize with nucleotides 723-1068 of SEQ ID NO: 1 under wash conditions of 65° C., 0.5×SSC and 0.1% SDS, or 55° C., 2.0×SSC and 0.1% SDS.

This disclosure further provides methods of inhibiting cellular proliferation, which methods involve transfecting a cell with an expression vector containing a promoter operably linked to a nucleic acid having a sequence as shown in SEQ ID NO: 1, or a nucleic acid having a sequence with a conservative substitution of SEQ ID NO: 1, or sharing a nucleic acid sequence with at least nucleotides 1-39 and 723-1068 of SEQ ID NO: 1.

Also provided are methods of inhibiting cellular proliferation by contacting a cell with a protein having a sequence as shown in SEQ ID NO: 2, a conservative substitution of SEQ ID NO: 2, or at least amino acid residues 1-13 and 241-356 of SEQ ID NO: 2.

Still other embodiments are methods of enhancing cellular proliferation by transfecting a cell with an expression vector containing a p28ING5 recombinant polynucleotide operably linked to a promoter in an antisense orientation, relative to the promoter. In a specific example of such method, the expression vector transfected into a cell contains a nucleic acid having a sequence as shown in SEQ ID NO: 1, or a conservative substitution thereof, operably linked to a promoter sequence in antisense orientation relative to the promoter.

Specific binding agents that specifically bind an epitope of the protein encoded by the amino acid sequence of SEQ ID NO: 2 are also provided.

The disclosure further provides methods of screening for an agent that modulates p28ING5 tumor suppressor activity. Such methods involve transfecting a cell with an expression vector containing a nucleic acid molecule having a sequence as shown in SEQ ID NO: 1, or a conservative substitution thereof, which nucleic acid molecule is operably linked to a promoter sequence. Examples of such methods further involve contacting the transfected cell with a test agent and then detecting a change in the level of expression of a p28ING5 protein in the cell. In particular embodiments of these methods, a change in the level is indicative that the test agent is an agent that modulates the expression of the p28ING5 tumor suppressor protein.

The disclosure also provides a method of detecting a p28ING5 tumor suppressor protein in a biological sample. The method involves amplifying a nucleotide sequence as shown in SEQ ID NO: 1 (though not necessarily the entire sequence shown in SEQ ID NO: 1), or a conservative substitution thereof, with two or more oligonucleotide primers that specifically bind to sequences within SEQ ID NO: 1, then detecting the presence and/or level of an amplified product.

This disclosure also provides methods of detecting or diagnosing the presence of a tumor in a subject (for instance, a human subject). Examples of such methods involve amplifying a nucleic acid molecule having a sequence as shown in SEQ ID NO: 1, or a conservative substitution thereof, in a sample using two or more oligonucleotide primers that specifically bind nucleotide residues of SEQ ID NO: 1, then detecting an amplified product, if one is produced. In specific examples of such methods, the absence of an amplified product is indicative of the presence of a tumor in a subject. Examples of provided methods of detecting or diagnosing the presence of a tumor in a subject further involve reverse transcribing a mRNA having a sequence as shown in SEQ ID NO: 1, or a conservative substitution thereof, into the corresponding p28ING5 cDNA before being amplified. Specific representative methods further involve detecting a change in the level of the amplified product compared to a second sample (e.g., by Southern blot analysis, quantitative polymerase chain reaction or semi-quantitative polymerase chain reaction), or detecting a mutation in the amplified product (e.g., by sequencing, chemical cleavage, denaturing gradient gel electrophoresis, or hybridization with allele specific oligonucleotides).

In specific provided embodiments, the tumor is a breast tumor, a lung tumor, a colon tumor, a pancreatic tumor, a liver tumor, a brain tumor, a skin tumor, a prostate tumor, a testicular tumor, an ovarian tumor, a stomach tumor, or a tumor of the blood. Similarly, in specific provided embodiments, the sample is blood, a blood product, urine, saliva, a tissue biopsy, a surgical specimen, an amniocentesis sample, or autopsy material.

The disclosure also provides a method of treating a neoplasm by contacting a neoplastic cell with a protein having an amino acid sequence as set forth in SEQ ID NO: 2, or a conservative substitution thereof, or a fragment of such a protein.

This disclosure further provides kits, including in vitro assay kits for determining whether or not a subject has a biological condition associated with p28ING5 expression (for instance, conditions that are indicated by an over- or under-abundance of p28ING5 expression). Specific examples of such kits provide one or more agents to be used in a method to detect an underabundance of p28ING5 protein in a sample of tissue and/or body fluids from the subject (for instance, a human subject). In one specific embodiment, the kit contains a container with an antibody specific for p28ING5 protein as well as instructions for using the kit. By way of example, the instructions in some kits indicate steps for performing a method to detect the presence of p28ING5 protein in the sample and for analyzing data generated by the method. In other embodiments, the instructions indicate that an underabundance of p28ING5 protein in the sample indicates that the individual has the biological condition.

Also provided are in vitro amplification assay kits for determining whether or not a subject has a biological condition associated with a p28ING5 nucleic acid, for instance an over- or under-abundance of a p28 ING5 nucleic acid. Such kits provide one or more reagents for use in a method to detect the presence and/or quantity of a nucleic acid that encodes p28ING5 protein in a sample of tissue and/or body fluids from the subject. Specific examples of such kits contain an in vitro amplification primer (in a container), which can be used to specifically amplify a nucleic acid that encodes p28ING5 protein. Optionally, such kits can also include a size marker (for instance, in a second container), the size marker being the expected size of amplified DNA if the nucleic acid that encodes p28ING5 protein is present in the sample. Examples of these kits further include instructions for using the kit. In one example kit, the instructions indicate steps for performing a method to detect and/or quantify the nucleic acid that encodes p28ING5 protein in the sample; and analyzing data generated by the method. In another example kit, the instructions indicate that the presence of decreased nucleic acid that encodes p28ING5 protein in the sample indicates that the subject has the biological condition.

IV. p28ING5 Nucleic Acids and Proteins

This disclosure provides a p28ING5 tumor suppressor protein and variants thereof, and nucleic acid molecules encoding these proteins, including cDNA sequences. In specific embodiments, these sequences are used for ameliorating, treating, detecting, prognosing, and diagnosing diseases and conditions associated with abnormal p28ING5 expression, such as neoplasia.

A nucleic acid molecule encoding p28ING5, and the corresponding deduced amino acid sequence of p28ING5, are shown in SEQ ID NO: 1. The nucleic acid molecule encodes a protein of 240 amino acids in length (SEQ ID NO: 2; see also FIG. 12). No single published sequence or other reference has been identified that discloses the entire p28ING5 nucleic acid or protein sequence. Two sets of published sequences overlap the p28ING5 nucleic acid or protein sequence. The first set contains sequences that overlap p28ING5 in the 5' (upstream or amino) portion of the molecule. The first sequence, a human EST (GenBank No. BG753113; released in GenBank on May 15, 2001) overlaps nucleotides 5-722 of the p28ING5 open reading frame (ORF) (SEQ ID NO: 1). A second sequence (GenBank No. BG170225, released in GenBank on Feb. 6, 2001), overlaps p28ING5 from the start to position 767. Also included in this set of upstream overlapping molecules are the nucleic acid sequence NM_032329 (identical to p28ING5 through position 682) and the corresponding protein (NP_115705.1, identical to p28ING5 through residue 226). These sequences were both released in the GenBank database on May 19, 2001.

The second set of sequences are those that overlap p28ING5 in the 3' (downstream or carboxy) portion of the molecule. GenBank No. AX147962 (released in GenBank on Jun. 8, 2001) refers to both a nucleotide sequence (SEQ ID NO: 7) and a protein sequence (SEQ ID NO: 8) of PCT application PCT/US00/31698 that was published May 25, 2001. AX147962 overlaps p28ING5 from position 40 to the end of the sequence and the protein encoded by this nucleic acid sequence appears to be identical to p28ING5 from position 16 to the end.

With the provision herein of the sequence of the p28ING5 protein (SEQ ID NO: 2) and cDNA (SEQ ID NO: 1), in vitro nucleic acid amplification (such as polymerase chain reaction (PCR)) may be utilized as a simple method for producing p28ING5 encoding sequences. The following provides representative techniques for preparing cDNA in this manner.

Total RNA is extracted from human cells by any one of a variety of methods well known to those of ordinary skill in the art. Sambrook et al. (In *Molecular Cloning: A Laboratory Manual*, CSHL, New York, 1989) and Ausubel et al. (In *Current Protocols in Molecular Biology*, Greene Publ. Assoc. and Wiley-Intersciences, 1992) provide descriptions of methods for RNA isolation. p28ING5 is expressed in many different human tissues and in cell lines derived from a variety of human tumors. In one embodiment, primary cells are obtained from normal tissues. In another embodiment cells are obtained from neoplastic tissues. In yet another embodiment cell lines, derived from normal or neoplastic tissues, are used as a source of such RNA. The extracted RNA is then used, for example as a template for performing reverse transcription (RT)-PCR amplification of cDNA. Methods and conditions for RT-PCR are described in Kawasaki et al., (In *PCR Protocols, A Guide to Methods and Applications*, Innis et al. (eds.), 21-27, Academic Press, Inc., San Diego, Calif., 1990).

The selection of amplification primers will be made according to the portion(s) of the cDNA that is to be amplified. In one embodiment, primers may be chosen to amplify a segment of a cDNA or, in another embodiment, the entire cDNA molecule. Variations in amplification conditions may be required to accommodate primers and amplicons of differing lengths and composition; such considerations are well known in the art and are discussed for instance in Innis et al. (*PCR Protocols, A Guide to Methods and Applications*, Academic Press, Inc., San Diego, Calif., 1990). By way of example, the coding portion of the human p28ING5 cDNA molecule (approximately 1.07 kb) may be amplified using the following combination of primers:

| | |
|---|---|
| 5'-primer (overlapping the initiation codon):<br>5'-ATG GCG ACC GCC ATG TAC TTG-3'; | (Residues 3-23 of SEQ ID NO: 1) |
| 3'-primer (overlapping the termination codon):<br>5'-CTA CTT CTT CTT CCT CTT TTC-3'. | (Reverse complement of residues 705-725 of SEQ ID NO: 1) |

Similarly, the following set of two primers can be used to amplify A complete provided human p28ING5 cDNA, as shown in SEQ ID NO: 1:

| | |
|---|---|
| 5'-primer:<br>5'-AGA TGG CGA CCG CCA TGT ACT TG-3' | (Residues 1-23 of SEQ ID NO: 1) |
| 3-primer:<br>5'-GCG GCC GCC CTC CGT GGA CC-3'. | (Reverse complement of residues 1048-1068 of SEQ ID NO: 1) |

These primers are illustrative only; one skilled in the art will appreciate that many different primers may be derived from the provided cDNA sequence in order to amplify particular regions of p28ING5 cDNA, as well as the complete sequence of the human p28ING5 cDNA.

Re-sequencing of PCR products obtained by amplification procedures optionally can be performed to facilitate confirmation of the amplified sequence and provide information about natural variation of this sequence in different populations or species. Oligonucleotides derived from the provided p28ING5 sequences may be used in such sequencing methods.

Orthologs of human p28ING5 can be cloned in a similar manner, where the starting material consists of cells taken from a non-human species. In one embodiment, orthologs will generally share at least 65% sequence identity with the disclosed human p28ING5 cDNA. Where the non-human species is more closely related to humans, the sequence identity will in general be greater. In other embodiments, closely related orthologous p28ING5 molecules may share at least 70%, at least 75%, at least 80% at least 85%, at least 90%, at least 91%, at least 93%, at least 95%, or at least 98% sequence identity with the disclosed human nucleotide or amino acid sequences.

Oligonucleotides derived from the human p28ING5 cDNA sequence (e.g., SEQ ID NO: 1), or fragments of this cDNA, are encompassed within the scope of the present disclosure. In one embodiment, such oligonucleotides may comprise a sequence of at least 10 consecutive nucleotides of the p28ING5 nucleic acid sequence. If these oligonucleotides are used with an in vitro amplification procedure (such as PCR), lengthening the oligonucleotides may enhance amplification specificity. Thus, in other embodiments, oligonucleotide primers comprising at least 15, 20, 25, 30, 35, 40, 45, 50, or more consecutive nucleotides of these sequences may be used. These primers for instance may be obtained from any region of the disclosed sequences. By way of example, the human p28ING5 cDNA, ORF and gene sequences may be apportioned into about halves, thirds or quarters based on sequence length, and the isolated nucleic acid molecules (e.g., oligonucleotides) may be derived from the first or second halves of the molecules, from any of the three thirds, or from any of the four quarters. The human p28ING5 cDNA, shown in SEQ ID NO: 1, can be used to illustrate this. The human p28ING5 cDNA is 720 nucleotides in length and so in one specific embodiment, it may be hypothetically divided into about halves (nucleotides 3-360 and 361-722), in another specific embodiment, in about thirds (nucleotides 3-240, 241-482, 482-722) or in yet another specific embodiment, in about quarters (nucleotides 3-180, 181-360, 361-539 and 540-722). Alternatively, it may be divided into regions that encode for conserved domains such as, for example, the PHD (see FIG. 12).

V. Cloning of the p28ING5 Genomic Sequence (or Gene)

The p28ING5 cDNA sequence and fragments described above does not contain introns, upstream transcriptional promoter or regulatory regions or downstream transcriptional regulatory regions of the p28ING5 gene. It is possible that some mutations in the p28ING5 gene that may lead to tumor formation or progression are not included in the cDNA but rather are located in other regions of the p28ING5 gene. Mutations located outside of the ORF that encodes the p28ING5 protein are not likely to affect the functional activity of the protein, but rather are likely to result in altered levels of the protein in the cell. For example, mutations in the promoter region of the p28ING5 gene may prevent transcription of the gene and therefore lead to the complete absence of the p28ING5 protein in the cell.

Additionally, mutations within introns in the genomic sequence may also prevent expression of the p28ING5 protein. Following transcription of a gene containing introns, the intron sequences are removed from the RNA molecule, in a process termed splicing, prior to translation of the RNA molecule which results in production of the encoded protein. When the RNA molecule is spliced to remove the introns, the cellular enzymes that perform the splicing function recognize sequences around the intron/exon border and in this manner recognize the appropriate splice sites. If there is a mutation within the sequence of the intron close to the junction of the intron with an exon, the enzymes may not recognize the junction and may fail to remove the intron. If this occurs, the encoded protein will likely be defective. Thus, mutations inside the intron sequences within the p28ING5 gene (termed "splice site mutations") may also lead to neoplasia. However, knowledge of the exon structure and intronic splice site sequences of the p28ING5 gene is required to define the molecular basis of these abnormalities. The provision herein of the p28ING5 cDNA sequence enables the cloning of the entire p28ING5 gene (including the promoter and other regulatory regions and the intron sequences) and the determination of its nucleotide sequence. With this information in hand, diagnosis of a genetic predisposition to tumor formation and progression based on DNA analysis will comprehend all possible mutagenic events at the p28ING5 locus.

The p28ING5 gene may be isolated by routine procedures. For instance, the p28ING5 gene may be isolated by homology screening using the cDNA sequence and the BLAST program. Direct sequencing, using the "long-distance sequence method," of one or more BAC or PAC clones that contain the p28ING5 sequence can be employed.

With the sequences of human p28ING5 cDNA and gene in hand, primers derived from these sequences may be used in diagnostic tests (described below) to determine the presence of mutations in any part of the genomic p28ING5 gene of a subject. In one embodiment, such primers will be oligonucleotides comprising a fragment of sequence from the p28ING5 gene (intron sequence, exon sequence or a sequence spanning an intron-exon boundary) and may include at least 6 consecutive nucleotides of a p28ING5 encoding sequence, such as the cDNA or gene. It will be appreciated that greater specificity may be achieved by using primers of greater lengths. Thus, in other embodiments, the primers used may comprise 15, 20, 23, 25, 30, 40, 50 or more consecutive nucleotides of the p28ING5 cDNA or gene. Furthermore, with the provision of the p28ING5 intron sequence information the analysis of a large and as yet untapped source of patient material for mutations will now be possible using methods such as chemical cleavage of mismatches (Cotton et al., *Proc. Natl. Acad. Sci. USA* 85:4397-4401, 1985; Montandon et al., *Nucleic Acids Res.* 9:3347-3358, 1989) and single-strand conform ational polymorphism analysis (SSCP) (Orita et al., *Genomics* 5:874-879, 1989).

Using the information disclosed herein, the regulatory elements flanking the p28ING5 gene can be identified and characterized. These regulatory elements may be characterized by standard techniques. In one embodiment deletion analysis is performed wherein successive nucleotides of a putative regulatory region are removed and the effect of the deletions is studied by transient expression analysis. In another embodiment, the effect of the deletions is studied by long-term expression analysis. The identification and characterization of regulatory elements flanking the genomic p28ING5 gene may be made by functional analysis (deletion analyses, etc.) in mammalian cells by either transient or long-term expression analyses.

It will be apparent to one skilled in the art that either the genomic clone or the cDNA or sequences derived from these clones may be utilized in applications, including but not limited to, studies of the expression of the p28ING5 gene, studies of the function of the p28ING5 protein, the generation of antibodies to the p28ING5 protein, diagnosis and therapy of p28ING5 deleted or mutated in subjects to prevent or treat the defects in cell and tissue development, such as neoplasia. Descriptions of applications describing the use of p28ING5 cDNA, or fragments thereof, are therefore intended to comprehend the use of the genomic p28ING5 gene.

In one embodiment, p28ING5 cDNA sequences are used in FISH (fluorescence in situ hybridization) analysis to assign the gene to a specific chromosomal location. In FISH analysis, the cDNA is labeled with a fluorescent probe. It is then added to a chromosomal preparation from the sample of interest. The probe will hybridize to the chromosome carrying the sequence complementary to the labeled cDNA and after allowing a sufficient time for annealing to occur, the labeled chromosomes can be viewed using a fluorescent microscope. In this way, the gene from which the cDNA is derived can be assigned to a specific chromosome. If FISH is coupled with chromosome banding, the probe can be localized to a specific band of the chromosome. FISH analysis has been useful for studying human diseases. For example, if FISH analysis determines that a cell from a subject suffering from a disease has a deletion at a specific chromosomal location, then the gene responsible for the disease is likely to reside on the missing segment. FISH analysis of tumor tissues has revealed that chromosomal deletions may be characteristic of cancers which are caused by the lack of a tumor suppressor gene.

It will also be apparent to one skilled in the art that homologs of the p28ING5 gene may now be cloned from other species, such as the rat or a monkey, by standard cloning methods. Such homologs will be useful in the production of animal models demonstrating the formation and progression of a variety of tumors. In one embodiment, such orthologous p28ING5 molecules will share at least 65% sequence identity with the human p28ING5 nucleic acid disclosed herein; and in other embodiments, more closely related orthologous sequences will share at least 70%, at least 75%, at least 80%, at least 90%, at least 95%, or at least 98% sequence identity with this sequence.

VI. p28ING5 Sequence Variants

With the provision of human p28ING5 protein and corresponding nucleic acid sequences herein, the creation of variants of these sequences is now enabled.

In one embodiment, variant p28ING5 proteins include proteins that differ in amino acid sequence from the human p28ING5 sequences disclosed but that share at least 72% amino acid sequence identity with the provided human p28ING5 protein. In other embodiments, other variants will share at least 75%, at least 80%, at least 85%, at least 90%, at least 95%, or at least 98% amino acid sequence identity. Manipulation of the nucleotide sequence of p28ING5 using standard procedures, including in one specific, non-limiting, embodiment, site-directed mutagenesis or in another specific, non-limiting, embodiment, PCR, can be used to produce such variants. The simplest modifications involve the substitution of one or more amino acids for amino acids having similar biochemical properties. These so-called conservative substitutions are likely to have minimal impact on the activity of the resultant protein.

In another embodiment, more substantial changes in tumor suppressor function or other protein features may be obtained by selecting amino acid substitutions that are less conservative than conservative substitutions. In one specific, non-limiting, embodiment, such changes include changing residues that differ more significantly in their effect on maintaining polypeptide backbone structure (e.g., sheet or helical conformation) near the substitution, charge or hydrophobicity of the molecule at the target site, or bulk of a specific side chain. The following specific, non-limiting, examples are generally expected to produce the greatest changes in protein properties: (a) a hydrophilic residue (e.g., seryl or threonyl) is substituted for (or by) a hydrophobic residue (e.g., leucyl, isoleucyl, phenylalanyl, valyl or alanyl); (b) a cysteine or proline is substituted for (or by) any other residue; (c) a residue having an electropositive side chain (e.g., lysyl, arginyl, or histadyl) is substituted for (or by) an electronegative residue (e.g., glutamyl or aspartyl); or (d) a residue having a bulky side chain (e.g., phenylalanine) is substituted for (or by) one lacking a side chain (e.g., glycine).

In other embodiments, changes in tumor suppressor activity or other protein features may be obtained by mutating, substituting or deleting regions of p28ING5 that have a known function, regions where the function is yet to be determined, or regions that are known to be highly conserved or not conserved. For instance, a PHD (plant homeo domain) motif at the C-terminal region of p28ING5 (corresponding to residues 186 through 235 of SEQ ID NO: 2; see also FIG. 12) can be deleted, substituted with the PHD of another protein or a synthetic PHD, or residues within the PHD motif mutated. In other embodiments, residues within at least one p28ING5 nuclear localization signal (NLS) (for example, corresponding to residues 129-146 or 222-240 of SEQ ID NO: 2) are mutated or deleted, or the NLS is substituted with a nuclear localization signal of another protein or a synthetic NLS.

Variant p28ING5 encoding sequences may be produced by standard DNA mutagenesis techniques. In one specific, non-limiting, embodiment, M13 primer mutagenesis is performed. Details of these techniques are provided in Sambrook et al. (In Molecular Cloning: A Laboratory Manual, CSHL, New York, 1989), Ch. 15. By the use of such techniques, variants may be created that differ in minor ways from the human p28ING5 sequences disclosed. In one embodiment, DNA molecules and nucleotide sequences that are derivatives of those specifically disclosed herein, and which differ from those disclosed by the deletion, addition, or substitution of nucleotides while still encoding a protein that has at least 65% sequence identity with the human p28ING5 encoding sequence disclosed (SEQ ID NO: 1), are comprehended by this disclosure. In other embodiments, more closely related nucleic acid molecules that share at least 70%, at least 75%, at least 80%, at least 85%, at least 90%, at least 95%, or at least 98% nucleotide sequence identity with the disclosed p28ING5 sequences are comprehended by this disclosure. Alternatively, related nucleic acid molecules can have no more than 3, 5, 10, 20, 50, 75, or 100 nucleic acid changes compared to SEQ ID NO: 1. In one embodiment, such variants may differ from the disclosed sequences by alteration of the coding region to fit the codon usage bias of the particular organism into which the molecule is to be introduced.

In other embodiments, the coding region may be altered by taking advantage of the degeneracy of the genetic code to alter the coding sequence such that, while the nucleotide sequence is substantially altered, it nevertheless encodes a protein having an amino acid sequence substantially similar to the disclosed human p28ING5 protein sequences. For example, because of the degeneracy of the genetic code, four nucleotide codon triplets—(GCT, GCG, GCC and GCA)—code for alanine. The coding sequence of any specific alanine residue within the human p28ING5 protein, therefore, could be changed to any of these alternative codons without affecting the amino acid composition or characteristics of the encoded protein. Based upon the degeneracy of the genetic code, variant DNA molecules may be derived from the cDNA and gene sequences disclosed herein using standard DNA mutagenesis techniques as described above, or by synthesis of DNA sequences. Thus, this disclosure also encompasses nucleic acid sequences that encode a p28ING5 protein, but which vary from the disclosed nucleic acid sequences by virtue of the degeneracy of the genetic code.

In one embodiment, variants of the p28ING5 protein may also be defined in terms of their sequence identity with the prototype human p28ING5 protein. As described above, human p28ING5 proteins share at least 72%, at least 75%, at least 80%, at least 85%, at least 90%, at least 95%, or at least 98% amino acid sequence identity with the human p28ING5 protein (SEQ ID NO: 2). Alternatively, variants of the p28ING5 protein can have no more than 3, 5, 10, 15, 20, 25, 30, 40, or 50 amino acid changes compared to SEQ ID NO: 2. Nucleic acid sequences that encode such proteins/fragments readily may be determined simply by applying the genetic code to the amino acid sequence of a p28ING5 protein or fragment, and such nucleic acid molecules may readily be produced by assembling oligonucleotides corresponding to portions of the sequence.

Nucleic acid molecules that are derived from the human p28ING5 cDNA nucleic acid sequences include molecules that hybridize under low stringency, high stringency, or very high stringency conditions to the disclosed prototypical p28ING5 nucleic acid molecules, and fragments thereof.

Human p28ING5 nucleic acid encoding molecules (including the cDNA shown in SEQ ID NO: 1, and nucleic acids comprising this sequence), and orthologs and homologs of these sequences, may be incorporated into transformation or expression vectors.

VII. Expression of p28ING5 Protein

With the provision of human p28ING5 encoding sequences (such as the cDNA shown in SEQ ID NO: 1), the expression and purification of the p28ING5 protein by standard laboratory techniques is now enabled. Purified human p28ING5 protein may be used for functional analyses, antibody production, diagnostics, and patient therapy.

For instance, the DNA sequence of the p28ING5 cDNA can be manipulated in studies to understand the expression of the gene and the function of its product. In other embodiments, mutant forms of the human p28ING5 may be isolated based upon information contained herein, and may be studied in order to detect alteration in expression patterns in terms of relative quantities, cellular localization, tissue specificity and functional properties of the encoded mutant p28ING5 protein. In yet other embodiments, partial or full-length cDNA sequences, which encode for the subject protein, may be ligated into bacterial expression vectors.

Methods for expressing large amounts of protein from a cloned gene introduced into *Escherichia coli* (*E. coli*) may be utilized for the purification, localization and functional analysis of proteins. By way of example, fusion proteins consisting of amino terminal peptides encoded by a portion of the *E. coli* lacZ or trpE gene linked to p28ING5 proteins may be used to prepare polyclonal and monoclonal antibodies against these proteins. Thereafter, these antibodies may be used in other embodiments to purify proteins by immunoaffinity chromatography, in diagnostic assays to quantitate the levels of protein and to localize proteins in tissues and individual cells by immunofluorescence. Such antibodies may be specific for epitope tags, which can be added to the expression construct for identification and/or purification purposes.

Intact native protein also may be produced in *E. coli* or other cell culture systems in large amounts for functional studies. Methods and plasmid vectors for producing fusion proteins and intact native proteins in bacteria are described in Sambrook et al. (Sambrook et al., *In Molecular Cloning: A Laboratory Manual*, Ch. 17, CSHL, New York, 1989). Such fusion proteins may be made in large amounts, are easy to purify, and can be used to elicit antibody response. In one embodiment, native proteins can be produced in bacteria by placing a strong, regulated promoter and an efficient ribosome binding site upstream of the cloned gene. If low levels of protein are produced, additional steps may be taken to increase protein production; if high levels of protein are produced, purification is relatively easy. Suitable methods are presented in Sambrook et al (In *Molecular Cloning: A Laboratory Manual*, CSHL, New York, 1989) and are well known in the art. In one embodiment, proteins expressed at high levels are found in insoluble inclusion bodies. Methods for extracting proteins from these aggregates are described by Sambrook et al. (In *Molecular Cloning: A Laboratory Manual*, Ch. 17, CSHL, New York, 1989).

Vector systems suitable for the expression of lacZ fusion genes include the pUR series of vectors (Ruther and Muller-Hill, *EMBO J*. 2:1791, 1983), pEX 1-3 (Stanley and Luzio, *EMBO J*. 3:1429, 1984) and pMR100 (Gray et al., *Proc. Natl. Acad. Sci. USA* 79:6598, 1982). Vectors suitable for the production of intact native proteins include pKC30 (Shimatake and Rosenberg, *Nature* 292:128, 1981), pKK177-3 (Amann and Brosius, *Gene* 40:183, 1985) and pET-3 (Studiar and Moffatt, *J. Mol. Biol*. 189:113, 1986). In one embodiment, p28ING5 fusion proteins may be isolated from protein gels, lyophilized, ground into a powder and used as an antigen. In other embodiments, the DNA sequence can also be transferred from its existing context to other cloning vehicles, such as other plasmids, bacteriophages, cosmids, animal viruses and yeast artificial chromosomes (YACs) (Burke et al., *Science* 236:806-812, 1987). These vectors may then be introduced into a variety of hosts including, but not limited to, somatic cells, and simple or complex organisms, such as, but not limited to, bacteria, fungi (Timberlake and Marshall, *Science* 244:1313-1317, 1989), invertebrates, plants, and animals (Pursel et al., *Science* 244:1281-1288, 1989), which cells or organisms are rendered transgenic by the introduction of the heterologous p28ING5 cDNA.

For expression in mammalian cells, the cDNA sequence may be ligated to heterologous promoters. In one specific, non-limiting embodiment it may be ligated to the simian virus (SV) 40 promoter in the pSV2 vector (Mulligan and Berg *Proc. Natl. Acad Sci. USA* 78:2072-2076, 1981), and introduced into cells, such as monkey COS-1 cells (Gluzman, *Cell* 23:175-182, 1981), to achieve transient or long-term expression. In one embodiment, the stable integration of the chimeric gene construct may be maintained in mammalian cells by biochemical selection, such as neomycin (Southern and Berg, *J. Mol. Appl. Genet*. 1:327-341, 1982) and mycophenolic acid (Mulligan and Berg, *Proc. Natl. Acad. Sci. USA* 78:2072-2076, 1981). In another embodiment, cell lines expressing native p28ING5 are created. In yet another embodiment, cell lines expressing a mutant p28ING5 are created.

DNA sequences can be manipulated with standard procedures such as restriction enzyme digestion, fill-in with DNA polymerase, deletion by exonuclease, extension by terminal deoxynucleotide transferase, ligation of synthetic or cloned DNA sequences, site-directed sequence-alteration via single-stranded bacteriophage intermediate or with the use of specific oligonucleotides in combination with nucleic acid amplification. These techniques are known to those of ordinary skill.

The p28ING5 cDNA sequence (or portions derived from it) or a mini gene (a cDNA with an intron and its own promoter) may be introduced into eukaryotic expression vectors by conventional techniques. These vectors are designed to permit the transcription of the cDNA in eukaryotic cells by providing regulatory sequences that initiate and enhance the transcription of the cDNA and ensure its proper splicing and polyadenylation. Vectors containing the promoter and enhancer regions of the SV40 or long terminal repeat (LTR) of the Rous Sarcoma virus and polyadenylation and splicing signal from SV40 are readily available (Mulligan et al, *Proc. Natl. Acad. Sci. USA* 78:1078-2076, 1981; Gorman et at, *Proc. Natl. Acad. Sci. USA* 78:6777-6781, 1982). The level of expression of the cDNA can be manipulated with this type of vector by using promoters that have different activities (for example, the baculovirus pAC373 can express cDNAs at high levels in *S. frugiperda* cells (Summers and Smith, In *Genetically Altered Viruses and the Environment*, Fields el at (Eds.) 22:319-328, CSHL Press, Cold Spring Harbor, N.Y., 1985) or by using vectors that contain promoters amenable to modulation, for example, the glucocorticoid-responsive promoter from the mouse mammary tumor virus (Lee et al, *Nature* 294:228, 1982). The expression of the cDNA can be monitored in the recipient cells 24 to 72 hours after introduction (transient expression).

Some vectors contain selectable markers such as the gpt (Mulligan and Berg *Proc. Natl. Acad. Sci. USA* 78:2072-2076, 1981) or neomycin (Southern and Berg *J. Mol. Appl Genet*. 1:327-341, 1982) bacterial genes. These selectable markers permit selection of transfected cells that exhibit stable, long-term expression of the vectors (and therefore the cDNA). By way of example, the vectors can be maintained in the cells as episomal, freely replicating entities by using regulatory elements of viruses, such as papilloma (Sarver et al., *Mol. Cell Biol*. 1:486496, 1981) or Epstein-Barr (Sugden et al., *Mol. Cell Biol*. 5:410-413, 1985). In another embodiment, one can produce cell lines that have integrated the vector into genomic DNA. Both of these types of cell lines produce the gene product on a continuous basis. Alternatively, one can produce cell lines that have amplified the number of copies of the vector (and therefore of the cDNA as well) to create cell lines that can produce high levels of the gene product (Alt et al, *J. Biol. Chem*. 253:1357-1370, 1978).

The vectors may contain an internal ribosomal entry site (IRES) between the cDNA and a marker gene, such as neomycin or enhanced green fluorescent protein (EGFP). The IRES allows for the simultaneous expression of the two elements from a single transcript. Ribosomes bind the transcript at both the 5' end to translate the cDNA and at the IRES to translate, in one specific, non-limiting embodiment, the antibiotic resistance marker, or in another specific, non-limiting embodiment, the fluorescent marker. The bicistronic expression via the IRES sequence provides a high degree of correlation between the antibiotic resistance and stable expression of the cDNA. Alternatively, only cells expressing the cDNA will show green fluorescence. Thus, the use of expression vectors containing an IRES is an efficient way to select for cells expressing the cDNA of interest.

The transfer of DNA into eukaryotic, in particular human or other mammalian cells, is now a conventional technique. Recombinant expression vectors can be introduced into the recipient cells as pure DNA (transfection) by, for example, precipitation with calcium phosphate (Graham and vander Eb, *Virology* 52:466, 1973) or strontium phosphate (Brash et al., *Mol. Cell Biol*. 7:2013, 1987), electroporation (Neumann et al, *EMBO J*. 1:841, 1982), lipofection (Felgner et al., *Proc. Natl. Acad. Sci USA* 84:7413, 1987), DEAE dextran (Mc-Cuthan et al., *J Natl. Cancer Inst*. 41:351, 1968), microinjection (Mueller et al., *Cell* 15:579, 1978), protoplast fusion (Schafner, *Proc. Natl. Acad. Sci. USA* 77:2163-2167, 1980), or pellet guns (Klein et al., *Nature* 327:70, 1987). In another embodiment, the cDNA, or fragments thereof, can be introduced by infection with virus vectors. Systems are developed that use, for example, retroviruses (Bernstein et al., *Gen Engr'g* 7:235, 1985), adenoviruses (Ahmad et al., *J. Virol*. 57:267, 1986), or Herpes virus (Spaete et al., *Cell* 30:295, 1982). Techniques of use in packaging long transcripts can be found in Kochanek et al. (*Proc. Natl. Acad. Sci. USA* 93:5731-5739, 1996), Parks et al. (*Proc. Natl. Acad. Sci. USA* 93:13565-13570, 1996) and Parks and Graham (*J. Virol*. 71:3293-3298, 1997). In yet another embodiment, p28ING5 encoding sequences can be delivered to target cells in vitro via non-infectious systems, for instance liposomes.

These eukaryotic expression systems can be used for studies of p28ING5 encoding nucleic acids and mutant forms of these molecules, the p28ING5 protein and mutant forms of this protein. Regulatory elements located in the 5' region of the p28ING5 gene on genomic clones can be isolated from human genomic DNA libraries using the information contained herein. In other embodiments, the eukaryotic expression systems also may be used to study the function of the normal complete protein, specific portions of the protein, or of naturally occurring or artificially produced mutant proteins.

In several embodiments, using the above techniques, expression vectors containing the p28ING5 gene sequence or cDNA, or fragments or variants or mutants thereof, can be introduced into human cells, mammalian cells from other species or non-mammalian cells, as desired. The choice of cell is determined by the purpose of the treatment. For example, in one specific, non-limiting embodiment monkey COS cells (Gluzman, *Cell* 23:175-82, 1981) that produce high levels of the SV40 T antigen and permit the replication of vectors containing the SV40 origin of replication are used. In other embodiments, Chinese hamster ovary (CHO), mouse NIH 3T3 fibroblasts, or human fibroblasts or lymphoblasts are used.

Embodiments described herein thus encompass recombinant vectors that comprise all or part of a p28ING5 encoding sequence, such as the p28ING5 gene or cDNA or variants thereof, for expression in a suitable host. In one embodiment, the p28ING5 DNA is operatively linked in the vector to an expression control sequence in the recombinant DNA molecule so that the p28ING5 polypeptide can be expressed. In another embodiment, the expression control sequence may be selected from the group consisting of sequences that control the expression of genes of prokaryotic or eukaryotic cells and their viruses and combinations thereof. The expression control sequence may be specifically selected from the group consisting of the lac system, the trp system, the tac system, the trc system, major operator and promoter regions of phage lambda, the control region of coat protein, the early and late promoters of SV40, promoters derived from polyoma, adenovirus, retrovirus, baculovirus and simian virus, the promoter for 3-phosphoglycerate kinase, the promoters of yeast acid phosphatase, the promoter of the yeast alpha-mating factors and combinations thereof.

In another embodiment, the host cell, which may be transfected with a vector, may be selected from the group consisting of *E. coli, Pseudomonas, Bacillus subtilis, Bacillus stearothermophilus* or other bacilli; other bacteria; yeast; fungi; insect; mouse or other animal; or plant hosts; or human tissue cells.

It is appreciated that for mutant or variant p28ING5 DNA sequences, similar systems are employed to express and produce the mutant product.

VII. Suppression of p28ING5 Protein

In one embodiment, a reduction of p28ING5 protein expression in a transgenic cell may be obtained by introducing into cells an antisense construct based on the p28ING5 encoding sequence, including the human p28ING5 cDNA (SEQ ID NO: 1) or gene sequence or flanking regions thereof. In one specific, non-limiting embodiment, a nucleotide sequence from a p28ING5 encoding sequence, e.g. all or a portion of the p28ING5 cDNA or gene, is arranged in reverse orientation relative to the promoter sequence in the transformation vector. Other aspects of the vector may be chosen as discussed above (Section VII, for instance).

The introduced sequence need not be the full length human p28ING5 cDNA (SEQ ID NO: 1) or gene, and need not be exactly homologous to the equivalent sequence found in the cell type to be transfected. In one embodiment, portions or fragments of the human cDNA (SEQ ID NO: 1) could be used to knock out expression of the human p28ING5 gene. Generally, however, where the introduced sequence is of shorter length, a higher degree of identity to the native p28ING5 sequence will be needed for effective antisense suppression. In other embodiments, the introduced antisense sequence in the vector may be at least 15 nucleotides in length, and improved antisense suppression typically will be observed as the length of the antisense sequence increases. In yet other embodiments, the length of the antisense sequence in the vector advantageously may be greater than 100 nucleotides, and can be up to about the full length of the human p28ING5 cDNA or gene. In another embodiment, for suppression of the p28ING5 gene itself, transcription of an antisense construct results in the production of RNA molecules that are the reverse complement of mRNA molecules transcribed from the endogenous p28ING5 gene in the cell.

Although the exact mechanism by which antisense RNA molecules interfere with gene expression has not been elucidated, it is believed that antisense RNA molecules bind to the endogenous mRNA molecules and thereby inhibit translation of the endogenous mRNA. Expression of p28ING5 can also be reduced using small inhibitory RNAs (siRNAs), for instance using techniques similar to those described previously (see, e.g., Tuschl et al., *Genes Dev* 13, 3191-3197, 1999; Caplen et al., *Proc. Nat.l Acad. Sci. U.S.A*. 98, 9742-9747, 2001; Elbashir et al., *Nature* 411, 494-498, 2001; and U.S. Pat. No. 6,506,559 BI).

In another embodiment, suppression of endogenous p28ING5 expression can be achieved using ribozymes. Ribozymes are synthetic RNA molecules that possess highly specific endoribonuclease activity. The production and use of ribozymes are disclosed in U.S. Pat. No. 4,987,071 to Cech and U.S. Pat. No. 5,543,508 to Haselhoff. In one embodiment, the inclusion of ribozyme sequences within antisense RNAs may be used to confer RNA cleaving activity on the antisense RNA, such that endogenous mRNA molecules that bind to the antisense RNA are cleaved, which in turn leads to an enhanced antisense inhibition of endogenous gene expression.

In yet another embodiment, dominant negative mutant forms of p28ING5 may be used to block endogenous p28ING5 activity.

IX. Production of an Antibody to p28ING5 Protein

Monoclonal or polyclonal antibodies may be produced to either the normal p28ING5 protein or mutant forms of this protein. In one embodiment, antibodies raised against the p28ING5 protein would specifically detect the p28ING5 protein. That is, such antibodies would recognize and bind the p28ING5 protein, or fragments thereof, and would not substantially recognize or bind to other proteins found in human cells. In some embodiments, antibodies against the human p28ING5 protein may recognize p28ING5 from other species (e.g., murine p28ING5), and vice versa.

Monoclonal or polyclonal antibodies to the protein can be prepared as follows:

A. Monoclonal Antibody Production by Hybridoma Fusion

Monoclonal antibody to epitopes of the p28ING5 protein identified and isolated as described can be prepared from murine hybridomas according to the classical method of Kohler and Milstein (*Nature* 256:495497, 1975) or derivative methods thereof. In one specific, non-limiting embodiment, a mouse is repetitively inoculated with a few micrograms of the selected protein over a period of a few weeks. The mouse is then sacrificed, and the antibody-producing cells of the spleen isolated. The spleen cells are fused with mouse myeloma cells using polyethylene glycol, and the excess, non-fused, cells destroyed by growth of the system on selective media comprising aminopterin (HAT media). Successfully fused cells are diluted and aliquots of the dilution placed in wells of a microtiter plate, where growth of the culture is continued. Antibody-producing clones are identified by detection of antibody in the supernatant fluid of the wells by immunoassay procedures, such as ELISA, as originally described by Engvall (*Enzymol*. 70(A):419-439, 1980), and derivative methods thereof. Selected positive clones can be expanded and their monoclonal antibody product harvested for use. Detailed procedures for monoclonal antibody production are described in Harlow and Lane (Antibodies, A Laboratory Manual, CSHL, New York, 1988).

B. Polyclonal Antibody Production by Immunization

Polyclonal antiserum containing antibodies to heterogeneous epitopes of a single protein can be prepared by immunizing suitable animals with the expressed protein (for instance, expressed using a method described herein), which, in one specific, non-limiting embodiment, can be modified to enhance immunogenicity. Effective polyclonal antibody production is affected by many factors related both to the antigen and the host species. In one embodiment, small molecules may tend to be less immunogenic than others and may require the use of carriers and adjuvant, examples of which are known. In another embodiment, host animals may vary in response to site of inoculations and dose, with either inadequate or excessive doses of antigen resulting in low titer antisera. In one specific, non-limiting embodiment, a series of small doses (ng level) of antigen administered at multiple intradermal sites may be most reliable. An effective immunization protocol for rabbits can be found in Vaitukaitis et al. (*J. Clin. Endocrinol. Metab*. 33:988-991, 1971).

In one embodiment, booster injections will be given at regular intervals, and antiserum harvested when antibody titer thereof begins to fall, as determined semi-quantitatively (for example, by double immunodiffusion in agar against known concentrations of the antigen). See, for example, Ouchterlony et al. (In *Handbook of Experimental Immunology*, Wier, D. (ed.) chapter 19. Blackwell, 1973). In one specific, non-limiting embodiment the plateau concentration of antibody is usually in the range of about 0.1 to 0.2 mg/ml of serum (about 12 µM). Affinity of the antisera for the antigen is determined by preparing competitive binding curves, as described, for example, by Fisher (*Manual of Clinical Immunology*, Ch. 42, 1980).

C. Antibodies Raised against Synthetic Peptides

A third approach to raising antibodies against the p28ING5 protein is to use synthetic peptides synthesized on a commercially available peptide synthesizer based upon the predicted amino acid sequence of the p28ING5 protein. Polyclonal antibodies can be generated by injecting such peptides into, for instance, rabbits (Example 3, for instance).

D. Antibodies Raised by Injection of p28ING5 Encoding Sequence

In one embodiment, antibodies may be raised against the p28ING5 protein by subcutaneous injection of a recombinant DNA vector that expresses the p28ING5 protein into laboratory animals, such as mice. In one specific, non-limiting embodiment, delivery of the recombinant vector into the animals may be achieved using a hand-held form of the Biolistic system (Sanford et al., *Particulate Sci. Technol*. 5:27-37, 1987), as described by Tang et al. (*Nature* 356:152-154, 1992). In other embodiments, expression vectors suitable for this purpose may include those that express the p28ING5 encoding sequence under the transcriptional control of either the human β-actin promoter or the cytomegalovirus (CMV) promoter.

Antibody preparations prepared according to these protocols are useful in quantitative immunoassays which determine concentrations of antigen-bearing substances in biological samples; they are also used semi-quantitatively or qualitatively to identify the presence of antigen in a biological sample.

X. p28ING5 as an Active Tumor Suppressor p28ING5 and its functional variants participate in the regulation of cell proliferation and tumor suppression. In one embodiment, the expression of p28ING5 in a cell inhibits its proliferation. In another embodiment, the expression of p28ING5 in a tumor suppresses the growth of the tumor. In one specific, non-limiting embodiment, the administration of a p28ING5 recombinant nucleotide to a subject suffering from a tumor inhibits the proliferation of the tumor and in another specific, non-limiting embodiment, the administration of the p28ING5 recombinant nucleotide reduces the size of the tumor. In yet another embodiment, the administration of the p28ING5 protein to a subject suffering from a tumor reduces the size of the tumor.

The expression of mutant tumor suppressors can yield important information about the importance of each amino acid in the protein as well as the details of the mechanism of action of these proteins. Cells may have p28ING5 null mutations, p28ING5 missense mutations, or inactivation of p28ING5. In one embodiment, a mutant p28ING5 is expressed in a cell but is incapable of localizing to the correct subcellular location. In another embodiment, a mutant p28ING5 is incapable of binding to its intracellular binding partners. In yet another embodiment, a mutation in the upstream regulatory region of the p28ING5 gene abrogates the expression of the protein.

Compounds that modulate the expression or activity p28ING5 can be used to regulate cellular proliferation and inhibit the progression of tumors. In one embodiment, it may be determined that p28ING5 is expressed at low levels in a subject suffering from a tumor which arose as the result of the inefficient expression of p28ING5. Administration, to the subject, of an agent that up-regulates p28ING5 expression can reduce the size of the tumor or completely eliminate the tumor.

Changes in cell growth can be assessed by using a variety of in vitro and in vivo assays. These assays can be used to study the effect of p28ING5 on specific cell types or the effect of particular mutations on p28ING5 tumor suppressor activity. By systematically introducing mutant p28ING5 constructs into cells and assessing their ability to grow, the importance of each amino acid for the protein's tumor suppressor activity can be determined. In addition, these assays can be used to screen for modulators of p28ING5 activity. The modulators identified in this way can then be used to alter p28ING5 expression in tumor cells in vitro or in vivo.

In one embodiment, tumor cells expressing wildtype p28ING5 are assessed for their ability to grow in soft agar, as compared to tumor cells that do not express p28ING5 or tumor cells that express a mutant p28ING5. Only transformed cells will grow colonies in soft agar, as they have lost the requirement to grow on a solid substrate. Therefore, cells expressing a wildtype p28ING5 protein, or cells expressing variants with a wildtype activity, will be unable to generate colonies in this assay. In another embodiment, cells transfected with wildtype p28ING5 or a mutant variant of p28ING5 will be compared to cells transfected with a control expression vector for their ability to grow in soft agar. Techniques for soft agar growth or colony formation are described in Freshney, *Culture of Animal Cells a Manual of Basic Technique*, 3$^{rd}$ ed., Wiley-Liss, New York (1994).

In one embodiment, cells expressing an inactive p28ING5 or cells lacking p28ING5 are compared with cells expressing wildtype p28ING5 or a functional variant of p28ING5 for their ability to grow to high densities in disorganized foci. Cells expressing wildtype p28ING5, or cells expressing variants with a wildtype activity, are contact inhibited and are unable to form foci in plastic tissue culture dishes. In another embodiment, cells are transfected with various p28ING5 mutant constructs. The cells are then assessed for their ability to form foci in order to identify functional variants of p28ING5.

In another embodiment, growth factor or serum dependence is used as an assay to identify functional p28ING5 variants as transformed cells have lower serum dependence and growth factor dependence than their normal counterparts. In yet another embodiment, the release of tumor specific markers from transformed cells is used as an assay to identify mutant p28ING5 constructs and functional variants. In another embodiment, the degree of invasiveness into Matrigel or some other extracellular matrix constituent can be used as an assay to identify p28ING5 variants that are capable of inhibiting abnormal cell proliferation and tumor growth.

In yet another embodiment, samples or assays that are treated with a test compound which potentially modulates p28ING5 are compared to control samples that are not treated with the test compound, to examine the extent of modulation. In one embodiment, the compounds to be tested are present in the range from 0.1 nM to 10 mM. Control samples, (untreated with modulators) are assigned a relative p28ING5 activity value of 100%. In one embodiment, inhibition of p28ING5 is achieved when the p28ING5 activity value relative to the control is about 90%. In other embodiments, inhibition of p28ING5 is achieved when the p28ING5 activity value relative to the control is about 75%, about 50%, about 25%, or about 5%. In another embodiment, activation of p28ING5 is achieved when the p28ING5 activity value relative to the control is about 110% (e.g. 10% more than the control). In other embodiments, activation of p28ING5 is achieved when the p28ING5 activity value relative to the control is about 150%, about 175% or about 200%.

The effect of test compounds upon p28ING5 activity can be assessed using the assays described above. Such assays include, but are not limited to, the ability to grow on soft agar, contact inhibition, growth factor and serum dependence, tumor specific marker levels, invasiveness into Matrigel. In other embodiments, the effect of potential modulators on p28ING5 protein or mRNA levels, transcriptional activation or repression of a reporter gene is measured. In yet another embodiment, the effects of the potential modulator are performed in vivo by injecting cultured cells expressing wildtype or mutant p28ING5 into an immune compromised mouse, such as an athymic mouse, an irradiated mouse, or a SCID mouse. p28ING5 modulators are administered to the mouse and after a suitable length of time, preferably 4-8 weeks, tumor growth is measured, e.g. by volume or by dimension, and compared to a control. Tumors that have statistically significant reduction are said to have inhibited growth.

In one embodiment, the compounds tested as modulators of p28ING5 are any small chemical compound, or biological entity, such as a polypeptide, sugar, nucleic acid or lipid. In another embodiment, the modulator is a genetically altered version of p28ING5.

XI. DNA-Based Diagnosis

The p28ING5 sequence information presented herein can be used in the area of genetic testing for predisposition to tumor formation and progression, owing to defects in p28ING5, such as deletion, duplication or mutation. The gene sequence of the p28ING5 gene, including intron-exon boundaries is also useful in such diagnostic methods. Individuals carrying mutations in the p28ING5 gene (or a portion thereof), or having duplications or heterozygous or homozygous deletions of the p28ING5 gene, may be detected at the DNA level with the use of a variety of techniques. For such a diagnostic procedure, a biological sample of the subject, which biological sample contains either DNA or RNA derived from the subject, is assayed for a mutated, duplicated or deleted p28ING5 gene. Suitable biological samples include samples containing genomic DNA or RNA obtained from body cells, such as those present in peripheral blood, urine, saliva, tissue biopsy, surgical specimen, amniocentesis samples and autopsy material. Biological samples can be obtained from normal, healthy subjects or from subjects who are predisposed to or who are suffering from any one of a variety of tumors such as, but not limited to, tumors of the breast, lung, colon, pancreas, liver, brain, blood, skin, prostate, testis, ovary, and stomach. The detection in the biological sample of either a mutant p28ING5 gene, a mutant p28ING5 RNA, or a duplicated or homozygously or heterozygously deleted p28ING5gene, may be performed by a number of methodologies, examples of which are discussed below.

One embodiment of such detection techniques for the identification of unknown mutations is the amplification (e.g., polymerase chain reaction amplification) of reverse transcribed RNA (RT-PCR) isolated from a subject, followed by direct DNA sequence determination of the products. The presence of one or more nucleotide differences between the obtained sequence and the prototypical p28ING5 cDNA sequence, and especially, differences in the ORF portion of the nucleotide sequence, are taken as indicative of a potential p28ING5 gene mutation.

Alternatively, DNA extracted from a biological sample may be used directly for amplification. Direct amplification from genomic DNA would be appropriate for analysis of the entire p28ING5 gene including regulatory sequences located upstream and downstream from the open reading frame, or intron/exon borders. Reviews of direct DNA diagnosis have been presented by Caskey (*Science* 236:1223-1228, 1989) and by Landegren et al. (*Science* 242:229-237, 1989).

Other mutation scanning techniques appropriate for detecting unknown mutations within amplicons derived from DNA or cDNA could also be performed. These techniques include direct sequencing (without sequencing), single-strand conformational polymorphism analysis (SSCP) (for instance, see Hongyo et al., *Nucleic Acids Res.* 21:3637-3642, 1993), chemical cleavage (including HOT cleavage) (Bateman et al., *Am. J. Med. Genet.* 45:233-240, 1993; reviewed in Ellis et al., *Hum. Mutat.* 11:345-353, 1998), denaturing gradient gel electrophoresis (DGGE), ligation amplification mismatch protection (LAMP), and enzymatic mutation scanning (Taylor and Deeble, *Genet. Anal.* 14:181-186, 1999), followed by direct sequencing of amplicons with putative sequence variations.

If studies of p28ING5 genes/coding sequences isolated from tumor samples reveal particular mutations, genomic amplifications, or deletions, which occur at a high frequency within a population of individuals, DNA diagnostic methods can be designed to specifically detect the most common, or most closely disease-linked, p28ING5 defects.

The detection of specific DNA mutations may be achieved by methods such as hybridization using allele specific oligonucleotides (ASOs) (Wallace et al, *CSHL Symp. Quant. Biol.* 51:257-261, 1986), direct DNA sequencing (Church and Gilbert Proc. Natl. Acad. Sci. USA 81:1991-1995, 1988), the use of restriction enzymes (Flavell et al., *Cell* 15:25-41, 1978; Geever et al., 1981), discrimination on the basis of electrophoretic mobility in gels with denaturing reagent (Myers and Maniatis, Cold Spring Harbor Symp. Quant. Biol. 51:275-284, 1986), RNase protection (Myers et al, *Science* 230:1242-1246, 1985), chemical cleavage (Cotton et al., *Proc. Natl. Acad. Sci. USA* 85:4397-4401, 1985), and the ligase-mediated detection procedure (Landegren et al., *Science* 241: 1077-1080, 1988).

Oligonucleotides specific to normal or mutant sequences are chemically synthesized using commercially available machines. These oligonucleotides are then labeled radioactively with isotopes (such as $^{32}P$) or non-radioactively, with tags such as biotin (Ward and Langer, Proc. Natl. Acad. Sci. USA 78:6633-6657, 1981), and hybridized to individual DNA samples immobilized on membranes or other solid supports by dot-blot or transfer from gels after electrophoresis. These specific sequences are visualized by methods such as autoradiography or fluorometric (Landegren et al, *Science* 242:229-237, 1989) or colorimetric reactions (Gebeyehu et al., *Nucleic Acids Res.* 15:4513-4534, 1987). Using an ASO specific for a normal allele, the absence of hybridization would indicate a mutation in the particular region of the gene, or deleted p28ING5 gene. In contrast, if an ASO specific for a mutant allele hybridizes to a clinical sample, this would indicate the presence of a mutation in the region defined by the ASO.

Sequence differences between normal and mutant forms of the p28ING5 gene may also be revealed by the direct DNA sequencing method of Church and Gilbert (*Proc. Natl. Acad. Sci. USA* 81:1991-1995, 1988). Cloned DNA segments may be used as probes to detect specific DNA segments. The sensitivity of this method is greatly enhanced when combined with nucleic acid amplification, e.g., PCR (Wrichnik et al., *Nucleic Acids Res.* 15:529-542, 1987; Wong et al., *Nature* 330:384-386, 1987; Stoflet et al., *Science* 239:491-494, 1988). In this approach, a sequencing primer that lies within the amplified sequence is used with double-stranded PCR product or single-stranded template generated by a modified PCR. The sequence determination is performed by conventional procedures with radiolabeled nucleotides or by automatic sequencing procedures with fluorescent tags.

Sequence alterations may occasionally generate fortuitous restriction enzyme recognition sites or may eliminate existing restriction sites. Changes in restriction sites are revealed by the use of appropriate enzyme digestion followed by conventional gel-blot hybridization (Southern, *J. Mol. Biol.* 98:503-517, 1975). DNA fragments carrying the restriction site (either normal or mutant) are detected by their reduction in size or increase in corresponding restriction fragment numbers. Genomic DNA samples may also be amplified by PCR prior to treatment with the appropriate restriction enzyme; fragments of different sizes are then visualized under UV light in the presence of ethidium bromide after gel electrophoresis.

Genetic testing based on DNA sequence differences may be achieved by detection of alteration in electrophoretic mobility of DNA fragments in gels, with or without denaturing reagent. Small sequence deletions and insertions can be visualized by high-resolution gel electrophoresis. For example, a PCR product with small deletions is clearly distinguishable from a normal sequence on an 8% non-denaturing polyacrylamide gel (WO 91/10734; Nagamine et al, *Am. J. Hum. Genet.* 45:337-339, 1989). DNA fragments of different sequence compositions may be distinguished on denaturing formamide gradient gels in which the mobilities of different DNA fragments are retarded in the gel at different positions according to their specific "partial-melting" temperatures (Myers et al., *Science* 230:1242-1246, 1985). Alternatively, a method of detecting a mutation comprising a single base substitution or other small change could be based on differential primer length in a PCR. For example, an invariant primer could be used in addition to a primer specific for a mutation. The PCR products of the normal and mutant genes can then be differentially detected in acrylamide gels. Another method, single-strand conformation polymorphism (SSCP), is based on the fact that a single-base substitution alters the conformation of single-stranded DNA under nondenaturing conditions. Altered conformation affects the migration velocity of single-stranded DNA, which is detected as shifted or new bands on a non-denaturing gel. The mutations underlying the shifted or new bands are then characterized by sequencing.

In addition to conventional gel-electrophoresis and blot-hybridization methods, DNA fragments may also be visualized by methods where the individual DNA samples are not immobilized on membranes. The probe and target sequences may be both in solution, or the probe sequence may be immobilized (Saiki et al., *Proc. Nat. Acad. Sci. USA* 86:6230-6234, 1989). A variety of detection methods, such as autoradiography involving radioisotopes, direct detection of radioactive decay (in the presence or absence of scintillant), spectrophotometry involving calorigenic reactions and fluorometry involved fluorogenic reactions, may be used to identify specific individual genotypes.

If multiple mutations are encountered frequently in the p28ING5 gene, a system capable of detecting such multiple mutations likely will be desirable. For example, a nucleic acid amplification reaction with multiple, specific oligonucleotide primers and hybridization probes may be used to identify all possible mutations at the same time (Chamberlain et al., *Nucl. Acids Res.* 16:1141-1155, 1988). The procedure may involve immobilized sequence-specific oligonucleotide probes (Saiki et at, *Proc. Nat. Acad. Sci. USA* 86:6230-6234, 1989).

Expression levels of the p28ING5 gene can also be determined by methods such as Northern or Southern blot analysis using labeled oligonucleotides specific to normal or mutant sequences. These oligonucleotides are labeled radioactively with isotopes (such as $^{32}P$) or non-radioactively, with tags such as biotin (Ward and Langer, *Proc. Natl. Acad. Sci. USA* 78:6633-6657, 1981), and hybridized to individual DNA samples immobilized on membranes or other solid supports by dot-blot or transfer from gels after electrophoresis. Quantitative or semi-quantitative PCR can also be used to measure the amount of p28ING5 cDNA in a sample using p28ING5 oligonucleotide primers. Visualization methods such as autoradiography or fluorometric (Landegren et al., *Science* 242: 229-237, 1989) orcolorimetric reactions (Gebeyehu et al, *Nucleic Acids Res*. 15:4513-4534, 1987) can be used to detect a signal and the signals quantitated using, for instance, a spectrophotometer, a scintillation counter, a densitometer or a Phosphorimager (Amersham Biosciences). The Phosphorimager is able to analyze both DNA and protein samples from blots and gels using autoradiographic, direct fluorescence or chemifluorescence detection. Since the Phosphorimager is more sensitive than ordinary x-ray film, exposure times can be reduced up to ten-fold and signal quantitation of both weak and strong signals on the same blot is possible. Images can be visualized and evaluated with the aid of computer programs such as ImageQuant™.

XII. Qualitative and Quantitative Detection of p28ING5 Protein

Antibodies can be used to assess the presence or absence of p28ING5 in cultured cells or primary cells. The determination that an antibody specifically detects the p28ING5 protein is made by any one of a number of standard immunoassay methods; for instance, the Western blotting technique (Sambrook et al., In *Molecular Cloning: A Laboratory Manual*, CSHL, New York, 1989). In one embodiment, it is determined whether a given antibody preparation (such as one produced in a mouse) specifically detects the p28ING5 protein by Western blotting. In one specific, non-limiting embodiment total cellular protein is extracted from human cells (for example, lymphocytes) and electrophoresed on a sodium dodecyl sulfate-polyacrylamide gel. In another embodiment, the cellular protein is extracted from a tumor. The proteins are then transferred to a membrane (for example, nitrocellulose or PVDF) by Western blotting, and the antibody preparation is incubated with the membrane. After washing the membrane to remove non-specifically bound antibodies, the presence of specifically bound antibodies is detected by the use of (by way of example) an anti-mouse antibody conjugated to an enzyme such as alkaline phosphatase. Application of an alkaline phosphatase substrate 5-bromo-chloro-3-indolyl phosphate/nitro blue tetrazolium results in the production of a dense blue compound by immunolocalized alkaline phosphatase. Antibodies that specifically detect the p28ING5 protein will, by this technique, be shown to bind to the p28ING5 protein band (which will be localized at a given position on the gel determined by its molecular weight, which is approximately 28 kDa based on its deduced amino acid sequence). Non-specific binding of the antibody to other proteins may occur and may be detectable as a weak signal on the Western blot. The non-specific nature of this binding will be recognized by one skilled in the art by the weak signal obtained on the Western blot relative to the strong primary signal arising from the specific antibody:p28ING5 protein binding.

In one embodiment, substantially pure p28ING5 protein suitable for use as an immunogen is isolated from the transfected cells as described above. In one specific, non-limiting embodiment the concentration of protein in the final preparation is adjusted, for example, by concentration on an Amicon (Millipore, Bedford, Mass.) or similar filter device, to the level of a few micrograms per milliliter.

In other embodiments, antibodies against p28ING5 are used to localize p28ING5 to specific cell types or to specific subcellular locations in immunohistochemical or immunofluorescence assays. In one embodiment, the cells are selected from a variety of cell lines. In other embodiments, primary cells are isolated from a tumor in a subject and are maintained in culture or the tumor is sectioned and the sections are prepared directly for immunohistochemistry or immunofluorescence. In one specific, non-limiting embodiment, the cells are fixed, incubated in a blocking medium, incubated with the antibody directed against p28ING5 followed by a second incubation with a secondary antibody that is conjugated to a fluorescent probe or a calorimetric agent. Cells that express a p28ING5 protein that is recognized by the antibody exhibit a color or are fluorescent when viewed under a light or fluorescence microscope, respectively.

An alternative method of diagnosing p28ING5 gene deletion, amplification, or mutation is to quantitate the level of p28ING5 protein in the cells of a subject. In one embodiment, this diagnostic tool would be useful for detecting reduced levels of the p28ING5 protein that result from, for example, mutations in the promoter regions of the p28ING5 gene or mutations within the coding region of the gene that produce truncated, non-functional or unstable polypeptides, as well as from deletions of the entire p28ING5 gene. In another embodiment, duplications of the p28ING5 gene may be detected as an increase in the expression level of this protein. The determination of reduced or increased p28ING5 protein levels would be an alternative or supplemental approach to the direct determination of p28ING5 gene deletion, duplication or mutation status by the methods outlined above.

The availability of antibodies specific to the p28ING5 protein will facilitate the quantitation of cellular p28ING5 protein by one of a number of immunoassay methods, which are well known in the art and are presented herein and in, for instance, Harlow and Lane (*Antibodies, A Laboratory Manual*, CSHL, New York, 1988). Many techniques are commonly known in the art for the detection and quantification of antigen. In one specific, non-limiting embodiment, the purified antigen will be bound to a substrate, the antibody of the sample will bind via its Fab portion to this antigen, the substrate will then be washed and a second, labeled antibody will then be added which will bind to the Fc portion of the antibody that is the subject of the assay. The second, labeled antibody will be species specific, ie., if the serum is from a rabbit, the second, labeled antibody will be anti-rabbit-IgG antibody. The specimen will then be washed and the amount of the second, labeled antibody that has been bound will be detected and quantified by standard methods.

Examples of methods for the detection of antibodies in biological samples, including methods employing dip strips or other immobilized assay devices, are disclosed for instance in the following patents: U.S. Pat. No. 5,965,356 (Herpes simplex virus type specific seroassay); U.S. Pat. No. 6,114,179 (Method and test kit for detection of antigens and/or antibodies); U.S. Pat. No. 6,077,681 (Diagnosis of motor neuropathy by detection of antibodies); U.S. Pat. No. 6,057,097 (Marker for pathologies comprising an autoimmune reaction and/or for inflammatory diseases); and U.S. Pat. No. 5,552,285 (Immunoassay methods, compositions and kits for antibodies to oxidized DNA bases).

In one embodiment, for the purposes of quantitating the p28ING5 protein, a biological sample of the subject, which sample includes cellular proteins, is used. Such a biological sample may be obtained from body cells, such as those present in peripheral blood, urine, saliva, tissue biopsy, amniocentesis samples, surgical specimens and autopsy material. Biological samples can be obtained from normal, healthy subjects or from subjects who are predisposed to or who are already suffering from any one of a variety of tumors such as, but not limited to, tumors of the breast, lung, colon, pancreas, liver, brain, blood, skin, prostate, testis, ovary, and stomach. In one embodiment, quantitation of p28ING5 protein is achieved by immunoassay and compared to levels of the protein found in healthy cells (e.g., cells from a subject known not to suffer from a tumor). In one embodiment, a significant (e.g., 10% or greater, for instance, 20%, 25%, 30%, 50% or more) reduction in the amount of p28ING5 protein in the cells of a subject compared to the amount of p28ING5 protein found in normal human cells would be taken as an indication that the subject may have deletions or mutations in the p28ING5 gene locus, whereas in another embodiment, a significant (e.g., 10% or greater, for instance, 20%, 25%, 30%, 50% or more) increase would indicate that a duplication or enhancing mutation had occurred.

XIII. p28ING5 Knockout and Overexpression Transgenic Animals

Mutant organisms that under-express or over-express p28ING5 protein are useful for research. Such mutants allow insight into the physiological and/or pathological role of p28ING5 in a healthy and/or pathological organism. These mutants are "genetically engineered," meaning that information in the form of nucleotides has been transferred into the mutant's genome at a location, or in a combination, in which it would not normally exist. Nucleotides transferred in this way are said to be "non-native." In one embodiment, a non-p28ING5 promoter inserted upstream of a native p28ING5 gene would be non-native. In other embodiments, an extra copy of a p28ING5 gene or other encoding sequence on a plasmid, transfected into a cell, would be non-native, whether that extra copy was p28ING5 derived from the same, or a different species.

Mutants may be, for example, produced from mammals, such as mice, that either over-express or under-express p28ING5 protein, or that do not express p28ING5 at all. In one embodiment, over-expression mutants are made by increasing the number of p28ING5-encoding sequences (such as genes) in the organism. In other embodiments, over-expression mutants are made by introducing a p28ING5-encoding sequence into the organism under the control of a constitutive or inducible or viral promoter such as the mouse mammary tumor virus (MMTV) promoter or the whey acidic protein (WAP) promoter or the metallothionein promoter. In yet other embodiments, mutants that under-express p28ING5 may be made by using an inducible or repressible promoter, or by deleting the p28ING5 gene, or by destroying or limiting the function of the p28ING5 gene, for instance by disrupting the gene by transposon insertion.

In another embodiment, antisense genes may be engineered into the organism, under a constitutive or inducible promoter, to decrease or prevent p28ING5 expression, as discussed above.

A gene is "functionally deleted" when genetic engineering has been used to negate or reduce gene expression to negligible levels. When a mutant is referred to in this application as having the p28ING5 gene altered or functionally deleted, this refers to the p28ING5 gene and to any ortholog of this gene. When a mutant is referred to as having "more than the normal copy number" of a gene, this means that it has more than the usual number of genes found in the wild-type organism, e.g., in the diploid mouse or human.

In one embodiment, a mutant mouse over-expressing p28ING5 may be made by constructing a plasmid having the p28ING5 gene driven by a promoter, such as the mouse mammary tumor virus (MMTV) promoter or the whey acidic protein (WAP) promoter. In one specific, non-limiting embodiment, this plasmid may be introduced into mouse oocytes by microinjection. The oocytes are implanted into pseudopregnant females, and the litters are assayed for insertion of the transgene. Multiple strains containing the transgene are then available for study.

WAP is quite specific for mammary gland expression during lactation, and MMTV is expressed in a variety of tissues including mammary gland, salivary gland and lymphoid tissues. In other embodiments, other promoters might be used to achieve various patterns of expression, e.g., the metallothionein promoter.

In another embodiment, an inducible system may be created in which the subject expression construct is driven by a promoter regulated by an agent that can be fed to the mouse, such as tetracycline. Such techniques are well known in the art.

In yet another embodiment, a mutant knockout animal (e.g., mouse) from which the p28ING5 gene is deleted or otherwise disabled can be made by removing coding regions of the p28ING5 gene from embryonic stem cells. The methods of creating deletion mutations by using a targeting vector have been described (see, for instance, Thomas and Capecch, *Cell* 51:503-512, 1987).

In one embodiment, knock-out mice are used as hosts to test the effects of various p28ING5 constructs on cell growth. In other embodiments, transgenic mice with the endogenous p28ING5 gene knocked-out can be used in an assay to screen for compounds that modulate the p28ING5 activity. A transgenic mouse that is heterozygous or homozygous for integrated transgenes that have functionally disrupted the endogenous p28ING5 gene can be used as a sensitive in vivo screening assay for the p28ING5 ligands and modulators of p28ING5 activity.

XIV. Nucleic Acid-Based p28ING5 Therapy

Medical genetic approaches for combating p28ING5-mediated cell development defects in subjects, such as uncontrolled or disregulated cell growth or neoplasm, are now made possible.

In one embodiment, retroviruses are a preferred vector for experiments in medical genetics, as they yield a high efficiency of infection and stable integration and expression (Orkin et al, *Prog. Med. Genet.* 7:130-142, 1988). In one specific, non-limiting embodiment, the full-length p28ING5 gene or cDNA is cloned into a retroviral vector and driven from either its endogenous promoter or, for instance, from the retroviral LTR (long terminal repeat). In other embodiments, viral transfection systems may also be utilized for this type of approach, including adenovirus, adeno-associated virus (AAV) (McLaughlin et al., *J. Virol.* 62:1963-1973, 1988), Vaccinia virus (Moss et al., *Annu. Rev. Immunol.* 5:305-324, 1987), Bovine Papilloma virus (Rasmussen et al., *Methods Enzymol.* 139:642-654, 1987) or members of the herpesvirus group such as Epstein-Barr virus (Margolskee et al., *Mol. Cell. Biol.* 8:2837-2847, 1988).

More recent developments in medical genetic techniques include the use of RNA-DNA hybrid oligonucleotides, as described by Cole-Strauss, et al. (*Science* 273:1386-1389, 1996). This technique may allow for site-specific integration of cloned sequences, thereby permitting accurately targeted gene replacement.

In addition to delivery of p28ING5 to cells using viral vectors, it is possible to use non-infectious methods of delivery. In one embodiment, lipidic and liposome-mediated gene delivery will be used for transfection of various genes (for reviews, see Templeton and Lasic, *Mol. Biotechnol.* 11:175-180, 1999; Lee and Huang, *Crit. Rev. Ther. Drug Carrier Syst.* 14:173-206; and Cooper, *Semin. Oncol.* 23:172-187, 1996). In another embodiment, cationic liposomes will be used as a viable alternative to the viral vectors (de Lima et al., *Mol. Membr. Biol.* 16:103-109, 1999). In yet other embodiments, cationic liposomes can be targeted to specific cells through the inclusion of, for instance, monoclonal antibodies or other appropriate targeting ligands (Kao et al., *Cancer Gene Ther.* 3:250-256, 1996).

XV. Pharmaceutical Compositions and Administration

P28ING5 nucleic acid, protein, and modulators of p28ING5 can be administered directly to the subject for the suppression of tumor cell growth and proliferation. Pharmaceutical compositions that include p28ING5 or functional variants can be formulated with an appropriate solid or liquid carrier, depending on the particular mode of administration chosen. The pharmaceutically acceptable carriers and excipients useful in this disclosure are conventional. For instance, parenteral formulations usually comprise injectable fluids that are pharmaceutically and physiologically acceptable fluid vehicles such as water, physiological saline, other balanced salt solutions, aqueous dextrose, glycerol or the like. Excipients that can be included are, for instance, other proteins, such as human serum albumin or plasma preparations. If desired, the pharmaceutical composition to be administered can also contain minor amounts of non-toxic auxiliary substances, such as wetting or emulsifying agents, preservatives, and pH buffering agents and the like, for example sodium acetate or sorbitan monolaurate.

The dosage form of the pharmaceutical composition will be determined by the mode of administration chosen. For instance, in addition to injectable fluids, topical and oral formulations can be employed. Topical preparations can include eye drops, ointments, sprays and the like. Oral formulations can be liquid (e.g. syrups, solutions or suspensions), or solid (e.g. powders, pills, tablets, or capsules). For solid compositions, conventional non-toxic solid carriers can include pharmaceutical grades of mannitol, lactose, starch, or magnesium stearate. Actual methods of preparing such dosage forms are known, or will be apparent, to those skilled in the art.

The pharmaceutical compositions that comprise a p28ING5 tumor suppressor in some embodiments of the disclosure will be formulated in unit dosage form, suitable for individual administration of precise dosages. For example, one possible unit dosage can contain from about 1 mg to about 1 g of p28ING5. The amount of active compound(s) administered will be dependent on the subject being treated, the severity of the affliction, and the manner of administration, and is best left to the judgment of the prescribing clinician. Within these bounds, the formulation to be administered will contain a quantity of the active component(s) in amounts effective to achieve the desired effect in the subject being treated.

The compounds of this disclosure can be administered to humans or other animals on whose cells they are effective in various manners such as topically, orally, intravenously, intramuscularly, intraperitoneally, intranasally, intradermally, intrathecally, and subcutaneously. The particular mode of administration and the dosage regimen will be selected by the attending clinician, taking into account the particulars of the case (e.g. the subject, the disease, the disease state involved, and whether the treatment is prophylactic). Treatment can involve daily or multi-daily doses of compound(s) over a period of a few days to months, or even years.

A therapeutically effective amount of a p28ING5 tumor suppressor can be the amount of p28ING5 necessary to inhibit further growth of a tumor or the amount necessary to suppress the growth of a tumor. In another embodiment, a therapeutically effective amount of a p28ING5 tumor suppressor can be the amount of p28ING5 necessary to eliminate a tumor. Specific tumor suppressive effects that can be caused by p28ING5 are described herein. In some embodiments, a tumor suppressive amount of p28ING5 is an amount sufficient to eliminate a tumor (for instance, any of the tumor suppressive amounts discussed herein) without causing a substantial cytotoxic effect (e.g. without killing more than 10% of cells in a sample).

An effective amount of p28ING5 can be administered in a single dose, or in several doses, for example daily, during a course of treatment. However, the effective amount of p28ING5 will be dependent on the subject being treated, the severity and type of the affliction, and the manner of administration of the therapeutic(s). For example, a therapeutically effective amount of p28ING5 can vary from about 0.1 mg/Kg body weight to about 1 g/Kg body weight.

Site-specific administration of the disclosed compounds can be used, for instance by applying p28ING5 to a pre-cancerous region, a region of tissue from which a neoplasm has been removed, or a region suspected of being prone to neoplastic development. In some embodiments, sustained intra-tumoral (or near-tumoral) release of the pharmaceutical preparation that comprises a therapeutically effective amount of p28ING5 may be beneficial. Slow-release formulations are known to those of ordinary skill in the art. By way of example, polymers such as bis(p-carboxyphenoxy)propane-sebacic-acid or lecithin suspensions may be used to provide sustained intra-tumoral release.

It is specifically contemplated in some embodiments that delivery is via an injected and/or implanted drug depot, for instance comprising multi-vesicular liposomes such as in DepoFoam (SkyePharma, Inc; San Diego, Calif.) (see, for instance, Chamberlain et al, *Arch. Neuro*, 50:261-264, 1993; Katri et al., *J. Pharm. Sci*. 87:1341-1346, 1998; Ye et al, *J. Control Release* 64:155-166, 2000; and Howell, *Cancer J* 7:219-227, 2001).

XVI. Kits

Kits are provided which contain the necessary reagents for determining p28ING5 gene copy number, for determining abnormal expression of p28ING5 mRNA or p28ING5 protein, or for detecting polymorphisms in p28ING5 alleles. Instructions provided in the diagnostic kits can include calibration curves, diagrams, illustrations, or charts or the like to compare with the determined (e.g., experimentally measured) values or other results.

Kits are also provided that contain cells that serve as either positive or negative controls. These control cells can be compared to experimental samples containing similar cells, for instance cells of unknown gene activity, mutational state, protein expression level, and so forth.

A. Kits for Detection of p28ING5 Genomic Sequences

The nucleotide sequences disclosed herein, and fragments thereof, can be supplied in the form of a kit for use in detection of p28ING5 genomic sequences, for instance in order to diagnose a predisposition for tumor growth or of the presence of a tumor. In one embodiment of such a kit, an appropriate amount of one or more of the p28ING5-specific oligonucleotide primers is provided in one or more containers. In other embodiments, the oligonucleotide primers may be provided suspended in an aqueous solution or as a freeze-dried or lyophilized powder, for instance. The container(s) in which the oligonucleotide(s) are supplied can be any conventional container that is capable of holding the supplied form, for instance, microfuge tubes, ampoules, or bottles. In other embodiments, pairs of primers may be provided in pre-measured single use amounts in individual, typically disposable, tubes or equivalent containers. In one specific, non-limiting embodiment, the sample to be tested for the presence of p28ING5 genomic amplification can be added to the individual tubes and in vitro amplification carried out directly.

The amount of each oligonucleotide primer supplied in the kit can be any appropriate amount, depending for instance on the market to which the product is directed. In one embodiment, the kit is adapted for research or clinical use and the amount of each oligonucleotide primer provided is an amount sufficient to prime several in vitro amplification reactions. Those of ordinary skill in the art know the amount of oligonucleotide primer that is appropriate for use in a single amplification reaction. General guidelines may for instance be found in Innis et al (*PCR Protocols, A Guide to Methods and Applications*, Academic Press, Inc., San Diego, Calif., 1990), Sambrook et al. (In *Molecular Cloning: A Laboratory Manual*, Cold Spring Harbor, N.Y., 1989), and Ausubel et al. (In *Current Protocols in Molecular Biology*, John Wiley & Sons, New York, 1998).

In one embodiment, a kit may include more than two primers, in order to facilitate the PCR in vitro amplification of p28ING5 sequences, for instance the p28ING5 gene, specific exon(s) or other portions of the gene, or the 5' or 3' flanking region thereof.

In some embodiments, kits may also include the reagents necessary to carry out PCR in vitro amplification reactions, including, for instance, DNA sample preparation reagents, appropriate buffers (e.g., polymerase buffer), salts (e.g., magnesium chloride), and deoxyribonucleotides (dNTPs). Instructions may also be included.

In other embodiments, kits may include either labeled or unlabeled oligonucleotide probes for use in detection of the in vitro amplified p28ING5 sequences. In one specific, non-limiting embodiment, the appropriate sequences for such a probe will be any sequence that falls between the annealing sites of the two provided oligonucleotide primers, such that the sequence the probe is complementary to is amplified during the in vitro amplification reaction.

In yet another embodiment, the kit provides one or more control sequences for use in the amplification reactions. The design of appropriate positive control sequences is well known to one of ordinary skill in the appropriate art.

B. Kits for Detection of p28ING5 mRNA Expression

Kits similar to those disclosed above for the detection of p28ING5 genomic sequences can be used to detect p28ING5 mRNA expression levels. One embodiment of such a kit may include an appropriate amount of one or more of the oligonucleotide primers for use in reverse transcription amplification reactions, similarly to those provided above, with art-obvious modifications for use with RNA.

In some embodiments, kits for detection of p28ING5 mRNA expression levels may also include the reagents necessary to carry out RT-PCR in vitro amplification reactions, including, for instance, RNA sample preparation reagents (including e.g., an RNAse inhibitor), appropriate buffers (e.g., polymerase buffer), salts (e.g., magnesium chloride), and deoxyribonucleotides (dNTPs). Instructions also may be included.

In other embodiments, kits may include either labeled or unlabeled oligonucleotide probes for use in detection of the in vitro amplified target sequences. In one specific, non-limiting embodiment, the appropriate sequences for such a probe will be any sequence that falls between the annealing sites of the two provided oligonucleotide primers, such that the sequence the probe is complementary to is amplified during the PCR reaction.

In another embodiment, the kit provides one or more control sequences for use in the RT-PCR reactions. The design of appropriate positive control sequences is well known to one of ordinary skill in the appropriate art.

In yet other embodiments, kits may be provided with the necessary reagents to carry out quantitative or semi-quantitative Northern analysis of p28ING5 mRNA. Such kits include, for instance, at least one p28ING5-specific oligonucleotide for use as a probe. This oligonucleotide may be labeled in any conventional way, including with a selected radioactive isotope, enzyme substrate, co-factor, ligand, chemiluminescent or fluorescent agent, hapten, or enzyme.

C. Kits For Detection of p28ING5 Protein or Peptide Expression

In some embodiments, kits for the detection of p28ING5 protein expression include for instance at least one target protein specific binding agent (e.g., a polyclonal or monoclonal antibody or antibody fragment) and may include at least one control. In another embodiment, the p28ING5 protein specific binding agent and control may be contained in separate containers. In other embodiments, the kits may also include means for detecting p28ING5:agent complexes, for instance the agent may be detectably labeled. If the detectable agent is not labeled, it may be detected by second antibodies or protein A for example which may also be provided in some kits in one or more separate containers. Such techniques are well known.

In another embodiment, the kits include instructions for carrying out the assay. Instructions will allow the tester to determine whether p28ING5 expression levels are altered, for instance in comparison to a control sample. In other embodiments, reaction vessels and auxiliary reagents such as cells, chromogens, buffers, media, enzymes, etc. also may be included in the kits.

In one specific, non-limiting embodiment, an effective and convenient immunoassay kit such as an enzyme-linked immunosorbant assay can be constructed to test anti-p28ING5 antibody in human serum, as reported for detection of non-specific anti-ovarian antibodies (Wheatcroft et al, *Clin. Exp. Immunol.* 96:122-128, 1994; Wheatcroft et al, *Hum. Reprod.* 12:2617-2622, 1997). In one embodiment, expression vectors can be constructed using the human p28ING5 cDNA to produce the recombinant human p28ING5 protein in either bacteria or baculovirus (as described herein). In another embodiment, affinity purification is used to generate unlimited amounts of pure recombinant p28ING5 protein.

In one embodiment, an assay kit could provide the recombinant protein as an antigen and enzyme-conjugated goat anti-human IgG as a second antibody as well as the enzymatic substrates. Such kits can be used to test if the sera from a subject contain antibodies against human p28ING5.

D. Kits for Detection of Homozygous versus Heterozygous Allelism

Also provided are kits that allow differentiation between individuals who are homozygous versus heterozygous for a polymorphism of p28ING5. In one embodiment such kits provide the materials necessary to perform oligonucleotide ligation assays (OLA), for instance as described at Nickerson et al. (*Proc. Natl. Acad. Sci. USA* 87:8923-8927, 1990). In specific embodiments, these kits contain one or more microtiter plate assays, designed to detect allelism in the p28ING5 sequence of a subject, as described herein.

In one embodiment, additional components in some of these kits may include instructions for carrying out the assay. Instructions will allow the tester to determine whether a p28ING5 allele is homozygous or heterozygous. In other embodiments, reaction vessels and auxiliary reagents such as chromogens, buffers, enzymes, etc. may also be included in the kits.

In another embodiment, the kit may provide one or more control sequences for use in the OLA reactions. The design of appropriate positive control sequences is well known to one of ordinary skill in the appropriate art.

E. Kits for Identifying Modulators of p28ING5 Activity

Also provided are kits that allow for the identification of modulators of p28ING5 activity. In one embodiment, such kits provide the materials necessary to assess the activity of p28ING5 in vitro. In one embodiment, this kit contains aliquots of isolated p28ING5 and cultured cells. In another embodiment, the kit contains cell lines that express either wildtype or mutant p28ING5. In yet another embodiment, additional components in some of these kits may include instructions for carrying out the assay. In other embodiments, reaction vessels and auxiliary reagents such as chromogens, buffers, media, enzymes, etc. may also be included in the kits.

Embodiments of the invention are illustrated by the following non-limiting Examples.

EXAMPLES

Example 1

Cloning of p28ING5

The p28ING5 cDNA (SEQ ID NO: 1; GenBank Accession No. AF 189286) was isolated from human placenta Marathon-Ready cDNA (Clontech) by RT-PCR and ligated into the pcDNA3.1 expression vector (InVitrogen) (pcDNA3.1-ING5). The cDNA was also cloned into the p-FLAG-CMV-2 mammalian expression vector (Sigma) to generate a pFLAG-ING5 construct expressing pFLAG fused to the amino terminal end of p28ING5.

Figure 1:
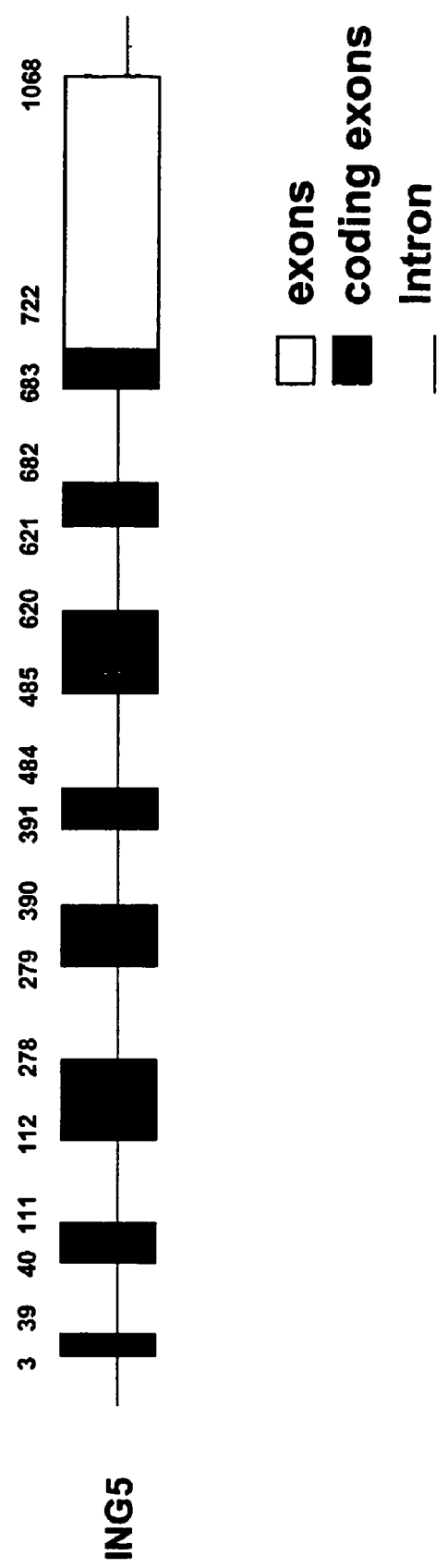
FIG. 1 shows the genomic structure of the p28ING5 gene. The eight exons that comprise the coding region are represented by the shaded boxes; the untranslated region of exon 8 is represented by a white box. Introns are depicted as bars between the exons. Nucleotides of the open-reading frame are situated above the exons and are numbered 3-722.

Human PAC and BAC clone DNA pools were screened by PCR. A human BAC clone (Research Genetics) was found containing the p28ING5 genomic sequence. The clone was amplified in liquid culture, and then purified. The BAC clone was then used to determine the genomic structure of the p28ING5 gene. p28ING5 exons were determined by sequencing and exon-intron boundaries were identified by a long distance sequencer method (Hagiwara and Harris. *Nucleic Acids Research*, 24; 2460-2461, 1996). Based on the gene sequence it was determined that the p28ING5 gene has 8 exons (FIG. 1) and encodes a protein of 240 amino acids. As is true for other members of the ING family, p28ING5 has a Plant Homeo Domain (PHD) at the carboxy terminal end of the protein (corresponding to residues 186 through 235 of SEQ ID NO: 2; see also FIG. 12), as well as at least one NLS (for example, residues 129-146 or 222-240 of SEQ ID NO: 2).

The chromosomal location of p28ING5 was determined by FISH (fluorescence in situ hybridization) analysis with the human BAC clone containing human p28ING5 genomic sequences. p28ING5 is located at chromosome 2q37.

Example 2

Northern Blot Analysis of p28ING5 Gene Expression in Normal Tissues

Human MTN Blot and human MTN Blot 11 membranes (Clontech), containing approximately 2 µg of normal human polyA+ RNA per lane, were used for Northern Blot analysis. p28ING5 cDNA was used as a probe for Northern blot analysis. Probe labeling was performed using the Prime-It RmT Random Primer Labelling kit (Stratagene) according to the manufacture's instructions. The membrane was hybridized with labeled probe in Hybrizol I (Oncor) containing 50% formaldehyde, 10% dextran sulfate, 1% SDS, and blocking agents. Hybridization was carried out at 45° C. for 16 hours. The membranes were washed with 0.1% SDS and 0.1×SSC, for 20 minutes at room temperature, and then washed with 0.1% SDS and 0.1×SSC three times at 60° C. for 20 minutes. The membranes were then exposed to autoradiographic film and following a five-day exposure, the films were developed.

Figure 2:
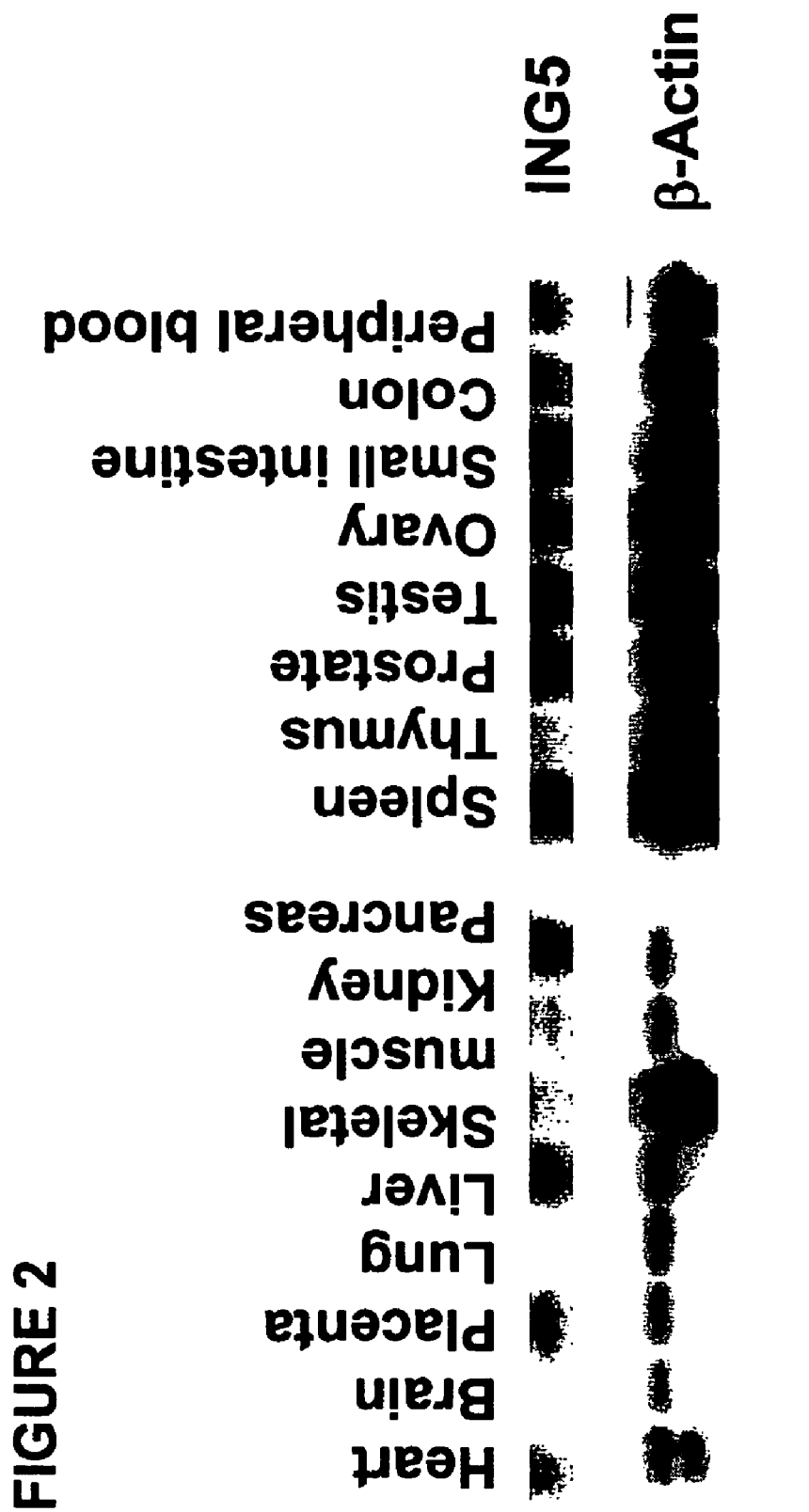
FIG. 2 shows a Northern blot analysis of p28ING5 gene expression in normal human tissues. Total RNA was isolated from the indicated human tissues and the relative expression level of p28ING5 in these tissues was examined. The p28ING5 expression level varied among the different tissues examined. p28ING5 is strongly expressed in testis, prostate, spleen, liver, small intestine and placenta, whereas it is poorly expressed in heart, brain, lung, skeletal muscle, kidney, pancreas, thymus, colon, ovary, and peripheral blood.

The p28ING5 expression level varied among the different tissues examined (FIG. 2). p28ING5 is strongly expressed in testis, prostate, spleen, small intestine, placenta, and liver, whereas it is poorly or lowly expressed in heart, brain, lung, skeletal muscle, kidney, pancreas, thymus, colon, ovary, and peripheral blood.

Example 3

Antibodies to p28ING5

Rabbit polyclonal antibodies against p28ING5 were raised against chemically synthesized, KLH-conjugated peptides SPDQRVERL (residues 57-65 in SEQ ID NO: 2; see also FIG. 12). The antisera from the immunized rabbits were affinity-purified with the respective peptide coupled to SulfoLink (Pierce). After titration by ELISA, the antisera were tested for specificity.

Figure 3:
FIG. 3 is a Western blot showing the specificity of the anti p28ING5 antiserum produced in Example 3, below. Sub-confluent cultures of RKO cells transfected with either pcDNA3.1-ING3, pcDNA3.1-ING4, pcDNA3.1-ING5 or pcDNA3.1 were harvested, lysed, electrophoresed on a 10%

Sub-confluent cultures of RKO cells transfected with either pcDNA3.1-ING3, pcDNA3.1-ING4, pcDNA3.1-ING5 or pcDNA3.1 were harvested and lysed in buffer containing 10 mM Tris-HCl (pH 7.5), 1 mM EDTA, 400 mM NaCl, 10% glycerol, 0.5% NP40, 5 mM NaF, 0.5 mM sodium orthovanadate, 1 mM dithiothreitol, and protease inhibitor cocktail (Roche). Equal amounts of cell lysates (20 μg) were resuspended in 2×Tris-glycine SDS sample buffer, electrophoresed on a 10% SDS-polyacrylamide gel and electrophoretically transferred to Immobilon-P membrane (Millipore). The membrane was then probed with the anti-p28ING5 antiserum (1:200), washed with phosphate buffered saline (PBS)-Tween 20 (0.1%; PBS-T buffer) and incubated with horseradish peroxidase-conjugated anti-rabbit IgG secondary antibody (1:2000). After washing the membrane with PBS-T buffer, the membranes were treated with the ECL chemiluminescence kit, and exposed to ECL films (Amersham Pharmacia Biotech). Only the RKO cells transfected with the pcDNA3.1-ING5 vector expressed a protein that was recognized by the anti-p28ING5 antiserum (FIG. 3).

Example 4

Expression of p28ING5 Protein in Various Cell Lines

Twelve human cell lines were grown in the recommended media and included WI 38 (normal fibroblasts), Hep 3B (hepatocellular carcinoma), OsA-CL, Saos-2 (osteosarcomas), HCT 116, RKO, RKO E6 (colorectal carcinomas), NCI-H 157, Calu-6 (non-small cell lung carcinomas), AsPC-1 (pancreatic carcinoma), and PC-3 (prostate carcinoma). The twelve human cell lines which express either wildtype p53 (WI 38, Hep 3B, HCT 116, RKO), mutant p53 (NCl-H157, AsPC-1), or which are devoid of p53 (RKO E6, Saos-2, Hep3B, PC-3, Calu-6) were examined for the expression of p28ING5. Sub-confluent cultures of cells were harvested and lysed in buffer containing 10 mM Tris-HCl (pH 7.5), 1 mM EDTA, 400 mM NaCl, 10% glycerol, 0.5% NP40, 5 mM NaF, 0.5 mM sodium orthovanadate, 1 mM dithiothreitol, and protease inhibitor cocktail (Roche). Equal amounts of cell lysates (30 μg) were resuspended in 2×Tris-glycine SDS sample buffer, electrophoresed on a 10% SDS-polyacrylamide gel, as was a positive control, and electrophoretically transferred to PVDF membranes. The membrane was then probed with the anti-p28ING5 antiserum (1:200) and after washing the membranes with PBS-Tween 20 (0.1%; PBS-T buffer), the membranes were incubated with horseradish peroxidase-conjugated anti-rabbit IgG secondary antibody (1:2000). After washing the membrane with PBS-T buffer, the membranes were treated with the ECL chemiluminescence kit, and exposed to ECL films (Amersham Pharmacia Biotech).

The expression levels of p28ING5 varied among the cell lines examined (FIG. 4). p28ING5 is strongly expressed in RKO, RKO E6, Hep 3B, PC-3, Calu-6, and NCI-H157 cells whereas little or no p28ING5 expression was observed in WI-38 or HCT 116 cells. No correlation could be made between the level of p28ING5 expression and the status of p53 in the cells.

Example 5

Subcellular Localization of p28ING5

RKO, RKOE6, HCT116, and MCF-7 cells were cultured on covered chamber slides and then transfected with pcDNA3.1-ING5 or pcDNA3.1. Twenty four hours after the transfection, cells were fixed with 4% paraformaldehyde for 30 minutes, blocked in PBS containing 0.15% glycine and 2% bovine serum albumin, then incubated with the anti-p28ING5 antiserum (1:250 dilution for one hour at room temperature). After washing the cells again, they were incubated with FITC-conjugated anti-rabbit IgG secondary antibody (1:500 dilution for 45 minutes at room temperature). The cells were then stained with DAPI and observed by fluorescent microscopy. Over-expressed p28ING5 is localized in the nucleus, and is concentrated at the periphery of the nucleus. Similar results were observed with RKO E6, HCTI 16, and MCF-7 cells.

Example 6

Mutational Analysis of p28ING5 Gene

To screen for mutations in the coding region of the p28ING5 gene, PCR-SSCP analysis essentially as described previously (Hagiwara et al., Cancer Res. 59:4165-9, 1999, Yoshikawa et al., Oncogene 18:3415-21, 1999) was carried out on a number of cell lines. Four cell lines showed aberrantly migrating bands on the SSCP gels (FIG. 6). Of the four cell lines only HCT116 cells demonstrate a single base pair insertion in exon 2, which results in a frameshift. The other three cell lines express silent point mutations (866 MT, Ls174T) or a mutation in intron 5 (DLD-4) (Table I). In addition to the inactivation of the first p28ING5 allele, the second p28ING5 allele is lost in the HCT116 cells resulting in a functional loss of both alleles of the p28ING5 gene in this cell line. Information on these mutations is summarized in Table 1.

TABLE I

Mutations in ING5 in cancer cells

| Cell Line | Exon (Codon) | Type of Mutation | Amino Acid Substitution |
|---|---|---|---|
| HCT116 | 2 (26) | CCA to TCA (1 bp insertion) | Frameshift |
| 866 MT | 3 (66) | CAG to CAA (point mutation) | Silent |
| LS174T | 3 (84) | CAG to CAA (point mutation | Silent |
| DLD-4 | intron 5 | | N/A |

Example 7

Colony Assays for Identifying Compounds that Modulate p28ING5 Activity

The effect of exogenous p29ING4 and p28ING5 overexpression on cell growth, and the dependency of these proteins on p53, was measured. RKO cells and RK0-E6 cells (an isogenic subclone of RKO cells expressing a p53 protein inactivated by ubiquitin-dependent cleavage which is mediated by the E6 protein of human papilloma virus; Kessis et al., Proc. Natl. Acad. Sci. U.S.A., 90: 3988-3992, 1993) were plated in six-well plates ($2 \times 10^4$ cells/cm$^2$), cultured for 24 hours at 37° C. and transfected with 1 μg of pcDNA3.1-ING4, pcDNA3.1-ING5, or pcDNA3.1 (control) vectors containing a hygromycin-resistance gene. OsA-CL and AsPC-1 cells were plated in six-well plates ($2 \times 10^4$ cells/cm$^2$), cultured for 24 hours at 37° C. and transfected with 1 μg of pcDNA3.1-ING4, pcDNA3.1-ING5, or pcDNA3.1 (control) vectors containing a neomycin-resistance gene. Following two weeks of hygromycin (200 μg/ml; Sigma) or neomycin (800 μg/ml; Sigma) selection, the cells were fixed with 10% formaldehyde and stained with crystal violet for colony counting. Co-transfection experiments, using the pC53-SN vector containing the wild-type p53 cDNA (Baker et al., *Science*, 249: 912-915, 1990), were carried out in AsPC-1 cells. Each experiment was performed in triplicate.

p29ING4 and p28ING5 overexpression significantly reduced the colony formation of RKO cells (FIG. 7A), whereas, p28ING5 overexpression showed no effect and p29ING4 overexpression showed minimal effect on the colony formation of RKO-E6 cells. p29ING4 and p28ING5 overexpression also resulted in a statistically significant reduction of the colony formation of the OsA-CL cells, which express wild-type p53. In contrast, p29ING4 and p28ING5 overexpression showed a minimal effect on the colony formation efficiency of the AsPC-1 cells containing mutant p53.

Transfection with 1 μg of pC53-SN (wild-type p53) markedly reduced the colony formation of the AsPC-1 cells, however transfection with 0.5 μg of the vector was insufficient for suppression of colony formation of the AsPC-1 cells. Co-transfection of pcDNA3.1-ING4 or pcDNA3.1-ING5 (0.5 μg) and p53 (0.5 μg) resulted in a significant reduction of the colony formation of AsPC-1 cells. The reduction of colony formation in cells overexpressing p28ING5 and p29ING4 indicates that these proteins can function as tumor suppressors.

In soft agar colony assay experiments, wildtype or mutant p28ING5 is expressed in host cells to screen compounds that modulate anchorage dependence of p28ING5-expressing cells. This is achieved by the method of Garkavtsev et al. (1996), supra. RKO cells are transfected with retrovirus produced from a vector containing p28ING5 in sense or antisense orientation, or a vector lacking insert (control). The soft agar culture is comprised of two layers: an underlay (Dulbecco's modified essential medium, 10% fetal calf serum, 0.6% agar) and an overlay (Dulbecco's modified essential medium, 10% fetal calf serum, 0.3% agar). $5 \times 10^4$ cells are plated in soft agar in 10 cm plates and are maintained at 37° C. for 6-7 weeks before the colonies are counted. The cells are also incubated with a test compound for a suitable amount of time, e.g. 0.5, 1, 2, 5, 10, 16, 24, 48 hours before the colonies are counted. The size and number of colonies in the test sample is then compared to control, untreated, cells.

Example 8

The Effect of Over-Expression of p28ING5 on the Cell Cycle

Cell-cycle stage analysis of cells transfected with an expression vector encoding p28ING5 was performed using the method of Jiang and Hunter (*BioTechniques*, 24:349-350, 352, 354, 1998). The method permits the analysis of cell cycle profiles in transfected cells using a membrane targeted enhanced green fluorescent protein (EGFP).

RKO or RKO-E6 cells were plated on 60 mm dishes at $2 \times 10^4$ cells/cm² 24 hours prior to transfection. Cells were co-transfected with 2 μg of pcDNA3.1-ING4, pcDNA3.1-ING5, or pcDNA3.1 (control), and 200 ng of pEGFP-F vector (Clontech) as a positive marker for transfection. Forty-eight hours following transfection, cells were harvested, washed with PBS, and fixed with 70% ethanol for more than three hours. After ethanol was removed by centrifugation, cell pellets were resuspended with a PI-RNase solution (containing 20 μg/ml of propidium iodide (Sigma) and 100 μg/ml of RNase A (Sigma)) and incubated for 30 minutes at room temperature. The DNA content of the cells was measured with FACSCalibur flow cytometer (Beckton Dickinson). Cell cycle profiles in diploid cells were analyzed using the ModFit LT Program (Verify Software House). At least 10,000 of the EGFP-positive cells (transfection-positive cells) were analyzed.

Cell cycle analysis demonstrated that p29ING4 and p28ING5 overexpression resulted in a decreased S-phase population and in increased G1/G0 and G2/M phases 48 hours following transfection of RKO cells. No significant cell cycle change was seen in RK0-E6 cells (FIG. 7B).

The TUNEL assay was used to determine the effect of p29ING4 and p28ING5 on apoptosis. RKO or RKO-E6 cells were plated onto six-well chamber slides at $1 \times 10^4$ cells/cm² and cultured for 24 hours. Cells were co-transfected with 50 ng of pcDNA3.1-ING4, pcDNA3.1-ING5, or pcDNA3.1 (control) vectors and 5 ng of the pEGFP-F vector as a marker for transfection efficiency. Cells were fixed with 4% paraformaldehyde 24 hours after transfection and apoptotic cells were detected using the terminal deoxynucleotidyltransferase-mediated dUTP nick end labeling (TUNEL) method. Fragmented DNA was labeled by terminal transferase (Boehringer Mannheim; Indianapolis, Ind.) with AlexaFluor 568-5-dUTP (Molecular Probes). Cells were stained by 4,6-diamidino-2-phenylidole (DAPI; Vector Laboratories), and apoptotic cells were counted in EGFP populations by fluorescent microscopy.

The TUNEL assay demonstrated that a significantly higher number of RKO cells transfected with pcDNA3.1-ING4 or pcDNA3.1-ING5 underwent apoptosis when compared with RKO cells transfected with pcDNA3.1 (control) (FIG. 7C). No apoptotic induction was observed in RKO-E6 cells. The percentage of the apoptotic cells in RKO or RKO-E6 cells transfected with p29ING4 or p28ING5 was also quantified as a sub-G1 population by flow cytometry. The reduction in the S-phase population of cells overexpressing p28ING5 and p29ING4, and the increase in apoptotic cells overexpressing p28ING5 and p29ING4 indicate that the p28ING5 and p29ING4 proteins can function as tumor suppressors.

Example 9

Effect of p28ING5 over-expression on p53 post-translational modifications

Over-expression of p28ING5 results in a decreased percentage of cells in S-phase, and decreased colony formation in RKO cells but not in RKO E6 cells (Examples 7 and 8). p53 is inactivated in RKO E6 cells by an ectopically expressed viral E6 protein, suggesting that p28ING5 negatively controls cell growth in a p53-dependent manner. This interaction was previously demonstrated by other members of the ING family, p33ING1b and p33ING2. Since p33ING2 acetylates a lysine residue at position 382 of the p53 protein, p28ING5 may also post-transitionally modify p53, either by acetylation or phosphorylation, thereby stabilizing p53 and modulating its function.

RKO cells were seeded on 100 mm dish at $2 \times 10^4$ cells/cm² and cultured for 24 hours. The cells were transfected with pcDNA3.1-ING1b, pcDNA3.1-ING2, pcDNA3.1-ING4, pcDNA3.1-ING5 or the control vector (pcDNA3.1). Cells were harvested at 24 hours post-transfection. In the p53 acetylation experiments, 5 μM trichostatin A (Wako) was administered to the cells for 3 hours before they were harvested. Whole cell lysates were then subjected to Western blot analysis to detect p53 or p53 phosphorylated on the serine residues at positions 15 (Ser-15) or 392 (Ser-392). Alternatively, p53 acetylated on the lysine residue at position 382 (Lys-382), was first immunoprecipitated by anti-p53 DO-1 (Calbiochem)and Pab 240 (Santa Cruz Biotechnology) antibodies conjugated to agarose. The immunoprecipate was then subjected to Western blot analysis to detect the acetylated p53.

p33ING2 increased p53Lys-382 acetylation, whereas p33ING1b had no effect (FIG. 8A). p29ING4, and to a lesser extent p28ING5, increased p53 Lys-382 acetylation. p33ING2, p29ING4, and p28ING5 increased the amount of acetylated p53 at the Lys-382 residue when compared to pcDNA3.1 (control). Over-expression of these proteins had little effect on the level of p53 expression (FIG. 8B) as the p53 phosphorylation levels of the Ser-15 and Ser-392 residues were not changed by p28ING5, p29ING4, p33ING1b, or p33ING2 protein overexpression. Thus, p28ING5 and p29ING4 enhance acetylation of p53, indicating that p28ING5 and p29ING4 can modulate p53 function through the control of its acetylation status.

Example 10

Effect of Over-Expression on p53Dependent Transactivation Activity

To test whether p28ING5 modulates the transactivation activity of p53, the promoter activity of two p53-regulated genes, p21/WAF-1 and BAX, was examined following the overexpression of p28ING5 or p29ING4. RKO or RKO-E6 cells were plated onto six well plates at $2 \times 10^4$ cells/cm² and cultured for 24 hours at 37° C. The cells were transfected with 0.5-1.0 μg of pcDNA3.1-ING5, pcDNA3.1-ING4, or pcDNA3.1 (empty vector) and either 100 ng of the p53-responsive element reporter gene constructs, WWP-Luc-p21 or PGL-Luc-BAX. The cells were also transfected with 1 ng of pRL-TK vector, as an internal control. The cells were transfected using the Lipofectamine Plus reagent (InVitrogen).

At 24 hours post-transfection, the activity of p53 as a transactivator was assessed by observing the level of luciferase activity. Luciferase activity was detected by the Dual-Luciferase Assay System (Promega), and then quantified with a Monolight 2010 luminometer (Analytical Luminescence Laboratory). The data were normalized against the internal control, pRL-TK.

The activities of the p21/WAF-1 and BAX promoters were enhanced by the overexpression of p28ING5 and p29ING4 in RKO cells, however this was not the case in RKO-E6 cells (FIG. 9A).

To confirm the results, Western blot analysis was performed to examine if either p29ING4 or p28ING5 induced p21/WAF-1 and BAX expression. RKO cells were transfected with pcDNA3.1 (control), pcDNA3.1-ING4, or pcDNA3.1-ING5 vectors. Cells were harvested at different time-points following transfection. Whole cell lysates were prepared and 15 μg of each lysate were electrophoresed on polyacrylamide gels and then subjected to Western blot analysis, using anti-p29ING4, anti-p28ING5, anti-WAF1 (Calbiochem) and anti-BAX (Ab-1, Santa Cruz Biotechnology), to detect the presence of p21/WAF1, BAX, p29ING4 or p28ING5. Numbers beneath each lane represent densitometry values expressed as a relative ratio of the increase in amount of protein detected versus the increase in the amount of control protein (actin) over time.

The expression of p21/WAF1 was markedly increased by p29ING4 or p28ING5 overexpression in RKO cells, whereas minimal induction of the p21/WAF1 by the pcDNA3.1 control vector was observed (FIG. 9B). A modest increase in BAX was observed by p29ING4 or p28ING5 overexpression. In RKO-E6 cells, no p21/WAF1 or BAX increase was observed when p29ING4 or p28ING5 were overexpressed.

The results indicate that p28ING5 and p29ING4 overexpression activates p21/WAF-1 and BAX promoters and increases the level of p21/WAF and BAX in RKO, but not in RKO-E6, cells. Thus, p28ING5 and p29ING4 can modulate the transcriptional activity of p53.

Example 11

Identification of an In Vivo Interaction Between p28ING5 and p53 or p300

The ability of p29ING4 or p28ING5 bind to p53 in vivo was investigated. Whole cell lysates were prepared from transfected RKO cells using an ice-cold lysate buffer containing 10 mM Tris-HCl (pH 8.0), 150 mM NaCl, 1 mM EDTA (pH 8.0), 0.5% NP-40, and a complete protease inhibitor cocktail (Roche Molecular Biochemicals). For immunoprecipitation, the following agarose-conjugated antibodies were used: rabbit polyclonal anti-p300 (N-15, Santa Cruz Biotechnology), mouse monoclonal anti-FLAG M2 antibody (Sigma), and anti-p53 antibodies, DO-1 and Pab240. Two micrograms of the antibody were incubated with 1 mg of the lysate for 1 hour. In some experiments, to block specific binding between antibody and antigen, a specific-blocking peptide (20 μg) was mixed with the antibody and incubated for 2 hours at room temperature, prior to adding the lysate. After washing, the samples were analyzed by Western blot to detect p53.

p53 was co-immunoprecipitated with p29ING4 from an RKO cell lysate using the anti-ING4 antibody, but not with preimmunized rabbit IgG (FIG. 10A). A specific-blocking peptide inhibited the co-immunoprecipitation. p53 was also co-immunoprecipitated from an RKO cell lysate with the anti-ING5 antibody, but not with preimmunized rabbit IgG. A blocking peptide again inhibited p53 co-immunoprecipitation with anti-ING5 antibody (FIG. 10B). In reverse experiments, cell extracts from RKO cells transfected with FLAG-ING4 or FLAG-ING5 were immunoprecipitated with anti-p53 murine monoclonal antibodies (DO-I and PAb240). p29ING4 and p28ING5 were clearly detected following anti-p53 antibody immunoprecipitation (FIG. 10C). The results indicate that p29ING4 and p28ING5 physically interact with p53 in vivo. The interaction of p28ING5 and p29ING4 with p53 indicates that p28ING5 and p29ING4 are regulators of p53-mediated cellular processes. p300 is a. component of histone acetyl transferase (HAT) complexes and stimulates p53 sequence-specific DNA-binding through acetylation of Lysine 382 (Gu and Roeder, *Cell*, 90:595-606, 1997; Sakaguchi et al, *Genes Dev.* 12:2831-2841, 1998; Liu et al., *Mol. Cell. Biol.* 19:1202-1209, 1999). In vivo physical interactions between p29ING4 or p28ING5 and p300 were examined by co-immunoprecipitation. RKO cells transfected with either FLAG-ING4 or FLAG-ING5 were immunoprecipitated with either the anti-FLAG or anti-p300 antibody, and anti-p300 or anti-FLAG antibodies were used for Western blot analysis (FIG. 11). Several bands are detected for p300, reflecting a post-translational modifications of the protein (Yaciuk and Moran, *Mol. Cell. Biol.* 11:5389-5397, 1991) or non-specific staining (FIG. 11A). In all experiments, the presence of either p300 or FLAG was detected, indicating that ING4 and ING5 physically interact with p300. Therefore, p29ING4 and p28ING5 are likely to be present in certain HAT complexes.

Example 12

Treating a Neoplasm in a Subject

This example describes a protocol to facilitate the treatment of a neoplasm in a subject using the p28ING5 tumor suppressor. This protocol is intended to serve as an example of such a treatment method, and is not meant to be limiting. Those of skill in the art will be able to modify the protocol to suit the needs of the subject, and to optimize for the particular compounds used. Subjects can, but need not, have received previous chemo- radio- or gene therapeutic treatments. The p28ING5 tumor suppressor may be administered to the subject in combination with other drugs, such as cytokines or anti-tumor drugs p28ING5 is administered orally or parenterally in dosage unit formulations containing standard, well known non-toxic physiologically acceptable carriers and vehicles as desired. The term parenteral as used herein includes subcutaneous injections, intravenous, intramuscular, intra-arterial injection, or infusion techniques. p28ING5 can be administered in dosages of about 0.1 mg/kg to about 1 g/kg. The p28ING5 can be delivered to the subject before, after or concurrently with the other anti-tumor agents.

A typical treatment course can comprise about six doses delivered over a 7 to 21 day period. Upon election by the clinician, the regimen can be continued six doses every three weeks or on a more frequent (daily, twice daily, four times a day, etc.) or less frequent (monthly, bimonthly, quarterly, etc.) basis. Of course, these are only exemplary times for treatment, and the skilled practitioner will readily recognize that many other time-courses are possible. The p28ING5 tumor suppressor can be combined with any of a number of conventional chemotherapeutic regimens.

Regional delivery of p28ING5 is an efficient method for delivering a therapeutically effective dose to counteract the clinical disease. Likewise, the chemotherapeutic agents can be directed to a particular affected region. Alternatively, systemic delivery of either or both agents can be appropriate.

Clinical responses can be defined by an acceptable measure. For example, a complete response can be defined by the disappearance of a tumor for at least a month. A partial response can be defined by a 50% or greater reduction of the sum of the products of perpendicular diameters of all evaluable tumor nodules for at least 1 month with no tumor sites showing enlargement. Similarly, a mixed response can be defined by a reduction of the product of perpendicular diameters of all measurable lesions by 50% or greater with progression in one or more sites.

Of course, the above-described treatment regimes can be altered by those of skill in the art, who will be able to take the information disclosed in this specification and optimize treatment regimes.

Embodiments of this disclosure provide p28ING5 proteins and nucleic acid molecules, and methods of isolating, making, and using these molecules. Further embodiments provide methods for ameliorating, treating, detecting, prognosing and diagnosing diseases related to expression of p28ING5. It will be apparent that the precise details of the methods described may be varied or modified without departing from the spirit of the described invention. We claim all such modifications and variations that fall within the scope and spirit of the claims below.

We claim:

1. A purified p28ING5 tumor suppressor protein having a sequence comprising the amino acid sequence set forth as SEQ ID NO: 2, wherein the protein has tumor suppressor activity.

2. A composition comprising the tumor suppressor protein of claim 1.

3. A purified p28ING5 tumor suppressor protein having a sequence consisting of the amino acid sequence set forth as SEQ ID NO: 2.

* * * * *

SEQUENCE LISTING

```
<160> NUMBER OF SEQ ID NOS: 2

<210> SEQ ID NO 1
<211> LENGTH: 1068
<212> TYPE: DNA
<213> ORGANISM: Homo sapiens
<220> FEATURE:
<221> NAME/KEY: CDS
<222> LOCATION: (3)..(725)

<400> SEQUENCE: 1 ag atg gcg acc gcc atg tac ttg gag cac tat ctg gac agt atc gag        47
   Met Ala Thr Ala Met Tyr Leu Glu His Tyr Leu Asp Ser Ile Glu
   1               5                  10                  15 aac ctt ccc tgc gaa ctt cag agg aac ttc cag ctg atg cga gag ctg       95
Asn Leu Pro Cys Glu Leu Gln Arg Asn Phe Gln Leu Met Arg Glu Leu
                20                  25                  30 gac cag agg acg gaa gat aag aaa gca gag att gac atc ctg gct gca      143
Asp Gln Arg Thr Glu Asp Lys Lys Ala Glu Ile Asp Ile Leu Ala Ala
            35                  40                  45 gag tac atc tcc acg gtg aag acg ctg tct cca gac cag cgc gtg gag      191
Glu Tyr Ile Ser Thr Val Lys Thr Leu Ser Pro Asp Gln Arg Val Glu
        50                  55                  60 cgc ctg cag aag atc cag aac gcc tac agc aag tgc aag gaa tac agt      239
Arg Leu Gln Lys Ile Gln Asn Ala Tyr Ser Lys Cys Lys Glu Tyr Ser
    65                  70                  75 gac gac aaa gtg cag ctg gcc atg cag acc tac gag atg gtg gat aaa      287
Asp Asp Lys Val Gln Leu Ala Met Gln Thr Tyr Glu Met Val Asp Lys
80                  85                  90                  95
```

```
cac att cga agg ctt gat gca gac ctg gcg cgc ttt gaa gca gat ctg        335
His Ile Arg Arg Leu Asp Ala Asp Leu Ala Arg Phe Glu Ala Asp Leu
            100                 105                 110 aag gac aag atg gag ggc agt gat ttt gaa agc tcc gga ggg cga ggg        383
Lys Asp Lys Met Glu Gly Ser Asp Phe Glu Ser Ser Gly Gly Arg Gly
        115                 120                 125 tta aaa aaa ggc cgg ggt cag aaa gaa aaa aga ggg tcc cgg ggc cga        431
Leu Lys Lys Gly Arg Gly Gln Lys Glu Lys Arg Gly Ser Arg Gly Arg
        130                 135                 140 ggc agg agg aca tca gag gaa gac aca cca aag aaa aag aag cac aaa        479
Gly Arg Arg Thr Ser Glu Glu Asp Thr Pro Lys Lys Lys Lys His Lys
145                 150                 155 gga ggg tct gag ttc act gac acc atc ctg tcc gtg cac ccc tct gat        527
Gly Gly Ser Glu Phe Thr Asp Thr Ile Leu Ser Val His Pro Ser Asp
160                 165                 170                 175 gtg ctg gac atg ccc gtg gac cca aac gaa ccc acg tac tgc ctg tgc        575
Val Leu Asp Met Pro Val Asp Pro Asn Glu Pro Thr Tyr Cys Leu Cys
                180                 185                 190 cac cag gtc tcc tat ggg gag atg att ggc tgt gac aat cca gac tgt        623
His Gln Val Ser Tyr Gly Glu Met Ile Gly Cys Asp Asn Pro Asp Cys
            195                 200                 205 cca att gag tgg ttt cac ttt gcc tgc gtg gac ctt acc acg aaa ccc        671
Pro Ile Glu Trp Phe His Phe Ala Cys Val Asp Leu Thr Thr Lys Pro
        210                 215                 220 aaa gga aaa tgg ttc tgt cca cgg tgt gtc cag gaa aag agg aag aag        719
Lys Gly Lys Trp Phe Cys Pro Arg Cys Val Gln Glu Lys Arg Lys Lys
        225                 230                 235 aag tag gaggagctgt gtgcccggat ccgaggagca agttaatctg tcccttcatt        775
Lys
240 cgtgtcgcaa tatttccctt ccttttaaaa ctaccttgtt cggttgatac ttagtaactc        835 cgtggccagt tgaagcgctg gatgtttcct agaacaagaa ccaccaaagc ctgttcgcac        895 agaagggcga ccttgcaggg actcgccgcc gcgacctcag tgtggctttt acaggactcc        955 ccccgagcat cagcagggac cccggcggac gtgggcgggc gcgcgtgagc tcgggctgcc       1015 cggccgggcg tgcgggcggg gacatggtaa cctggtccac ggagggcggc cgc             1068

<210> SEQ ID NO 2
<211> LENGTH: 240
<212> TYPE: PRT
<213> ORGANISM: Homo sapiens

<400> SEQUENCE: 2

Met Ala Thr Ala Met Tyr Leu Glu His Tyr Leu Asp Ser Ile Glu Asn
1               5                   10                  15

Leu Pro Cys Glu Leu Gln Arg Asn Phe Gln Leu Met Arg Glu Leu Asp
                20                  25                  30

Gln Arg Thr Glu Asp Lys Lys Ala Glu Ile Asp Ile Leu Ala Ala Glu
            35                  40                  45

Tyr Ile Ser Thr Val Lys Thr Leu Ser Pro Asp Gln Arg Val Glu Arg
        50                  55                  60

Leu Gln Lys Ile Gln Asn Ala Tyr Ser Lys Cys Lys Glu Tyr Ser Asp
65                  70                  75                  80

Asp Lys Val Gln Leu Ala Met Gln Thr Tyr Glu Met Val Asp Lys His
                85                  90                  95

Ile Arg Arg Leu Asp Ala Asp Leu Ala Arg Phe Glu Ala Asp Leu Lys
            100                 105                 110
```

```
                            -continued

Asp Lys Met Glu Gly Ser Asp Phe Glu Ser Ser Gly Gly Arg Gly Leu
        115                 120                 125

Lys Lys Gly Arg Gly Gln Lys Glu Lys Arg Gly Ser Arg Gly Arg Gly
130                 135                 140

Arg Arg Thr Ser Glu Glu Asp Thr Pro Lys Lys Lys His Lys Gly
145                 150                 155                 160

Gly Ser Glu Phe Thr Asp Thr Ile Leu Ser Val His Pro Ser Asp Val
                165                 170                 175

Leu Asp Met Pro Val Asp Pro Asn Glu Pro Thr Tyr Cys Leu Cys His
            180                 185                 190

Gln Val Ser Tyr Gly Glu Met Ile Gly Cys Asp Asn Pro Asp Cys Pro
        195                 200                 205

Ile Glu Trp Phe His Phe Ala Cys Val Asp Leu Thr Thr Lys Pro Lys
        210                 215                 220

Gly Lys Trp Phe Cys Pro Arg Cys Val Gln Glu Lys Arg Lys Lys Lys
225                 230                 235                 240
```